(12) United States Patent
van der Walt et al.

(10) Patent No.: US 8,911,447 B2
(45) Date of Patent: Dec. 16, 2014

(54) SYSTEMS AND METHODS FOR JOINT REPLACEMENT

(75) Inventors: Nicholas van der Walt, Laguna Hills, CA (US); Charles S. Shapiro, Fountain Valley, CA (US); Santiago P. Borja, Tucson, AZ (US)

(73) Assignee: OrthAlign, Inc., Aliso Viejo, CA (US)

( * ) Notice: Subject to any disclaimer, the term of this patent is extended or adjusted under 35 U.S.C. 154(b) by 979 days.

(21) Appl. No.: 12/626,162

(22) Filed: Nov. 25, 2009

(65) Prior Publication Data

US 2010/0137869 A1 Jun. 3, 2010

Related U.S. Application Data

(63) Continuation of application No. 12/509,414, filed on Jul. 24, 2009, now abandoned.

(60) Provisional application No. 61/102,754, filed on Oct. 3, 2008, provisional application No. 61/135,863, filed on Jul. 24, 2008, provisional application No. 61/102,767, filed on Oct. 3, 2008, provisional application No. 61/155,093, filed on Feb. 24, 2009, provisional application No. 61/104,644, filed on Oct. 10, 2008, provisional application No. 61/153,268, filed on Feb. 17, 2009, provisional application No. 61/153,257, filed on Feb. 17, 2009, provisional application No. 61/153,255, filed on Feb. 17, 2009, provisional application No. 61/173,158, filed on Apr. 27, 2009, provisional application No. 61/187,632, filed on Jun. 16, 2009, provisional application No. 61/173,159, filed on Apr. 27, 2009.

(51) Int. Cl.
*A61B 17/58* (2006.01)
*A61B 17/60* (2006.01)
*A61F 2/00* (2006.01)

(52) U.S. Cl.
USPC .......................................................... 606/102

(58) Field of Classification Search
USPC .......................................................... 606/102
See application file for complete search history.

(56) References Cited

U.S. PATENT DOCUMENTS 3,174,080 A 3/1965 Scott
3,670,324 A 6/1972 Trevor, 3rd
(Continued)

FOREIGN PATENT DOCUMENTS

CA 2 241 359 12/1999
CA 2 594 874 7/2006
(Continued)

OTHER PUBLICATIONS

International Search Report for International Application No. PCT/US2009/051769 dated Nov. 11, 2009, in 11 pages.

(Continued)

*Primary Examiner* — Sameh Boles
(74) *Attorney, Agent, or Firm* — Knobbe Martens Olson & Bear, LLP

(57) ABSTRACT

Systems and methods for joint replacement are provided. The systems and methods include a surgical orientation device and at least one orthopedic fixture. The surgical orientation device and orthopedic fixtures can be used to locate the orientation of an axis in the body, to adjust an orientation of a cutting plane or planes along a bony surface, to distract a joint, or to otherwise assist in an orthopedic procedure or procedures.

20 Claims, 70 Drawing Sheets

(56) References Cited

U.S. PATENT DOCUMENTS

| | | |
|---|---|---|
| 4,349,018 A | 9/1982 | Chambers |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,129,908 A | 7/1992 | Petersen |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Petersen |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliott et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allen |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,348,058 B1 | 2/2002 | Melkent et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,381,485 B1 | 4/2002 | Hunter et al. |
| 6,395,005 B1 | 5/2002 | Lovell |
| 6,447,448 B1 | 9/2002 | Ishikawa et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,679,916 B1 | 1/2004 | Frankle et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,997,882 B1 | 2/2006 | Parker et al. |
| 7,007,699 B2 | 3/2006 | Martinelli et al. |
| 7,021,140 B2 | 4/2006 | Perkins |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,331,932 B2 | 2/2008 | Leitner |
| 7,344,541 B2 | 3/2008 | Haines et al. |
| 7,392,076 B2 | 6/2008 | Moctezuma de la Barrera |
| 7,396,357 B2 | 7/2008 | Tornier et al. |
| 7,468,075 B2 | 12/2008 | Lang et al. |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,578,821 B2 | 8/2009 | Fisher et al. |
| 7,611,520 B2 | 11/2009 | Broers et al. |
| 7,611,522 B2 | 11/2009 | Gorek |
| 7,621,920 B2 | 11/2009 | Claypool et al. |

(56) References Cited

U.S. PATENT DOCUMENTS

| | | |
|---|---|---|
| 7,623,902 B2 | 11/2009 | Pacheco |
| 7,831,292 B2 | 11/2010 | Quaid et al. |
| 7,834,847 B2 | 11/2010 | Boillot et al. |
| 8,057,479 B2 | 11/2011 | Stone |
| 8,118,815 B2 | 2/2012 | van der Walt |
| 8,241,296 B2 | 8/2012 | Wasielewski |
| 8,277,455 B2 | 10/2012 | Couture et al. |
| 8,355,773 B2 | 1/2013 | Leitner et al. |
| 8,421,854 B2 | 4/2013 | Zerkin |
| 8,512,346 B2 | 8/2013 | Couture |
| 8,551,108 B2 | 10/2013 | Pelletier et al. |
| 8,588,892 B2 | 11/2013 | Hladio et al. |
| 2002/0077540 A1 | 6/2002 | Kienzle, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |
| 2003/0019294 A1 | 1/2003 | Richter |
| 2003/0069591 A1* | 4/2003 | Carson et al. ............... 606/130 |
| 2003/0093080 A1 | 5/2003 | Brown et al. |
| 2003/0105470 A1 | 6/2003 | White |
| 2003/0120282 A1 | 6/2003 | Scouten et al. |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0147926 A1 | 7/2004 | Iversen |
| 2004/0149036 A1 | 8/2004 | Foxlin et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0243148 A1 | 12/2004 | Wasielewski |
| 2005/0021037 A1 | 1/2005 | McCombs et al. |
| 2005/0021044 A1* | 1/2005 | Stone et al. ............... 606/102 |
| 2005/0107799 A1 | 5/2005 | Graf et al. |
| 2005/0113846 A1 | 5/2005 | Carson |
| 2005/0149040 A1 | 7/2005 | Haines et al. |
| 2005/0209605 A1 | 9/2005 | Grimm et al. |
| 2005/0222574 A1 | 10/2005 | Giordano et al. |
| 2005/0251026 A1 | 11/2005 | Stone |
| 2005/0251148 A1 | 11/2005 | Friedrich |
| 2006/0015018 A1 | 1/2006 | Jutras et al. |
| 2006/0020177 A1 | 1/2006 | Seo et al. |
| 2006/0064105 A1 | 3/2006 | Raistrick et al. |
| 2006/0089657 A1 | 4/2006 | Broers et al. |
| 2006/0094958 A1 | 5/2006 | Marquart et al. |
| 2006/0142656 A1 | 6/2006 | Malackowski et al. |
| 2006/0142657 A1 | 6/2006 | Quaid et al. |
| 2006/0184177 A1 | 8/2006 | Echeverri |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0032748 A1 | 2/2007 | McNeil et al. |
| 2007/0162142 A1 | 7/2007 | Stone |
| 2007/0179626 A1 | 8/2007 | de la Barrera et al. |
| 2007/0219561 A1 | 9/2007 | Lavallee et al. |
| 2007/0226986 A1 | 10/2007 | Park et al. |
| 2007/0270973 A1 | 11/2007 | Johnson et al. |
| 2007/0287911 A1 | 12/2007 | Haid et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0183179 A1 | 7/2008 | Siebel et al. |
| 2008/0195109 A1 | 8/2008 | Hunter et al. |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0088753 A1 | 4/2009 | Aram et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0292227 A1 | 11/2009 | Scholten et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0100154 A1 | 4/2010 | Roche |
| 2010/0121334 A1 | 5/2010 | Couture et al. |
| 2010/0137869 A1 | 6/2010 | Borja et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198275 A1 | 8/2010 | Chana et al. |
| 2010/0204551 A1 | 8/2010 | Roche |
| 2010/0204575 A1 | 8/2010 | Roche et al. |
| 2010/0204955 A1 | 8/2010 | Roche et al. |
| 2010/0239996 A1 | 9/2010 | Ertl |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |

(56) References Cited

U.S. PATENT DOCUMENTS

| | | |
|---|---|---|
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0157887 A1 | 6/2012 | Fanson et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |

FOREIGN PATENT DOCUMENTS

| | | |
|---|---|---|
| CA | 2 537 711 | 8/2007 |
| DE | 4 225 112 | 12/1993 |
| DE | 29704393 | 8/1997 |
| DE | 198 30 359 | 1/2000 |
| EP | 0 557 591 | 9/1993 |
| EP | 1 817 547 | 4/2012 |
| GB | 2 197 790 | 6/1988 |
| JP | 07-184929 | 7/1995 |
| JP | H08-240611 | 9/1996 |
| JP | 2006-314775 | 11/2006 |
| JP | 2007-503289 | 2/2007 |
| JP | 2007-534351 | 11/2007 |
| WO | WO 99/60939 | 12/1999 |
| WO | WO 01/30247 | 5/2001 |
| WO | WO 02/00131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2007/136784 | 11/2007 |
| WO | WO 2008/073999 A2 | 6/2008 |
| WO | WO 2009/117833 | 10/2009 |
| WO | WO 2010/011978 | 1/2010 |
| WO | WO 2010/030809 | 3/2010 |
| WO | WO 2012/006172 | 1/2012 |
| WO | WO 2012/027815 | 3/2012 |
| WO | WO 2012/027816 | 3/2012 |
| WO | WO 2012/113054 | 8/2012 |

OTHER PUBLICATIONS 510 (k) Summary for Total Knee Surgetics Navigation System, in 5 pages.
510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Microsurgical Accuracy, Medical Image Computing and Computer-Assisted Intervention, 2000, vol. 1935, pp. 878-887.
Arnold-Moore, et. al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bargren, MD., et al,, Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, vol. website brochure, pp. 13 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, pp. 21 pages.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Goniometer, AllHeart.com, 2004, website: http://allheart.com/allheart, (1 page).
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
Jenny, et al., Computer-Assisted Implantation of Total Knee Prosthesis: A Case-Control Comparative Study with Classical Instrumentation, Computer Aided Surgery, 2001, vol. 6, pp. 217-220.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.

(56) References Cited

OTHER PUBLICATIONS

Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, Pages in 88 pages.
Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA GENESIS II Anterior Cut First, Surgical Technique, Smith & Nephew, Nov. 2003, Memphis TN, in 16 pages.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. al., Atlas: A nested Relational Database System for Text Applications, IEEE Transactions on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Visser, et al., 3D Analysis of Upper Body Movements in Bilateral Amputee Gait Using Inertial Sensors, Journal of Biomechanics, Jan. 1, 2007, vol. 40, Issue S509.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.
European Office Action for Application No. 04776379.2, dated May 4, 2010, in 5 pages.
International Preliminary Report for Application No. PCT/US2004/018244, dated Dec. 13, 2005, in 11 pages.
International Search Report for Application No. PCT/US2004/018244, dated Feb. 15, 2005, in 4 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
Final Office Action for U.S. Appl. No. 10/864,085, dated Jan. 7, 2009, in 19 pages.
Final Office Action for U.S. Appl. No. 10/864,085, dated May 25, 2010, in 16 pages.
Notice of Allowance for U.S. Appl. No. 10/864,085, dated Aug. 23, 2011, in 17 pages.
Office Action for U.S. Appl. No. 10/864,085, dated Mar. 31, 2008, in 19 pages.
Office Action for U.S. Appl. No. 11/182,528, dated Jun. 25, 2008, in 10 pages.
Office Action for U.S. Appl. No. 10/864,085, dated Oct. 21, 2009, in 17 pages.
Office Action for U.S. Appl. No. 12/502,182, dated Oct. 8, 2010, in 13 pages.
Office Action for U.S. Appl. No. 10/864,085, dated Nov. 24, 2010, in 20 pages.
Office Action for U.S. Appl. No. 12/369,693, dated May 11, 2011, in 8 pages.
Office Action issued in U.S. Appl. No. 12/369,688, dated Sep. 5, 2012.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, received Mar. 14, 2005, in 10 pages.
International Search Report and Written Opinion issued in PCT Application No. PCT/US2013/039770, dated Sep. 25, 2013.
International Search Report and Written Opinion issued in PCT Application No. PCT/US2013/041556, dated Sep. 13, 2013.
International Search Report and Written Opinion issued in PCT Application No. PCT/US2013/053182, dated Nov. 11, 2013.
Bae et al., "Computer Assisted Navigation in Knee Arthroplasty", Clinics in Orthopedic Surgery, 2011, vol. 3, pp. 259-267.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Haaker et al., "Computer-Assisted Navigation Increases Precision of Component Placement in Total Knee Arthroplasty", Clinical Orthopaedics and Related Research, Apr. 2005, vol. 433, pp. 152-159.
Konyves et al., "The importance of leg length discrepancy after total hip arthroplasty", The Journal of Bone & Joint Surgery (Br), Feb. 2005, vol. 87-B, No. 2, pp. 155-157.
Noble et al., "Computer Simulation: How Can it Help the Surgeon Optimize Implant Position?", Clinical Orthopaedics and Related Research, Dec. 2003, vol. 417, pp. 242-252.
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Upadhyay et al., "Medical Malpractice in Hip and Knee Arthroplasty", The Journal of Arthroplasty, 2007, vol. 22, No. 6, Suppl. 2, pp. 2-7.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.

* cited by examiner

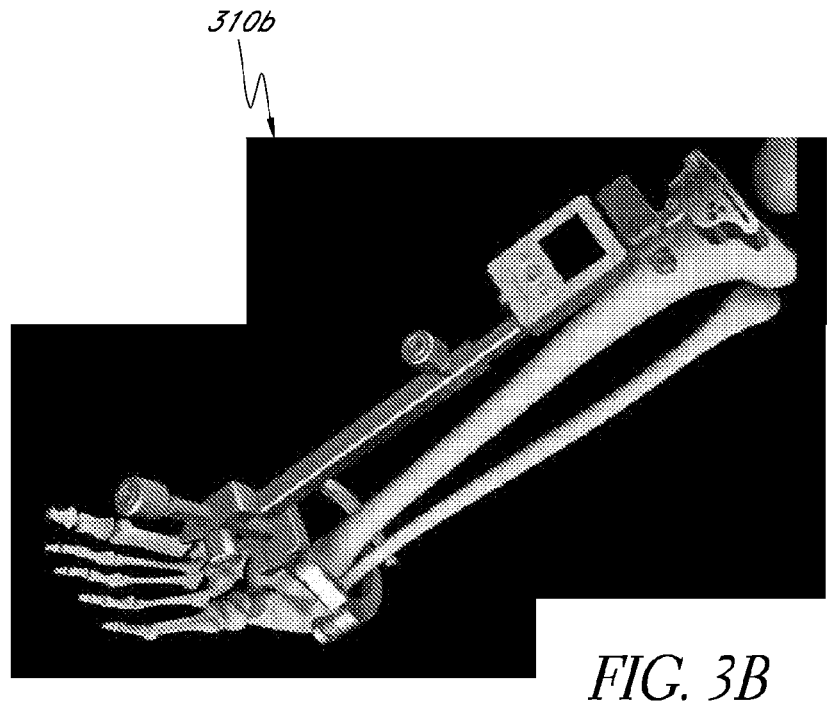
FIG. 3B
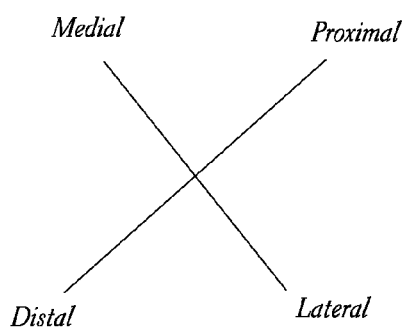

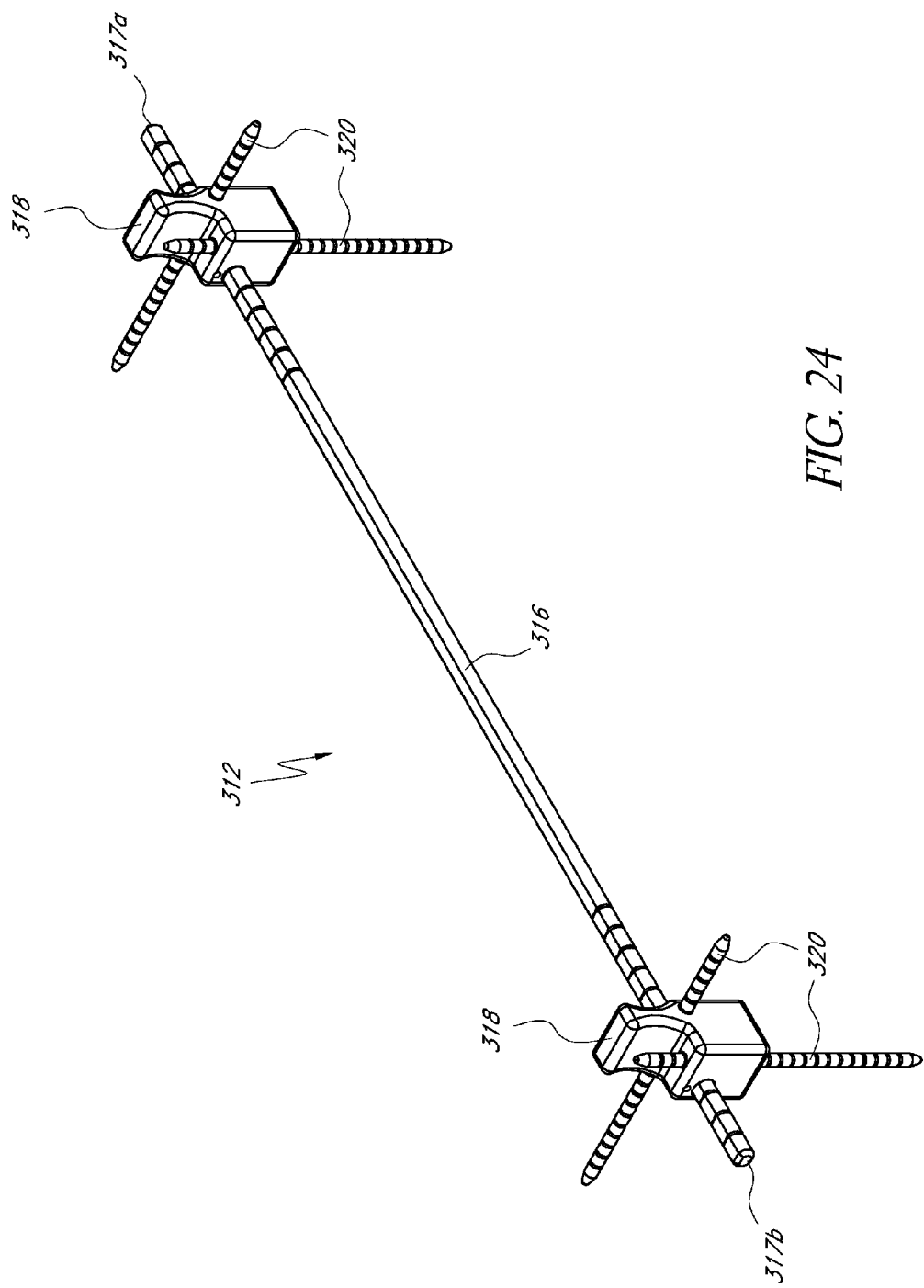

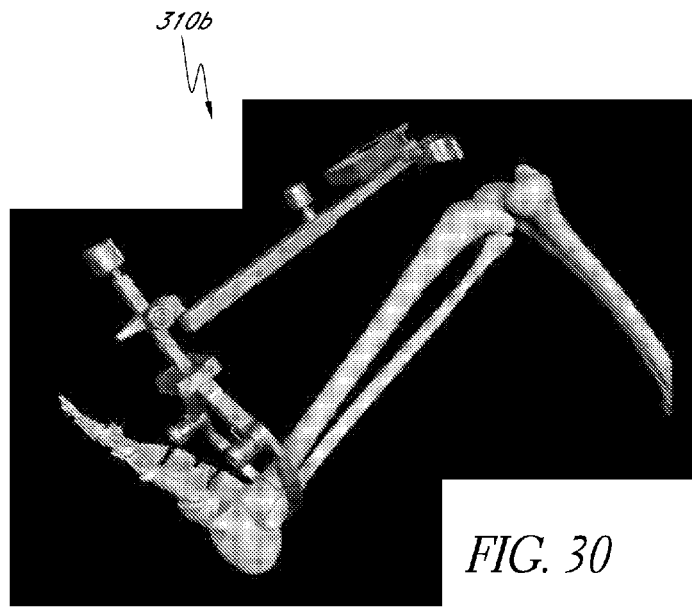
FIG. 30
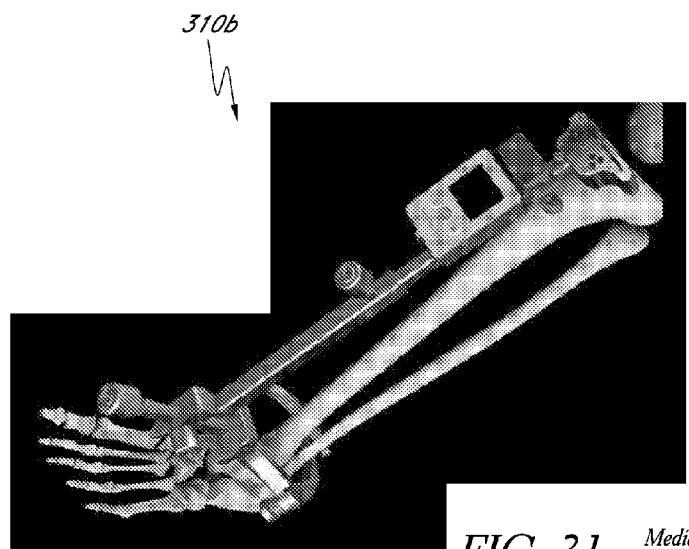
FIG. 31
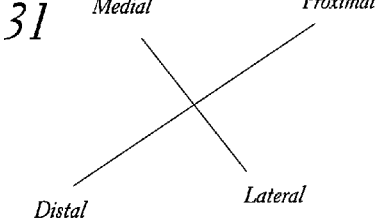

FIG. 34A
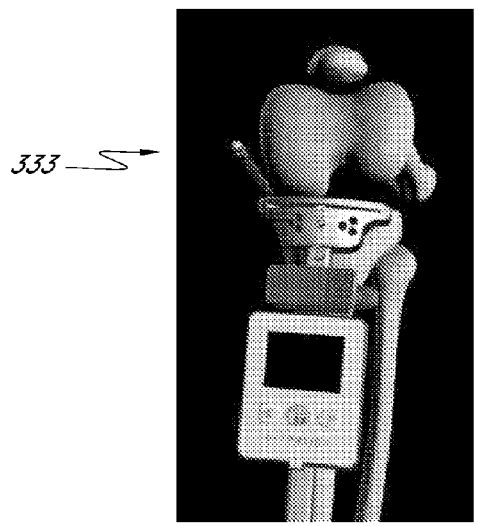
333
310b
FIG. 34B
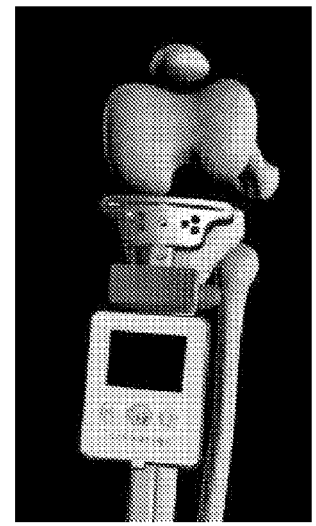
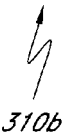
310b
FIG. 35A
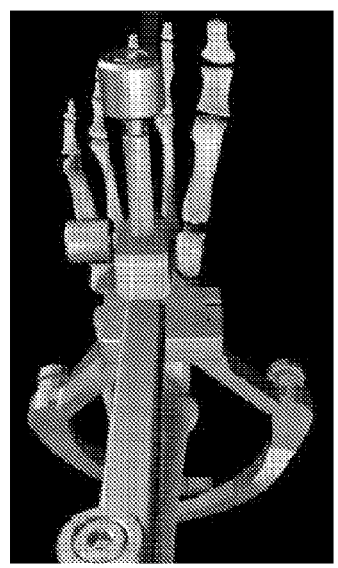
310b
FIG. 35B
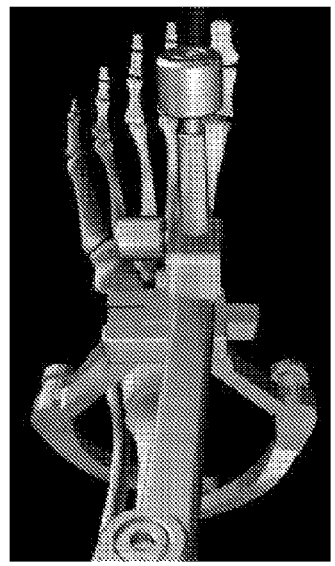
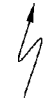
310b

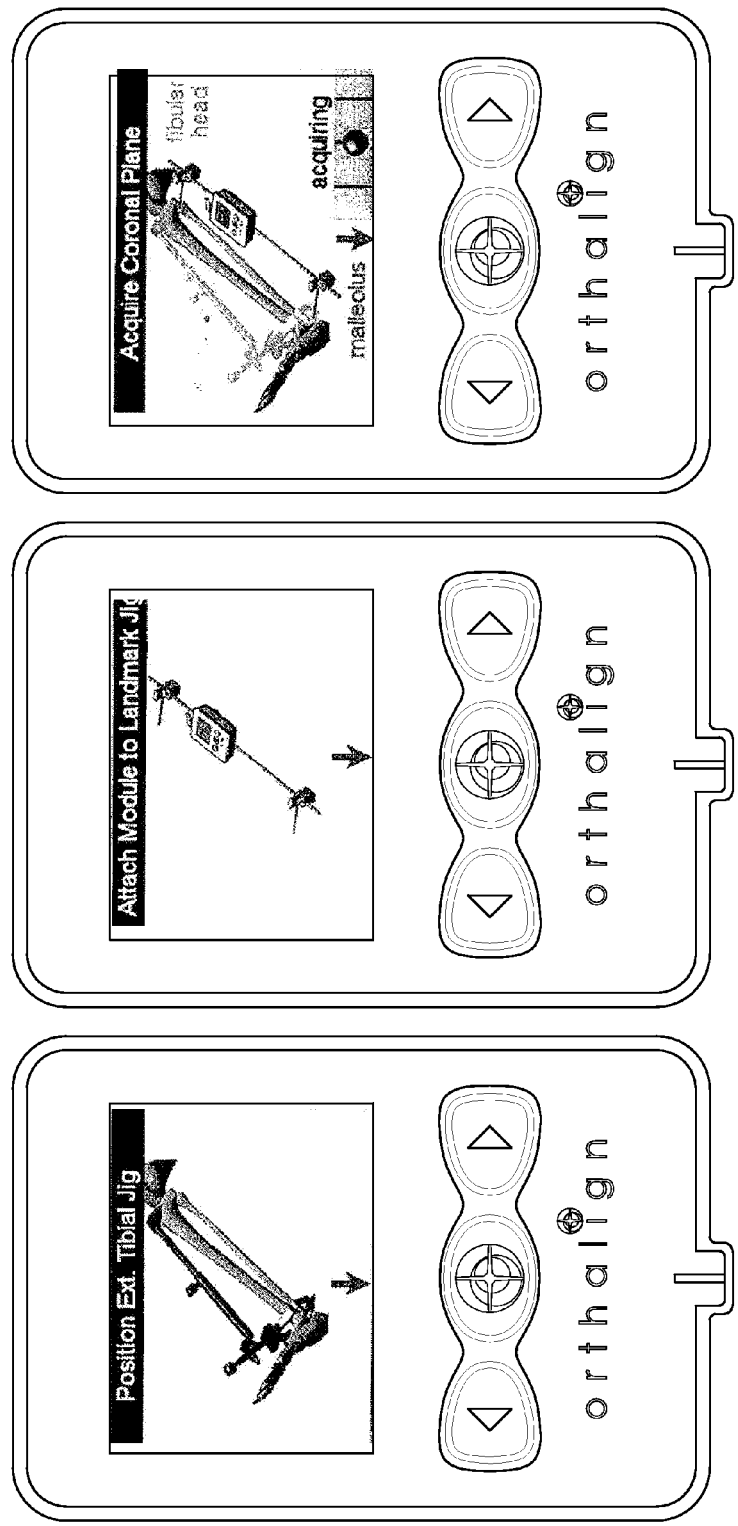
*FIG. 59C*  *FIG. 59B*  *FIG. 59A*

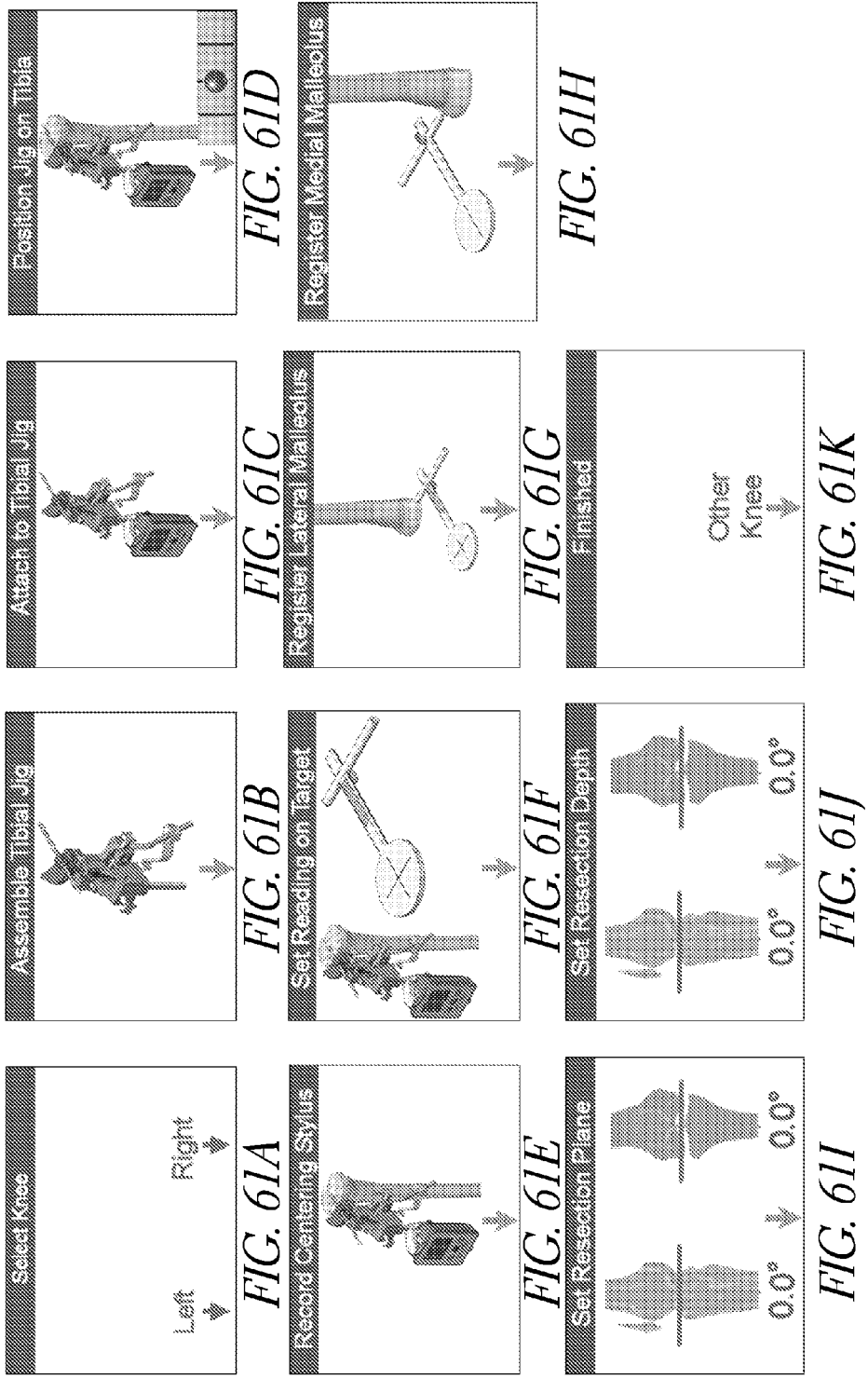

SYSTEMS AND METHODS FOR JOINT REPLACEMENT

CROSS-REFERENCE TO RELATED APPLICATIONS

This application is a continuation from U.S. patent application Ser. No. 12/509,414, filed Jul. 24, 2009, which is incorporated in its entirety by reference herein, which claims benefit under 35 U.S.C. §119(e) to U.S. Provisional Patent Application No. 61/102,754, filed Oct. 3, 2008, U.S. Provisional Patent Application No. 61/135,863, filed Jul. 24, 2008, U.S. Provisional Patent Application No. 61/102,767, filed Oct. 3, 2008, U.S. Provisional Patent Application No. 61/155,093, filed Feb. 24, 2009, U.S. Provisional Patent Application No. 61/104,644, filed Oct. 10, 2008, U.S. Provisional Patent Application No. 61/153,268, filed Feb. 17, 2009, U.S. Provisional Patent Application No. 61/153,257, filed Feb. 17, 2009, U.S. Provisional Patent Application No. 61/153,255, filed Feb. 17, 2009, U.S. Provisional Patent Application No. 61/173,158, filed Apr. 27, 2009, U.S. Provisional Patent Application No. 61/187,632, filed Jun. 16, 2009, and U.S. Provisional Patent Application No. 61/173,159, filed Apr. 27, 2009, each of which is incorporated in its entirety by reference herein.

BACKGROUND OF THE INVENTIONS

1. Field of the Inventions

The present application is directed to systems and methods for joint replacement, in particular to systems and methods for knee joint replacement which utilize a surgical orientation device or devices.

2. Description of the Related Art

Joint replacement procedures, including knee joint replacement procedures, are commonly used to replace a patient's joint with a prosthetic joint component or components. Such procedures often use a system or systems of surgical tools and devices, including but not limited to cutting guides (e.g. cutting blocks) and surgical guides, to make surgical cuts along a portion or portions of the patient's bone.

Current systems and methods often use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and room.

Where such complex and costly system are not used, simple methods are used, such "eyeballing" the alignment of rods with anatomical features, such as leg bones. These simple methods are not sufficiently accurate to reliably align and place implant components and the bones to which such components are attached.

SUMMARY OF THE INVENTIONS

Accordingly, there is a lack of devices, systems and methods that can be used to accurately position components of prosthetic joints without overly complicating the procedures, crowding the medical personnel, and/or burdening the physician of health-care facility with the great cost of complex navigation systems.

In accordance with at least one embodiment, a surgical orientation device for use in a total knee arthroplasty procedure having an associated three-dimensional coordinate reference system can comprise a portable housing configured to connect to a knee bone by way of one or more orthopedic fixtures, a sensor located within the housing, the sensor configured to monitor the orientation of the housing in the three-dimensional coordinate reference system, the sensor further configured to generate orientation data corresponding to the monitored orientation of the surgical orientation device, and wherein the sensor comprises a multi-axis accelerometer. The surgical orientation device can further comprise a display module configured to display one or more angle measurements corresponding to an offset from a flexion-extension angle or a varus-valgus angle of a mechanical axis of the knee joint, and wherein the sensor can be oriented relative to the housing at an acute angle to maximize the sensitivity of the sensor when coupled to a tibia or a femur.

In accordance with another embodiment, an orthopedic orientation system for use in a joint procedure can comprise an orthopedic fixture adapted to be coupled with a knee bone and to be adjustable in multiple degrees of freedom, and a surgical orientation device having an associated three-dimensional coordinate reference system. The device can comprise a portable housing configured to connect to a knee bone by way of the orthopedic fixtures, and a sensor located within the housing, the sensor configured to monitor the orientation of the housing in the three-dimensional coordinate reference system, the sensor further configured to generate orientation data corresponding to the monitored orientation of the surgical orientation device. The surgical orientation device can further comprise an output device configured to inform a user of the orientation of the device relative to a reference plane corresponding to a mechanical axis of the joint, and wherein the sensor can be configured for optimum sensitivity in the range of motion of the orthopedic fixture.

In accordance with at least one embodiment, an orthopedic system for orienting a cutting plane during a joint replacement procedure can comprise a base member attachable to an anterior face of a tibia, at least one adjustment device connected to and moveable relative to the base member, and at least one probe for referencing a plurality of anatomical landmarks, the anatomical landmarks referencing a mechanical axis of the leg. The at least one adjustment device can be moveable in at least one degree of freedom so as to orient a cutting guide relative to a proximal feature of the tibia, such that the cutting guide is oriented at a selected angle relative to the mechanical axis.

In accordance with at least one embodiment, an interactive user interface for aiding a user in performing an orthopedic procedure can be provided, wherein the user interface is displayed on a display associated with a surgical orientation device configured to monitor the orientation of the surgical orientation device in a three-dimensional coordinate reference system and wherein the user interface is configured to perform acts comprising showing the user steps to be performed in the identified orthopedic procedure and guiding the user in performance of the steps. Guiding the user can comprise displaying one or more instructive images related to a first step to be performed in the identified orthopedic procedure, prompting the user to press a user input after performing the first step of the identified orthopedic procedure, receiving a confirmation from the user that the first step of the identified procedure has been performed, and displaying one or more instructive images related to the second step to be performed in the identified orthopedic procedure.

In accordance with another embodiment, a monitoring system can be provided for monitoring an orientation of a surgical orientation device having an associated three-dimensional coordinate reference system during an orthopedic procedure, the orientation system comprising a display having a window and an on-screen graphic, displayed in the window and representing one or more orientation measurements corresponding to an orientation of the surgical orientation device about one or more axes of the three-dimensional coordinate reference system, the one or more orientation measurements generated by a processor.

In accordance with at least one embodiment, a method for preparing a proximal portion of a tibia for receiving a knee implant can comprise coupling an orthopedic fixture with a proximal feature of the patient's leg, connecting a portable surgical orientation device to an adjustment device that is connected to the orthopedic fixture and moveable relative to the leg, moving the adjustment device to move the portable surgical orientation device in response to a prompt from the portable surgical orientation device to orient the orthopedic fixture relative to a mechanical axis of the leg.

In accordance with another embodiment, a method for performing total knee arthroplasty on a knee joint of a patient can comprise preparing a proximal portion of a tibia for receiving a knee implant, including coupling an orthopedic fixture with a proximal portion of the patient's tibia, connecting a portable surgical orientation device to a moveable portion of the orthopedic fixture, moving the moveable portion of the orthopedic fixture to move the portable surgical orientation device in response to a prompt from the portable surgical orientation device to orient a cutting guide at an intended orientation relative to a mechanical axis of the leg, and resecting the proximal tibia along the cutting guide to define a tibial plateau. The method can further comprise preparing a distal portion of a femur for receiving a knee implant, including coupling an orthopedic fixture and the portable surgical orientation device with an anterior surface of a distal portion of the femur, moving at least one of the femur and the tibia in response to a prompt from the portable surgical orientation device to align the femur with the mechanical axis of the leg, securing a cutting guide with an anterior feature of the femur such that the guide is substantially perpendicular to the mechanical axis, and resecting the distal femur.

In accordance with another embodiment, a method of performing an orthopedic procedure can comprise coupling an orthopedic fixture and the portable surgical orientation device with a distal portion of a limb that comprises a portion of a ball-and-socket joint, the portable surgical orientation device including a housing enclosing a sensor and a microprocessor. The method can further comprise activating the sensor within the portable surgical orientation device, such that the sensor outputs a signal indicative of orientation, collecting positional information of the portable surgical orientation device; and determining the location of the mechanical axis of the limb based on the positional information collected.

BRIEF DESCRIPTION OF THE DRAWINGS

FIG. 3B is a perspective view of a second arrangement of the tibial preparation system of FIG. 3A;

FIG. 24 is a perspective view of a landmark acquisition assembly according to one embodiment that can be used in the tibial preparation system of FIG. 3A;

FIGS. 30-36B are perspective views of the second arrangement of the tibial preparation system of FIG. 3B during a knee joint replacement procedure;

FIGS. 58A-61K show screen displays generated by one embodiment of the interactive user interface of the surgical orientation device of FIG. 7.

DETAILED DESCRIPTION OF THE PREFERRED EMBODIMENT

Although certain preferred embodiments and examples are disclosed below, it will be understood by those skilled in the art that the inventive subject matter extends beyond the specifically disclosed embodiments to other alternative embodiments and/or uses of the invention, and to obvious modifications and equivalents thereof. Thus it is intended that the scope of the inventions herein disclosed should not be limited by the particular disclosed embodiments described below. Thus, for example, in any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

In addition, in the following description of the invention, a "module" includes, but is not limited to, software or hardware components which perform certain tasks. Thus, a module may include object-oriented software components, class components, procedures, subroutines, data structures, segments of program code, drivers, firmware, microcode, circuitry, data, tables, arrays, etc. Those with ordinary skill in the art will also recognize that a module can be implemented using a wide variety of different software and hardware techniques.

The following sections describe in detail systems and methods for a total knee joint replacement procedure. The knee joint often requires replacement in the form of prosthetic components due to strain, stress, wear, deformation, misalignment, and/or other conditions in the joint. Prosthetic knee joint components are designed to replace a distal portion or portions of a femur and/or a proximal portion or portions of a tibia.

Figure 1:
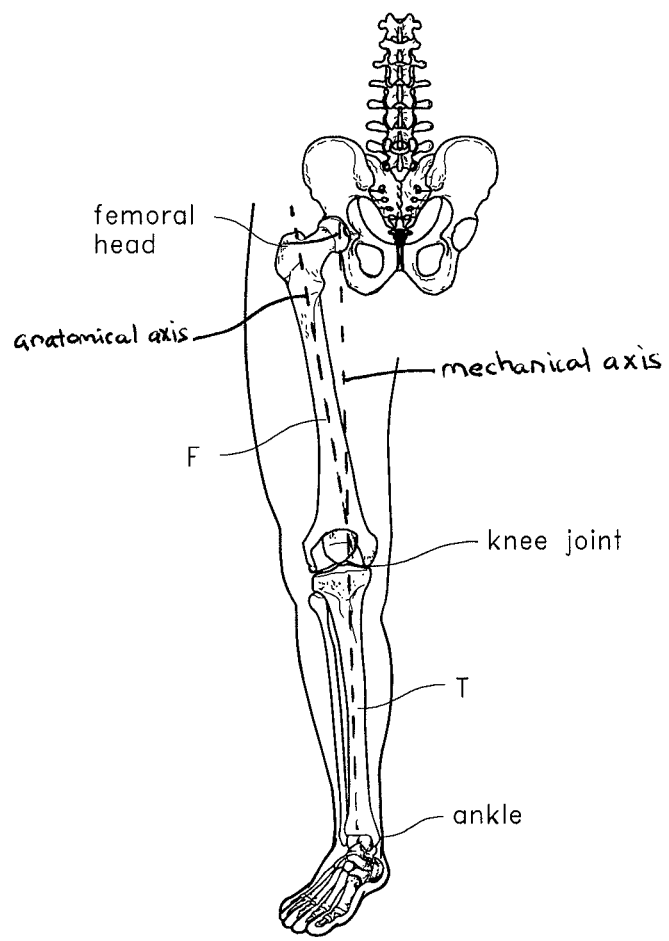
FIG. 1 shows a representation of a human leg, identifying the femoral head, knee joint, femur, tibia, and ankle.

FIG. 1 illustrates a femur F and tibia T, with the distal portion of the femur F and proximal portion of the tibia T forming the knee joint. To provide the reader with the proper orientation of the instruments and to assist in more fully understanding the construction of the instruments, a small chart is included on many of the figures. The charts indicate the general directions—anterior, posterior, medial, and lateral, as well as proximal and distal. These terms relate to the orientation of the knee bones, such as the femur and tibia and will be used in the descriptions of the various instruments consistent with their known medical usage. Additionally, the terms varus/valgus and posterior/anterior are used herein to describe directional movement. Varus/valgus is a broad term as used herein, and includes, without limitation, rotational movement in a medial and/or lateral direction relative to the knee joint shown in FIG. 1. Posterior/anterior is a broad term as used herein, and includes, without limitation, rotational movement in a posterior and/or anterior direction (e.g. in a flexion/extension direction) relative to the knee joint shown in FIG. 1.

Prior to replacing the knee joint with prosthetic components, surgical cuts commonly called resections are generally made with a cutting tool or tools along a portion or portions of both the proximal tibia and distal femur. These cuts are made to prepare the tibia and femur for the prosthetic components. After these cuts are made, the prosthetic components can be attached and/or secured to the tibia and femur.

The desired orientation and/or position of these cuts, and of the prosthetic components, can be determined pre-operatively and based, for example, on a mechanical axis running through an individual patient's leg. Once the desired locations of these cuts are determined pre-operatively, the surgeon can use the systems and methods described herein to make these cuts accurately. While the systems and methods are described in the context of a knee joint replacement procedure, the systems and/or their components and methods can similarly be used in other types of medical procedures, including but not limited to shoulder and hip replacement procedures.

I. Overview of Systems and Methods

FIGS. 2-6 show various systems which can be used in orthopedic procedures, such as joint replacement procedures. Such systems can include a tibial preparation system 10, a femoral preparation system 510, and a knee distraction and femoral preparation system 610. As described below, each of these systems can be embodied in a number of variations with different advantages.

II. Tibial Preparation Systems and Methods

A number of different tibial preparation systems are discussed below. These systems are useful for modifying the natural tibia to enable it to have a prosthetic component securely mounted upon it.

A. Tibial Preparation System with Target Probes

Figure 2A:
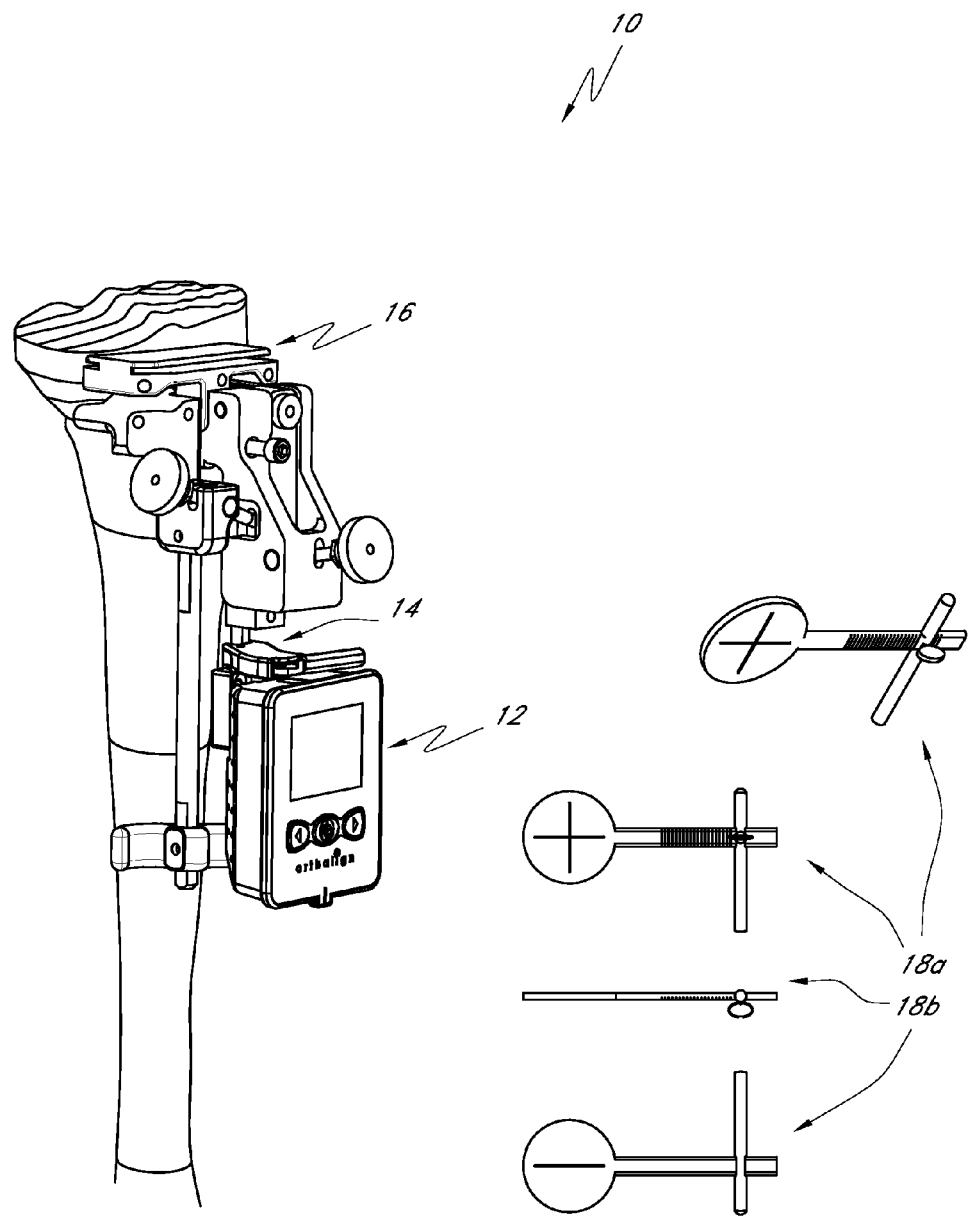
FIG. 2A is a perspective view of a tibial preparation system according to one embodiment that can be used in connection with preparation of an aspect of a knee joint during a knee joint replacement procedure.

With reference to FIG. 2a, a tibial preparation system 10 can comprise a surgical orientation device 12, or other measuring device, which can be used to measure and record the location of anatomical landmarks of use in a total knee procedure, such as the location of the mechanical axis of the leg. The mechanical axis of the leg, as defined herein, generally refers to an axial line extending from the center of rotation of a proximal head of a femur (e.g. the center of the femoral head) through the center of the knee, to a center, or mid-point, of the ankle (see, for example, FIG. 1). Generally, an ideal mechanical axis in a patient allows load to pass from the center of the hip, through the center of the knee, and to the center of the ankle. The tibial preparation system 10 also can include a coupling device 14, a universal jig 16, and target probes 18a, 18b.

As used herein, the term "universal jig" is a broad term and includes, without limitation, orthopedic fixtures that are adapted to be connected to or coupled with, directly or indirectly, an anatomical structure, such as a bone, a limb, a portion of a joint, and to be moveable in one or more degrees of freedom, and in some cases is multiple degrees of freedom. As discussed further below, the universal jig 16 can be one form of an orthopedic fixture that can be used to couple the surgical orientation device 12 with a bone adjacent to a knee joint. In certain techniques discussed below the surgical orientation device 12 is used with a plurality of orthopedic fixtures. The coupling device 14 advantageously enables the surgical orientation device 12 to be quickly coupled and decoupled with a variety of orthopedic fixtures during the procedure. This enables the surgical orientation device 12 to be used in a modular fashion, with a variety of orthopedic fixtures at one or more stages of a procedure.

1. Surgical Orientation Device for Verifying Alignment of Orthopedic Fixtures

Figure 7:
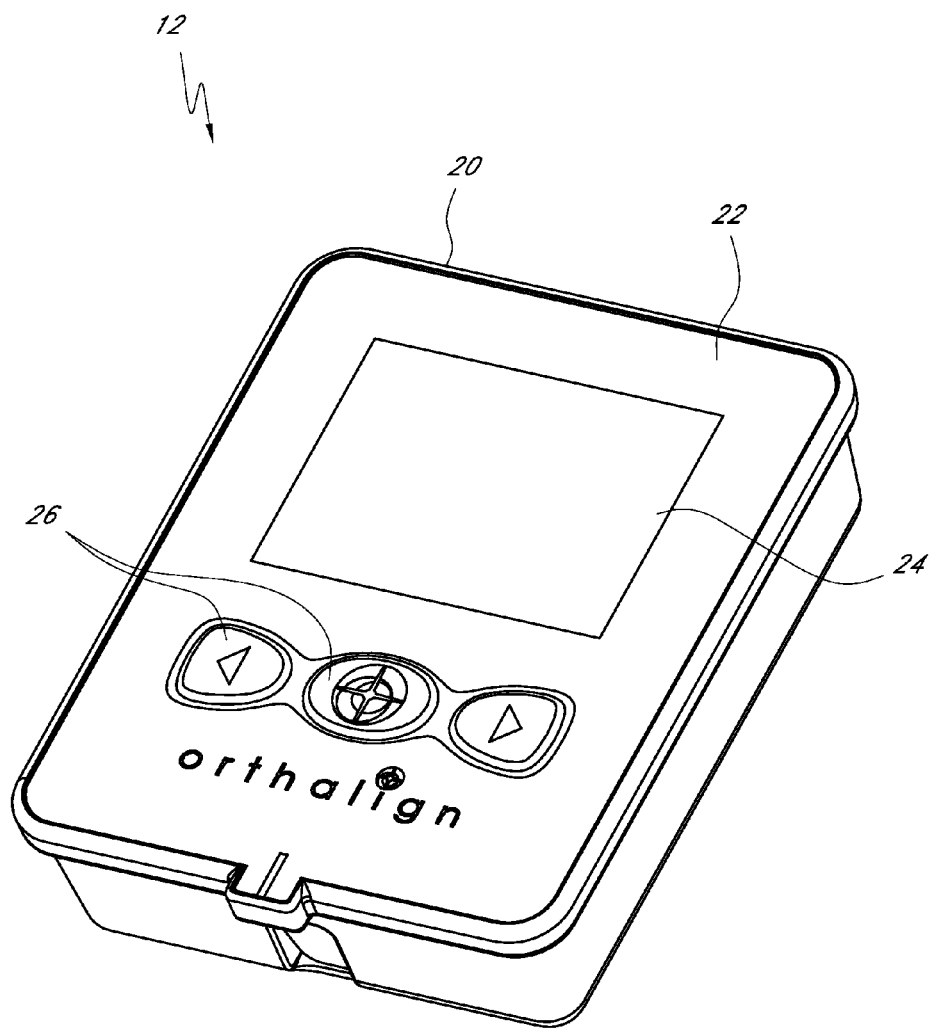
FIG. 7 is a perspective view of a surgical orientation device according to one embodiment that can be used for orienting a resection plane or planes.

A surgical orientation device can be provided which can be used for verifying an alignment of an orthopedic fixture or fixtures, or a cutting plane or planes, during an orthopedic procedure. Surgical orientation device is a broad term as used herein, and includes, without limitation, devices which can be used alone or in conjunction with an orthopedic fixture or fixtures to orient a cutting plane during an orthopedic procedure or to otherwise identify or track a relative position of one or more surgical devices or anatomical structures, and can encompass any of the embodiments shown in the drawings and as described herein. For example, FIG. 7 shows an embodiment of a surgical orientation device 12. The surgical orientation device 12 can comprise a compact, generally hand-held and/or portable device for use in orienting a cutting guide or other surgical tool in a joint replacement procedure. The surgical orientation device 12 can be used to locate a portion of the mechanical axis that extends through the lower tibia or a portion thereof. Also, the surgical orientation device 12 can be used to locate a portion of the mechanical axis that extends through the femur or a portion thereof. In certain techniques discussed below, the surgical orientation device 12 is used to locate one, two, or more planes intersecting the mechanical axis. The surgical orientation device 12, as described herein, can be used alone or in conjunction with other devices, components, and/or systems.

In a preferred arrangement, the surgical orientation device 12 can comprise a generally rectangular-shaped, box-like structure having an outer housing 20. The outer housing 20 can be portable. The outer housing 20 can be comprised, at least in part, of plastic including but not limited to ABS, polycarbonate, or other suitable material. The surgical orientation device 12 can be configured for hand-held use.

With continued reference to FIG. 7, a front side 22, or a portion of the front side 22, of the surgical orientation device 12 can comprise a display 24. The display 24 can be a separate component from the outer housing 20 or can be integrated on or within the outer housing 20. The display 24 can comprise an output device. For example, the display 24 can comprise a liquid crystal display ("LCD") or Ferroelectric Liquid Crystal on Silicon ("FLCOS") display screen. The display screen can be sized such that a user can readily read numbers, lettering, and/or symbols displayed on the display screen while performing a medical procedure. In an embodiment, the display 24 comprises a Quarter Video Graphics Array ("QVGA") Thin Film Transistor ("TFT") LCD screen. Other types of display screens can also be used, as can other shapes, sizes, and locations for the display 24 on the surgical orientation device 12.

The surgical orientation device 12 can further comprise at least one user input device 26. The at least one user input device 26 can comprise a plurality of buttons located adjacent the display 24. The buttons can be activated, for example, by a finger, hand, and/or instrument to select a mode or modes of operation of the device 12, as discussed further below. In a preferred arrangement, the at least one user input comprises three buttons located underneath the display 24 as illustrated in FIG. 7. In other embodiments, the user input device 26 is a separate component from the housing 20. For example, the user input device 26 can comprise a remote input device coupled to the surgical orientation device 12 via a wired or wireless connection. In yet other embodiments, the user input device 26 comprises a microphone operating in conjunction with a speech recognition module configured to receive and process verbal instructions received from a user.

As discussed below in connection with Figures ***, the surgical orientation device 12 includes a user interface with which a clinician can interact during a procedure. In one embodiment, the display 24 and at least one user input 26 can form a user interface. The user interface allows a surgeon, medical personnel, and/or other user to operate the surgical orientation device 12 with ease, efficiency, and accuracy. Specific examples and illustrations of how the user interface can operate in conjunction with specific methods are disclosed further herein.

Figure 8:
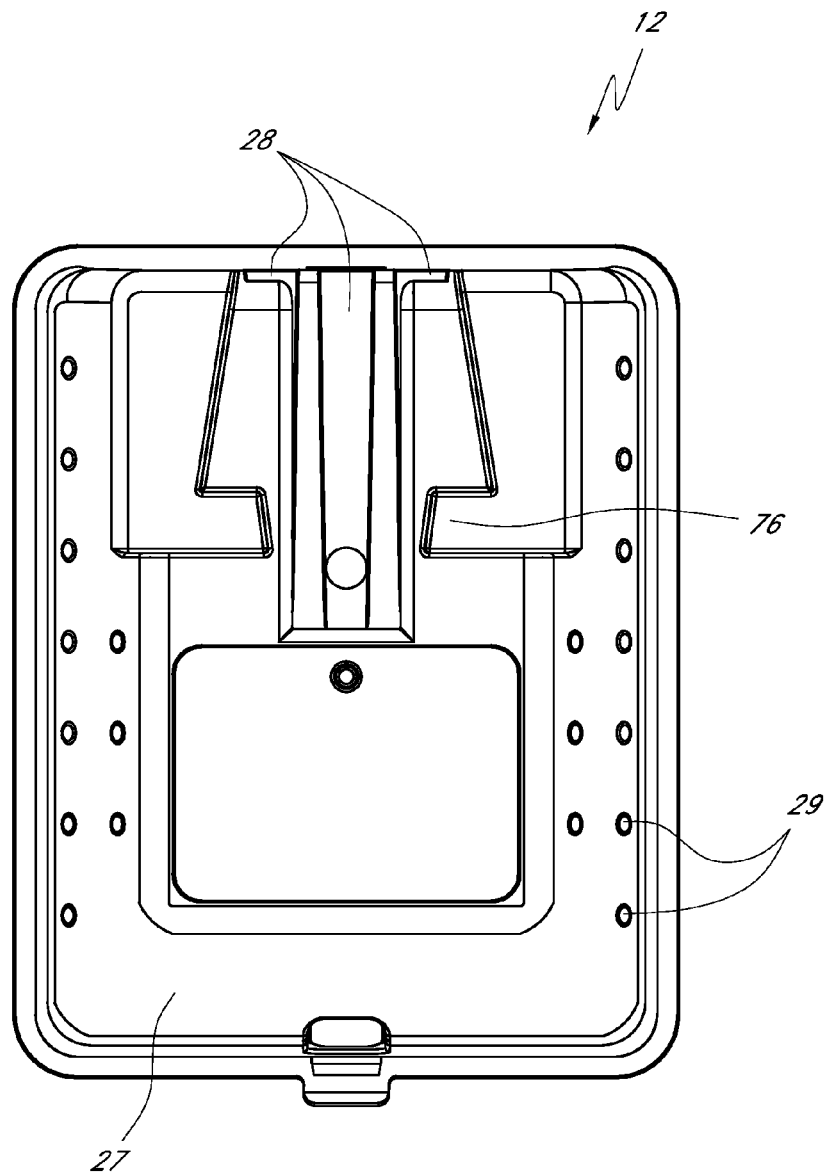
FIG. 8 is a back view of the surgical orientation device of FIG. 7.
Figure 9:
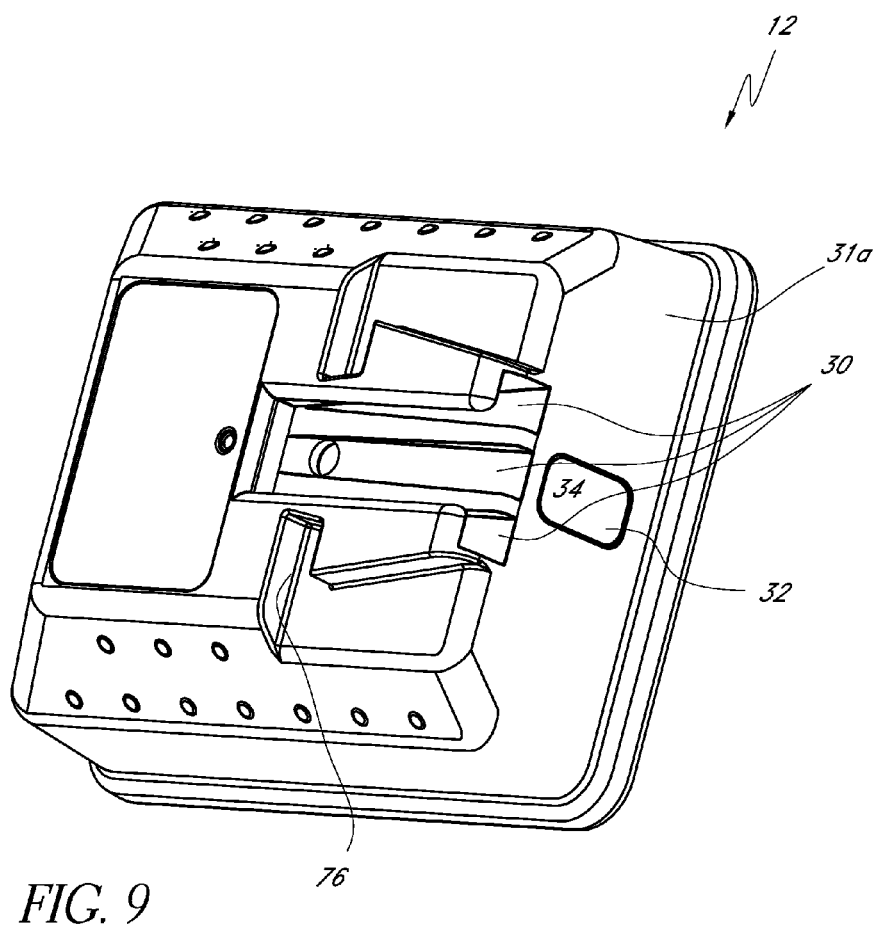
FIG. 9 is a perspective view of the surgical orientation device of FIG. 7.

FIGS. 8 and 9 show a back side 27 of the surgical orientation device 12. The back side 27 can include an attachment structure or structures 28, as well as a gripping feature or features 29 for facilitating handling of the surgical orientation device 12. The attachment structures 28 can facilitate attachment of the surgical orientation device 12 to another device, such as for example the coupling device 14. In a preferred arrangement, the attachment structures 28 comprise grooves, or channels 30, along a portion of the back side of the surgical orientation device 12.

Figure 10A:
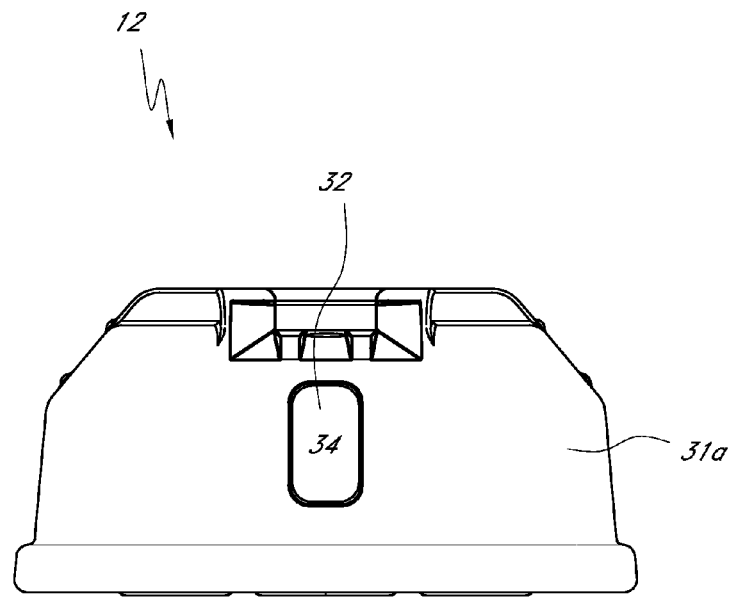
FIG. 10A is a top view of the surgical orientation device of FIG. 7.
Figure 10B:
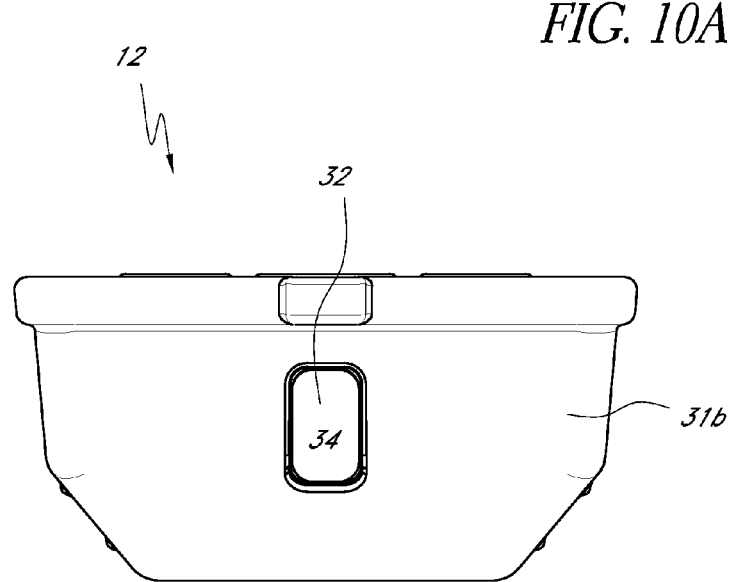
FIG. 10B is a bottom view of the surgical orientation device of FIG. 7.

The attachment structures 28 can be formed, for example, from protruding portions of the back side of the surgical orientation device 12, and can extend partially, or entirely, along the back side of the surgical orientation device 12. The attachment structures 28 can receive corresponding, or mating, structures from the coupling device 14, so as to couple, or lock, the coupling device 14 to the surgical orientation device 12. FIGS. 10A and 10B show top and bottom sides 31a, 31b of the surgical orientation device 12. The surgical orientation device 12 can comprise optical components 32 that can be located on the top side 31a, the bottom side 31b, or the top and bottom sides 31a, 31b of the surgical orientation device 12. The optical components 32 can comprise transparent windows 34 integrated into the surgical orientation device 12. The optical components 32 can be windows that permit visible light (e.g. laser light) to emit from the top side 31a, the bottom side 31b, or both the top and bottom sides 31a, 31b of the surgical orientation device 12. While the embodiment illustrated in FIGS. 10a and 10b shows two windows 34 for transmitting light, other numbers are also possible. Additionally, while the optical components 32 are shown located on the top and bottom of the surgical orientation device 12, in other embodiments the optical components 32 can be located in other positions and/or on other portions of the surgical orientation device 12.

Figure 11:
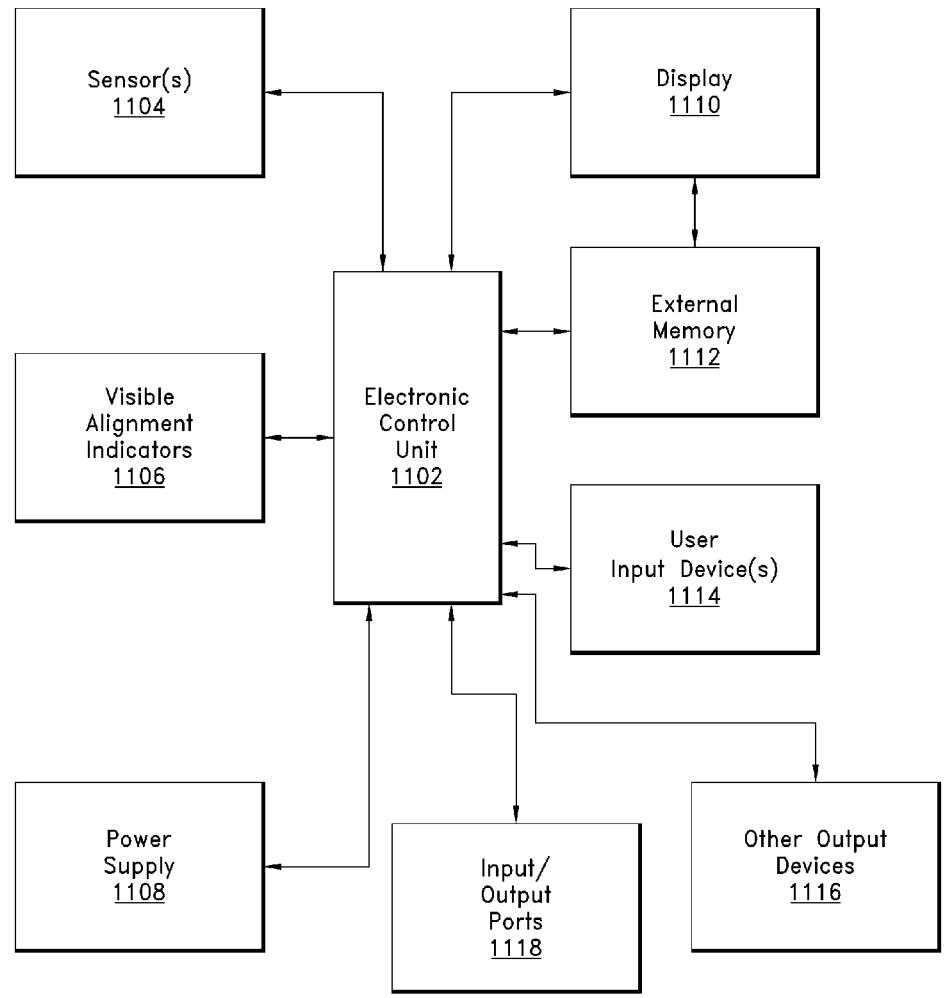
FIG. 11 is a block diagram of an electrical system of the surgical orientation device of FIG. 7.

FIG. 11 illustrates a high-level block diagram of an electrical system 1100 of the surgical orientation device 12. The electrical system 1100 comprises an electronic control unit 1102 that communicates with one or more sensor(s) 1104, one or more visible alignment indicators 1106, a power supply 1108, a display 1110, external memory 1112, one or more user input devices 1114, other output devices 1116 and/or one or more input/output ("I/O") ports 1118.

In general, the electronic control unit 1102 receives input from the sensor(s), the external memory 1112, the user input devices 1114 and/or the I/O ports 1118 and controls and/or transmits output to the visible alignment indicators 1106, the display 1110, the external memory 1112, the other output devices 1116 and/or the I/O ports 1118. The electronic control unit 1102 can be configured to receive and send electronic data, as well as perform calculations based on received electronic data. In certain embodiments, the electronic control unit 1102 can be configured to convert the electronic data from a machine-readable format to a human readable format for presentation on the display 1110. The electronic control unit 1102 comprises, by way of example, one or more processors, program logic, or other substrate configurations representing data and instructions, which operate as described herein. In other embodiments, the electronic control unit 1102 comprises controller circuitry, processor circuitry, processors, general purpose single-chip or multi-chip microprocessors, digital signal processors, embedded microprocessors, microcontrollers and/or the like. The electronic control unit 1102 can have conventional address lines, conventional data lines, and one or more conventional control lines. In yet other embodiments, the electronic control unit 1102 comprises an application-specific integrated circuit (ASIC) or one or more modules configured to execute on one or more processors. In certain embodiments, the electronic control unit 1102 comprises an AT91SAM7SE microcontroller available from Atmel Corporation.

The electronic control unit 1102 can communicate with internal memory and/or the external memory 1112 to retrieve and/or store data and/or program instructions for software and/or hardware. The internal memory and the external memory 1112 can include random access memory ("RAM"), such as static RAM, for temporary storage of information and/or read only memory ("ROM"), such as flash memory, for more permanent storage of information. In some embodiments, the external memory 1112 includes an AT49BV160D-70TU Flash device available from Atmel Corporation and a CY62136EV30LL-45ZSXI SRAM device available from Cypress Semiconductor Corporation. The electronic control unit 1102 can communicate with the external memory 1112 via an external memory bus.

In general, the sensor(s) can be configured to provide continuous real-time data to the surgical orientation device 12. The electronic control unit 1102 can be configured to receive the real-time data from the sensor(s) 1104 and to use the sensor data to determine, estimate, and/or calculate an orientation or position of the surgical orientation device 12. The orientation information can be used to provide feedback to a user during the performance of a surgical procedure, such as a total knee joint replacement surgery, as described in more detail herein.

In some arrangements, the one or more sensors 1104 can comprise at least one orientation sensor configured to provide real-time data to the electronic control unit 1102 related to the motion, orientation, and/or position of the surgical orientation device 12. For example, the sensor module 1104 can comprise at least one gyroscopic sensor, accelerometer sensor, tilt sensor, magnetometer and/or other similar device or devices configured to measure, and/or facilitate determination of, an orientation of the surgical orientation device 12. In some embodiments, the sensors 1104 can be configured to provide measurements relative to a reference point(s), line(s), plane(s), and/or gravitational zero. Gravitational zero, as referred to herein, refers generally to an orientation in which an axis of the sensor is perpendicular to the force of gravity, and thereby experiences no angular offset, for example tilt, pitch, roll, or yaw, relative to a gravitational force vector. In other embodiments, the sensor(s) 1104 can be configured to provide measurements for use in dead reckoning or inertial navigation systems.

In various embodiments, the sensor(s) 1104 comprise one or more accelerometers that measure the static acceleration of the surgical orientation device 12 due to gravity. For example, the accelerometers can be used as tilt sensors to detect rotation of the surgical orientation device 12 about one or more of its axes. The one or more accelerometers can comprise a dual axis accelerometer (which can measure rotation about two axes of rotation) or a three-axis accelerometer (which can measure rotation about three axes of rotation). The changes in orientation about the axes of the accelerometrs can be determined relative to gravitational zero and/or to a reference plane registered during a tibial or femoral preparation procedure as described herein.

In certain embodiments, a multi-axis accelerometer (such as the ADXL203CE MEMS accelerometer available from Analog Devices, Inc. or the LIS331DLH accelerometer available from ST Microelectronics.) detects changes in orientation about two axes of rotation. For example, the multi-axis accelerometer can detect changes in angular position from a horizontal plane (e.g., anterior/posterior rotation) of the surgical orientation device 12 and changes in angular position from a vertical plane (e.g., roll rotation) of the surgical orientation device 12. The changes in angular position from the horizontal and vertical planes of the surgical orientation device 12 (as measured by the sensor 1104 can also be used to determine changes in a medial-lateral orientation (e.g., varus/valgus rotation) of the surgical orientation device 12.

In some arrangements, the sensors 1104 comprise at least one single- or multi-axis gyroscope sensor and at least one single- or multi-axis accelerometer sensor. For example, the sensor module 1104 can comprise a three-axis gyroscope sensor (or three gyroscope sensors) and a three-axis accelerometer (or three accelerometer sensors) to provide positional and orientational measurements for all six degrees of freedom of the surgical orientation device 12. In some embodiments, the sensors provide an inertial navigation or dead reckoning system to continuously calculate the position, orientation, and velocity of the surgical orientation device 12 without the need for external references In some embodiments, the sensors 1104 comprise one or more accelerometers and at least one magnetometer. The magnetometer can be configured to measure a strength and/or direction of one or more magnetic fields in the vicinity of the surgical orientation device 12. The magnetometer can advantageously be configured to detect changes in angular position about a horizontal plane. In other embodiments, the sensors 1104 comprise one or more sensors capable of determining distance measurements. For example a sensor located in the surgical orientation device 12 can be in electrical communication (wired or wireless) with an emitter element mounted at the end of a measurement probe. In certain embodiments, the electrical control unit can be configured to determine the distance between the sensor and emitter (for example, an axial length of a measurement probe corresponding to a distance to an anatomical landmark, such as a malleolus).

In other embodiments, the one or more sensors 1104 comprise a temperature sensor to monitor system temperature of the electrical system 1100. Operation of some of the electrical components can be affected by changes in temperature. The temperature sensor can be configured to transmit signals to the electronic control unit 1102 to take appropriate action. In addition, monitoring the system temperature can be used to prevent overheating. In some embodiments, the temperature sensor comprises a NCP21WV103J03RA thermistor available from Murata Manufacturing Co. The electrical system 1100 can further include temperature, ultrasonic and/or pressure sensors for measuring properties of biological tissue and other materials used in the practice of medicine or surgery, including determining the hardness, rigidity, and/or density of materials, and/or determining the flow and/or viscosity of substances in the materials, and/or determining the temperature of tissues or substances within materials.

In certain embodiments, the sensors 1104 facilitate determination of an orientation of the surgical orientation device 12 relative to a reference orientation established during a preparation and alignment procedure performed during orthopedic surgery. Further details regarding the operation of the sensors in conjunction with a total knee replacement surgery will be discussed below.

The one or more sensors 1104 can form a component of a sensor module that comprises at least one sensor, signal conditioning circuitry, and an analog-to-digital converter ("ADC"). In certain embodiments, the components of the sensor module 1104 are mounted on a stand-alone circuit board that is physically separate from, but in electrical communication with, the circuit board(s) containing the other electrical components described herein. In other embodiments, the sensor module is physically integrated on the circuit board(s) with the other electrical components. The signal conditioning circuitry of the sensor module can comprise one or more circuit components configured to condition, or manipulate, the output signals from the sensor(s) 1104. In certain embodiments, the signal conditioning circuitry comprises filtering circuitry and gain circuitry. The filtering circuitry can comprise one more filters, such as a low pass filter. For example, a 10 Hz single pole low pass filter can be used to remove vibrational noise or other low frequency components of the sensor output signals. The gain circuitry can comprise one or more operational amplifier circuits that can be used to amplify the sensor output signals to increase the resolution potential of the sensor. For example, the operational amplifier circuit can provide gain such that a 0 g output results in a midrange (e.g., 1.65 V signal), a +1 g output results in a full scale (e.g., 3.3 V) signal and a −1 g output results in a minimum (0 V) signal to the ADC input.

In general, the ADC of the sensor module can be configured to convert the analog output voltage signals of the sensor(s) 1104 to digital data samples. In certain embodiments, the digital data samples comprise voltage counts. The ADC can be mounted in close proximity to the sensor to enhance signal to noise performance. In certain embodiments, the ADC comprises an AD7921 two channel, 12-bit, 250 Kiloseconds per Sample ADC. In an arrangement having a 12-bit ADC can generate 4096 voltage counts. The ADC can be configured to interface with the electronic control unit 1102 via a serial peripheral interface port of the electronic control unit 1102. In other embodiments, the electronic control unit 1102 comprises an on-board ADC that can be used to convert the sensor output signals into digital data counts.

With continued reference to FIG. 11, the visible alignment indicators 1106 can comprise one or more lasers, which can be configured to project laser light through the optical component or components 32 described above. For example, the visible alignment indicators 1106 can comprise a forward laser and an aft laser. The laser light can be used to project a point, a plane, and or a cross-hair onto a target or targets, including but not limited to an anatomical feature or landmark, to provide alternative or additional orientation information to a surgeon regarding the orientation of the orientation device 12. For example, laser light can be used to project a plane on a portion of bone to indicate a resection line and a cross-hair laser pattern can be used to ensure alignment along two perpendicular axes. In certain embodiments, the visible alignment indicators 1106 can be used to determine a distance to an anatomical feature or landmark (for example, a laser distance measurement system). For example, the electronic control unit 1102 can project laser light to a target and a sensor 1104 within the surgical orientation device can sense the laser light reflected back from the target and communicate the information to the electronic control unit. The electronic control unit 1102 can then be configured to determine the distance to the target. The lasers can be controlled by the electronic control unit 1102 via pulse width modulation ("PWM") outputs. In certain embodiments, the visible alignment indicators 1106 comprise Class 2M lasers. In other embodiments, the visible alignment indicators 1106 comprises other types of lasers or light sources.

The power supply 1108 can comprise one or more power sources configured to supply DC power to the electronic system 1100 of the surgical orientation device 12. In certain embodiments, the power supply 1108 comprises one or more rechargeable or replaceable batteries and/or one or more capacitive storage devices (for example, one or more capacitors or ultracapacitors). In other embodiments, power can be supplied by other wired and/or wireless power sources. In preferred arrangements, the power supply 1108 comprises two AA alkaline, lithium, or rechargeable NiMH batteries. The surgical orientation device 12 can also include a DC/DC converter to boost the DC power from the power supply to a fixed, constant DC voltage output (e.g., 3.3 volts) to the electronic control unit 1102. In some embodiments, the DC/DC converter comprises a TPS61201DRC synchronous boost converter available from Texas Instruments. The electronic control unit 1106 can be configured to monitor the battery level if a battery is used for the power supply 1108. Monitoring the battery level can advantageously provide advance notice of power loss. In certain embodiments, the surgical orientation device 12 can comprise a timer configured to cause the surgical orientation device 12 to temporarily power off after a predetermined period of inactivity and/or to permanently power off after a predetermined time-out period.

As discussed above, the display 1110 can comprise an LCD or other type screen display. The electronic control unit 1102 communicates with the display via the external memory bus. In certain embodiments, the electronic system 1100 comprises a display controller and/or an LED driver and one or more LEDs to provide backlighting for the display 1110. For example, the display controller can comprise an LCD controller integrated circuit ("IC") and the LED driver can comprise a FAN5613 LED driver available from Fairchild Semiconductor International, Inc. The electronic control unit 1102 can be configured to control the LED driver via a pulse width modulation port to control the brightness of the LED display. For example, the LED driver can drive four LEDs spaced around the display screen to provide adequate backlighting to enhance visibility. The display can be configured to display one or more on-screen graphics. The on-screen graphics can comprise graphical user interface ("GUI") images or icons. The GUI images can include instructive images, such as illustrated surgical procedure steps, or visual indicators of the orientation information received from the sensor(s) 1104. For example, the display can be configured to display degrees and either a positive or negative sign to indicate direction of rotation from a reference plane and/or a bubble level indicator to aid a user in maintaining a particular orientation. The display can also be configured to display alphanumeric text, symbols, and/or arrows. For example, the display can indicate whether a laser is on or off and/or include an arrow to a user input button with instructions related to the result of pressing a particular button.

With continued reference to FIG. 11, the user input device(s) 1114 can comprise buttons, switches, a touchscreen display, a keyboard, a joystick, a scroll wheel, a trackball, a remote control, a microphone, and the like. The user input devices 1114 can allow the user to enter data, make selections, input instructions or commands to the surgical orientation device 12, verify a position of the surgical orientation device 12, turn the visible alignment indicators 1106 on and off, and/or turn the entire surgical orientation device 12 on and off. The other user output devices 1116 (i.e. other than the display 1110) can comprise an audio output, such as a speaker, a buzzer, an alarm, or the like. For example, the audio output can provide a warning to the user when a particular condition occurs. The output devices 1116 can also comprise a visible output, such as one or more LED status or notification lights (for example, to indicate low battery level, an error condition, etc.). The audio output can comprise different patterns, tones, cadences, durations, and/or frequencies to signify different conditions or events. In other embodiments, output from the electronic control unit 1102 can be sent to external display devices, data storage devices, servers, and/or other computing devices (e.g., via a wireless network communication link).

The I/O ports 1118 of the electronic control unit 1102 can comprise a JTAG port and one or more serial communication ports. The JTAG port can be used to debug software installed on the electronic control unit 1102 during testing and manufacturing phases. The JTAG port can be configured such that it is not externally accessible post-manufacture. The serial communication ports can include a Universal Serial Bus ("USB") port and/or one or more universal asynchronous receiver/transmitters ("UART") ports. At least one of the UART ports can be accessible externally post-manufacture. The external UART port can be an infrared ("IR") serial port in communication with an infrared ("IR") transceiver. The IR serial port can be used to update the software installed on the electronic control unit 1102 post-manufacture and/or to test the operation of the electronic control unit 1102 by outputting data from the electronic control unit 1102 to an external computing device via an external wireless connection. Other types of I/O ports are also possible.

Figure 12A:
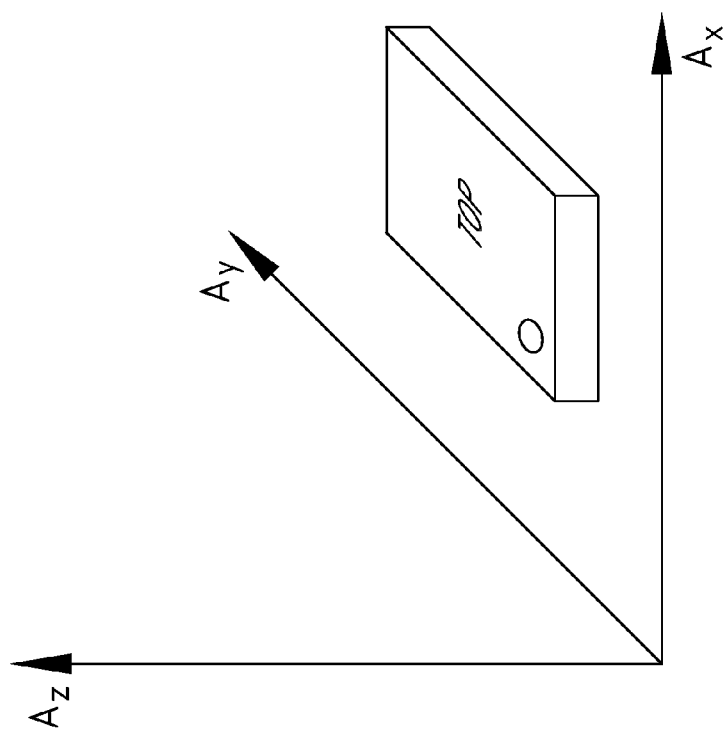
FIGS. 12A-12C illustrate operation of accelerometers according to embodiments that can be used as sensors in the electrical system of FIG. 11.

As described above, the sensor(s) 1104 can comprise one or more accelerometers. Accelerometers can measure the static acceleration of gravity in one or more axes to measure changes in tilt orientation. For example, a three-axis accelerometer can measure the static acceleration due to gravity along three orthogonal axes, as illustrated in FIG. 12A. A two-axis accelerometer can measure the static acceleration due to gravity along two orthogonal axes (for example, the x and y axes of FIG. 12A). The output signals of an accelerometer can comprise analog voltage signals. The output voltage signals for each axis can fluctuate based on the fluctuation in static acceleration as the accelerometer changes its orientation with respect to the gravitational force vector. In certain embodiments, an accelerometer experiences static acceleration in the range from −1 g to +1 g through 180 degrees of tilt (with −1 g corresponding to a −90 degree tilt, 0 g corresponding to a zero degree tilt, and +1 g corresponding to a +90 degree tilt. The acceleration along each axis can be independent of the acceleration along the other axis or axes.

Figure 12B:
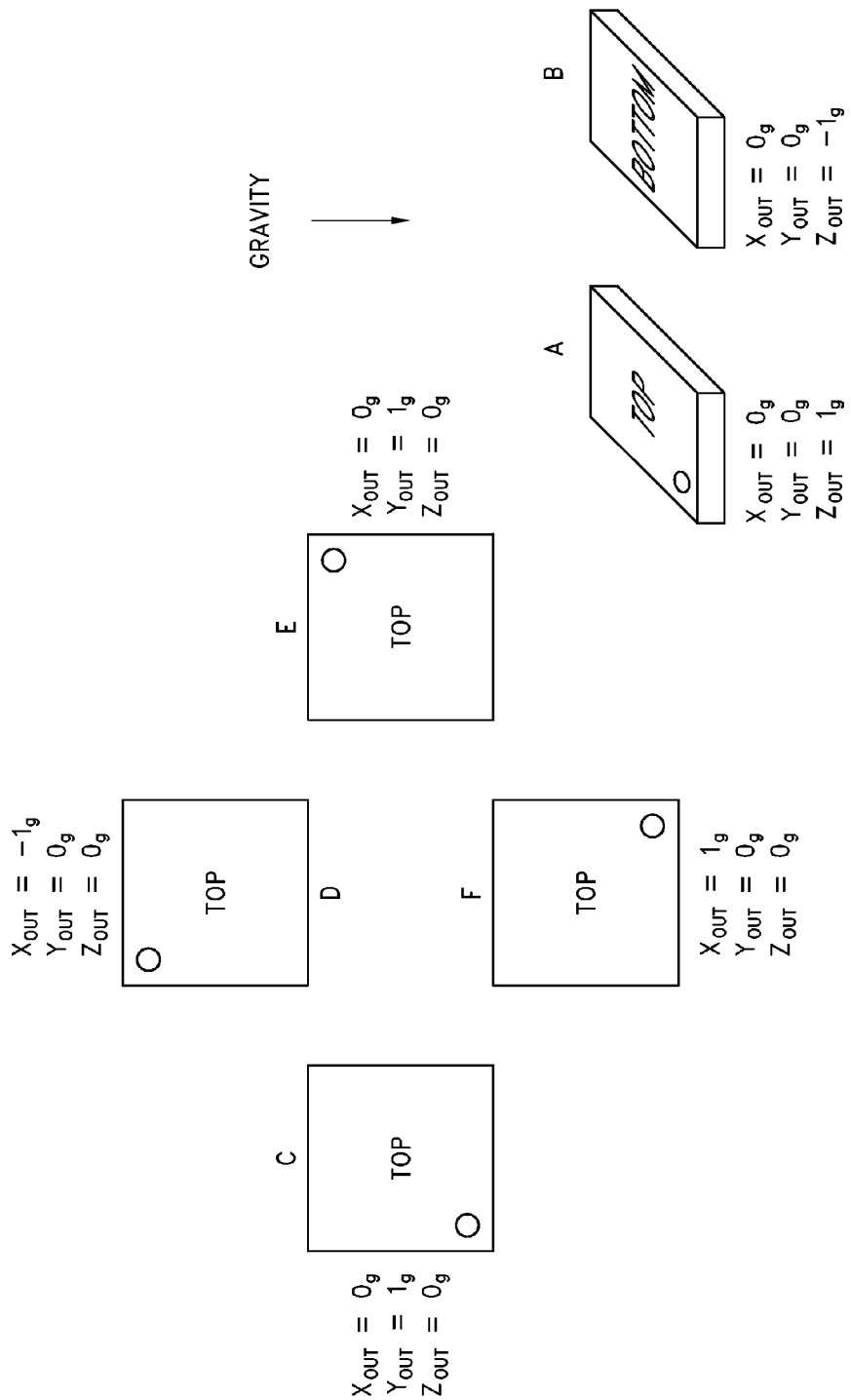

FIG. 12B illustrates a measured acceleration along each of the three axes of a three-axis accelerometer in six different orientation positions. TOP and BOTTOM labels, as well as a circle indicating Pin 1 of the accelerometer, have been included to aid in determining the various orientations. A gravitational force reference vector is illustrated as pointing straight down toward the Earth's surface. At positions A and B, the x-axis and the y-axis of the accelerometer are perpendicular to the force of gravity and the z-axis of the accelerometer is parallel to the force of gravity; therefore, the x and y acceleration components of static acceleration due to gravity at positions A and B are 0 g and the z component of static acceleration due to gravity at positions A and B is +1 g and −1 g, respectively. At positions C and E, the x-axis and the z-axis of the accelerometer are perpendicular to the force of gravity and the y-axis is parallel to the force of gravity; therefore, the x and z acceleration components of static acceleration due to gravity at positions C and E are 0 g and the y component of static acceleration due to gravity at positions C and E is +1 g and −1 g, respectively. At positions D and F, the y-axis and z-axis are perpendicular to the force of gravity and the x-axis is parallel to the force of gravity; therefore, the y and z acceleration components of static acceleration due to gravity at positions D and F are 0 g and the x component of static acceleration due to gravity at positions D and F is +1 g and −1 g, respectively. A dual-axis accelerometer operates in the same manner but without the z component. In certain arrangements, a three-axis accelerometer can be used as a tiltmeter to measure changes in orientation about two axes.

Figure 12C:
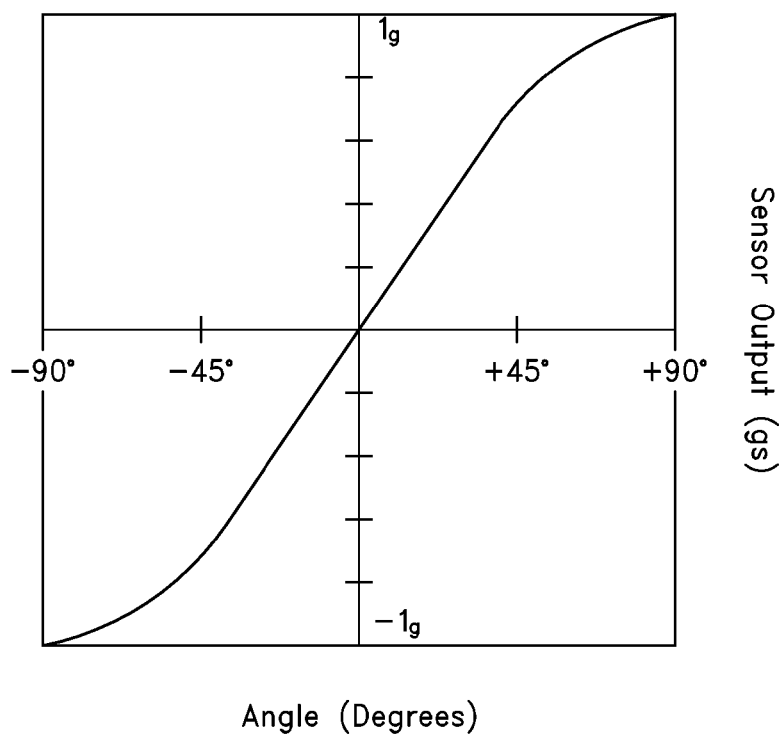

Multi-axis accelerometers can be conceptualized as having a separate accelerometer sensor for each of its axes of measurement, with each sensor responding to changes in static acceleration in one plane. In certain embodiments, each accelerometer sensor is most responsive to changes in tilt (i.e., operates with maximum or optimum accuracy and/or resolution) when its sensitive axis is substantially perpendicular to the force of gravity (i.e., when the longitudinal plane of the accelerometer sensor is parallel to the force of gravity) and least responsive when the sensitive axis is parallel to the force of gravity (i.e., when the longitudinal plane of the accelerometer sensor is perpendicular to the force of gravity). FIG. 12C illustrates the output of the accelerometer in g's as it tilts from −90 degrees to +90 degrees. As shown, the tilt sensitivity diminishes between −90 degrees and −45 degrees and between +45 degrees and +90 degrees (as shown by the decrease in slope). This resolution problem at the outer ranges of tilt motion makes the measurements much less accurate for tilt measurements over 45 degrees. In certain embodiments, when the mounting angle of the surgical orientation device 12 is known, the sensor(s) 1104 can be mounted to be offset at an angle such that the accelerometer sensors can operate in their more accurate, steeper slope regions. For example, for use during the knee surgery preparation procedures described herein, the sensor(s) 1104 can be mounted at approximately a 22-degree angle relative to the anterior-posterior axis of the surgical orientation device 12 to account for a predetermined range of motion of the surgical orientation device 12 about the flexion/extension axis during the procedures. It should be appreciated by one of ordinary skill in the art that the accelerometer can be mounted at acute angles other than approximately 22 degrees. In other arrangements, the sensor(s) 1104 can be mounted to be offset to account for a predetermined range of motion about other axes of rotation as well. In yet other arrangements, for example, when a three-axis accelerometer is used, the accelerometer sensor(s) can be mounted in parallel with the anterior-posterior axis of the surgical orientation device 12. In one three-axis accelerometer arrangement, a handoff system can be incorporated to ensure that the accelerometer sensors with the most accurate reading (e.g., <45 degrees) are being used at each orientation position. The handoff system can employ hysteresis to avoid "bouncing" phenomena during the handoffs between the accelerometer sensors.

Figure 12D:
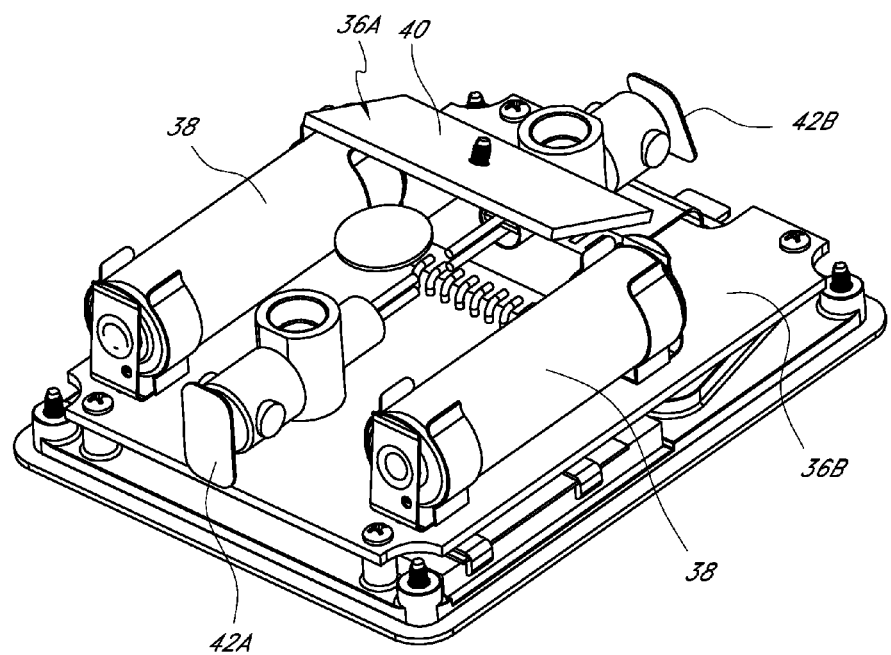
FIG. 12D is a perspective view of interior components of the surgical orientation device of FIG. 7.

FIG. 12D illustrates the inside of the surgical orientation device 12, according to an embodiment of the invention. The surgical orientation device 12 can comprise one or more circuit boards and/or other circuitry capable of installation within the surgical orientation device 12. As illustrated, the surgical orientation device 12 can comprise a sensor board 36A and a main board 36B. The components of the sensor module (including the sensor(s) 1104) can be mounted on the sensor board 36A and the other components of the electrical system 1100 are mounted on the main board 36B. The sensor board 36A can comprise one or more sensors 40 (e.g., sensor(s) 1104 as described above). In alternative embodiments, the sensor board 36A and the main board 36B can be combined into a single circuit board. The sensor board 36A and the main board 36B can comprise rigid or flexible circuit boards. The sensor board 36A and the main board 36B can be fixedly or removably attached to the outer housing 20.

As illustrated, the sensor board 36A is mounted at an approximately 22-degree angle relative to a plane extending longitudinally through the housing 20, which can be parallel to or correspond to an anterior-posterior axis of the main board 36B. As described above, mounting the sensor board 36A at an offset angle can enable the one or more sensors to operate in the regions of maximum or optimum sensitivity, accuracy and/or resolution. The particular mounting offset angle can be selected based on a range of motion of the surgical orientation device 12 during a particular orthopedic procedure. For example, during the tibial preparation procedures described herein, the surgical orientation device 12 can be aligned with the coronal plane of the tibia with the leg in flexion and during the femoral preparation procedures described herein, the surgical orientation device 12 can be aligned to the leg in extension. Accordingly, the mounting offset angle is set at approximately 22 degrees to keep the orientation of the sensors from getting too close to the less accurate, low resolution range when the surgical orientation device 12 is positioned in the two flexion/extension orientations. As shown in FIG. 12D, the surgical orientation device 12 can include two AA batteries 38 as the power supply 1110 for providing power to the surgical orientation device 12. The surgical orientation device 12 also can include lasers 42 as the visible alignment indicators 1106 described above.

Figure 12E:
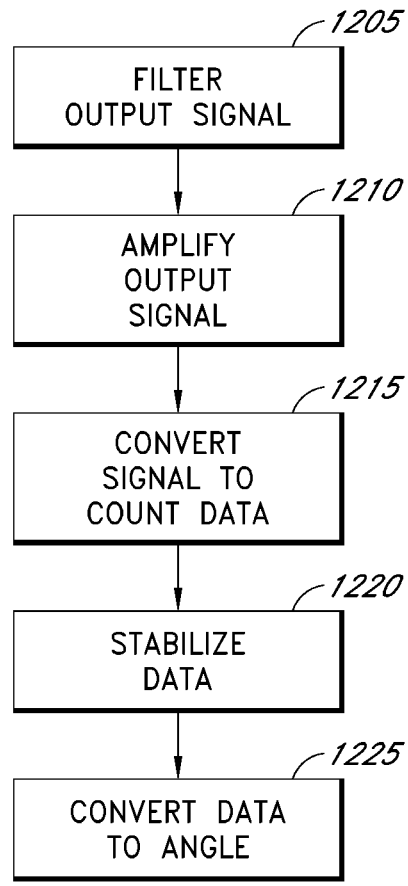
FIG. 12E is a flow chart of an embodiment of an orientation measurement process performed by the surgical orientation device of FIG. 7.

FIG. 12E is a high-level flowchart of an exemplary conversion process for converting an analog voltage output signal of a multi-axis accelerometer into an angle degree measurement for presentation on the display 24. Although the steps are described as being implemented with hardware and/or software, each of the steps illustrated in FIG. 12E can be implemented using hardware and/or software. It should be appreciated that a similar conversion process can be performed for any other type of sensor or for multiple separate sensors without departing from the spirit and/or scope of the disclosure.

For each axis of rotation measured (e.g., pitch and roll), the multi-axis accelerometer can continuously output an analog voltage signal. At Block 1205, the signal conditioning circuitry of the sensor module can filter the analog output voltage signal (e.g., with a low pass filter) to remove noise from the signal that may be present due to the high sensitivity of the multi-axis accelerometer. At Block 1210, the signal conditioning circuitry amplifies, or boosts, the output voltage signal, for example, via the gain circuitry described above.

At Block 1215, the ADC can convert the continuous analog voltage signal into a discrete digital sequence of data samples, or voltage counts. In certain embodiments, the ADC can sample the analog voltage signal once every two milliseconds; however, other sampling rates are possible. In certain embodiments, the analog voltage signal is oversampled. At Block 1220, the electronic control unit 1102 can generate a stable data point to be converted to an angle measurement. The electronic control unit 1102 can apply a median filter to the sampled data to eliminate outliers (e.g., spikes) in the data. For example, the electronic unit 1102 can use an 11-sample median filter to generate the middle value from the last 11 samples taken. The output of the median filter can then be fed into a rolling average filter (for example, a 128 sample rolling average filter). The rolling average filter can be used to smoothe or stabilize the data that is actually converted to an angle measurement. The electronic control unit 1102 can implement Blocks 1215 and 1220 using a finite impulse response ("FIR") or an infinite impulse response ("IIR") filter implemented in a software module.

At Block 1225, the electronic control unit 1102 can convert the voltage count data to an angle measurement in degrees. In performing the conversion, the electronic control unit 1102 can be configured to apply a calibration conversion algorithm based on a calibration routine performed during a testing phase prior to sale of the surgical orientation device 12. The calibration conversion can be configured to account for unit-to-unit variations in components and sensor placement. The calibration routine can be performed for each axis being monitored by the multi-axis accelerometer. The calibration conversion can comprise removing any mechanical or electrical offsets and applying an appropriate gain calibration for a positive or negative tilt.

As described above, the ADC can comprise an ADC with 12-bit resolution, which provides 4096 distinct voltage counts, wherein a −90 degree tilt corresponds to 0 counts (−2048 signed counts), a zero degree tilt corresponds to 2048 counts (0 signed counts), and a +90 degree tilt corresponds to 4096 counts (+2048 signed counts). The tilt angle for each axis (e.g., pitch and roll) of the multi-axis accelerometer can be calculated from the voltage count data based on standard trigonometric relationships as the arcsin of the acceleration component in each particular axis. In arrangements in which the electronic control unit 1102 applies the calibration conversion, the tilt angle for each axis can be calculated as follows:

$$\text{ANGLE} = a\sin\left[\frac{\left(\frac{\text{SignedADC Counts} + }{\text{OFFSET}}\right) \times \text{GAIN}}{2048}\right], \quad (12.1)$$

where OFFSET corresponds with a zero offset of the surgical orientation device 12 determined during the calibration routine and GAIN corresponds with a ratiometric value determined during the calibration routine, with one GAIN value being used for negative tilt angles and a different GAIN value being used for positive tilt angles.

Also at Block 1225, in arrangements where a dual-axis accelerometer is used, the electronic control unit 1102 can be configured to adjust the pitch angle (x axis) calculation to account for the mounting offset angle (described above) of the dual-axis accelerometer relative to the outer housing 20 of the surgical orientation device 20. The result of Block 1225 is an absolute angle for each axis of rotation (e.g., pitch, roll) being monitored by the dual-axis accelerometer. The absolute pitch and roll angles can be used to calculate orientation measurements of the surgical orientation device 12, such as a flexion-extension angle and a varus/valgus angle (as described in more detail below).

Orientation measurements for the surgical orientation device 12 can be determined based on a wide variety of reference frames in conjunction with any of a variety of surgical procedures. For example, when used in conjunction with a total knee replacement arthroscopic procedure, a reference frame can be established as shown in FIG. 12F.

Figure 12F:
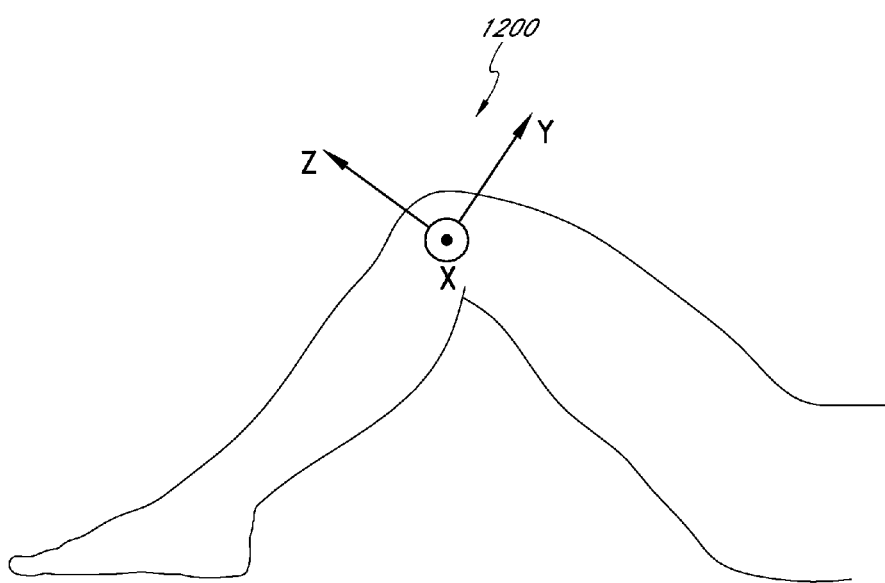
FIG. 12F is a side view of a left leg of a patient illustrating an orientation reference frame.

As illustrated in FIG. 12F, the reference frame 1200 comprises three orthogonal axes (labeled x, y and z) having a point of origin at the center of a patient's knee joint when the patient's left leg is in flexion. The x-axis is illustrated as extending out of the page (in a lateral direction from the knee parallel to the horizon). The y-axis is illustrated as extending along a coronal plane of the tibia. The z-axis is illustrated as extending straight out from the knee at an offset of 90 degrees from the coronal plane of the tibia. As described herein, a flexion/extension rotation, or posterior-anterior pitch rotation, corresponds to rotation about the x-axis of the reference frame 1200 and a varus/valgus rotation, or a medial-lateral rotation, corresponds to rotation about the z-axis of the reference frame 1200. A roll rotation, as described herein, corresponds to rotation about the y-axis of the reference frame 1200. During the performance of alignment procedures in which the leg is fully extended, the x-axis maintains the same orientation and the y and z axes rotate toward the mechanical axis of the leg about the x axis.

As described above, a sensor 40 (e.g., a multi-axis accelerometer) can be configured to measure changes in angular position from a horizontal axis (e.g., pitch) and a vertical axis (e.g., roll). In performing the methods described herein, the surgical orientation device 12 can be mounted such that the pitch measurement of the sensor 40 corresponds to rotation about the x axis (e.g., flexion/extension rotation) of the reference frame 1200 and such that the roll measurement of the sensor 40 corresponds with rotation about the y axis of the reference frame 1200.

In arrangements employing the use of the tibial preparation system 310, the flexion/extension angle is calculated according to formula 12.1 above. In arrangements where a dual-axis accelerometer is used, the calculated flexion/extension angle can be adjusted to account for a mounting offset angle or can be compared to a reference flexion/extension orientation plane to generate a relative angle measurement. A relative flexion/extension angle can be generated by subtracting a reference flexion/extension angle stored in memory from the absolute measured flexion/extension angle. In certain embodiments, the reference flexion/extension angle corresponds with the orientation of the coronal plane of the tibia.

In arrangements employing the use of the tibial preparation system 310, the varus/valgus angle can be derived based on the assumption that the pitch angle of the accelerometer, which corresponds with the flexion/extension angle of the surgical orientation device 12, is fixed and known (e.g., the surgical orientation device 12 is mounted to an extramedullary alignment guide 314 that can only be rotated laterally or medially on a plane of fixed pitch) and on the assumption that the rotation angle of the roll sensor of the accelerometer was substantially zero degrees when the fixed pitch angle measurement (e.g., the reference flexion/extension angle) was registered, or recorded. Based on these two assumptions, the varus/valgus angle can be calculated as follows:

$$\text{Varus/Valgus Angle} = \arcsin\left[\frac{\sin(rollangle)}{\sin(fixedpitchangle)}\right] \quad (12.2)$$

where the roll angle is the current absolute roll angle being measured by the roll sensor of the accelerometer. A relative varus/valgus angle can be generated by subtracting a reference varus/valgus angle stored in memory from the absolute measured varus/valgus angle. In certain embodiments, the reference varus/valgus angle corresponds with the orientation of the sagittal plane of the tibia.

In arrangements where the tibial preparation systems 410 and 610 are used, the flexion/extension angle and the varus/valgus angle can be calculated as follows:

$$\text{Varus/Valgus Angle} = \arctan\left[\frac{\sin(rollangle)}{\sin(pitchangle)}\right] \quad (12.3)$$

$$\text{Flexion/Extension Angle} = \arcsin\left[\frac{\sin(rollangle)}{\sin(Varus/ValgusAngle)}\right], \quad (12.4)$$

where the roll angle is the current absolute roll angle being measured by the accelerometer and the pitch angle is the current absolute pitch angle being measured by the accelerometer. As discussed above, these calculations can also be adjusted based on a calibration conversion or a mounting offset angle.

In certain embodiments, the above calculations can be performed by software modules executed by the electronic control unit 1102. In other embodiments, the electronic control unit 1102 can generate the angle measurements using data stored in one or more look-up tables ("LUT"s). In other embodiments, other calculations can be derived based on the type of sensor or sensors used, the procedure being performed, and/or the reference frame being employed.

In certain embodiments, the electronic control unit 1102 can perform a stabilization routine, process, or algorithm to assess or determine the stability, or reliability, of the calculated angle measurements. For example, the electronic control unit 1102 can keep a history of the last 100 ms of calibrated sample data for each axis being monitored by the sensor(s) 40. Each time a new sample is added to the 100-sample history, a maximum and minimum value is determined for the 100-sample data set. The electronic control unit 1102 can then determine a delta difference between the maximum and minimum values. The electronic control unit 1102 can then compare the delta difference between the maximum and minimum values to a threshold. If the delta difference is lower than the threshold, then the data is considered to be stable and it is stored in memory (e.g., external memory 1112) and time-stamped. If the delta difference is greater than the threshold, then the data is considered to be unstable. When retrieving an angle reading to display to the user, the electronic control unit 1102 can be configured to transmit the last stable data reading (assuming it is not too old) to the display 1110 instead of the current unstable reading. If the last stable angle exceeds a time threshold, the unstable angle reading can be displayed along with a visual indication notifying the user that the angle reading is unstable. For example, a red "shaky hand" icon or graphical user interface image can be displayed on the display screen.

Figure 13:
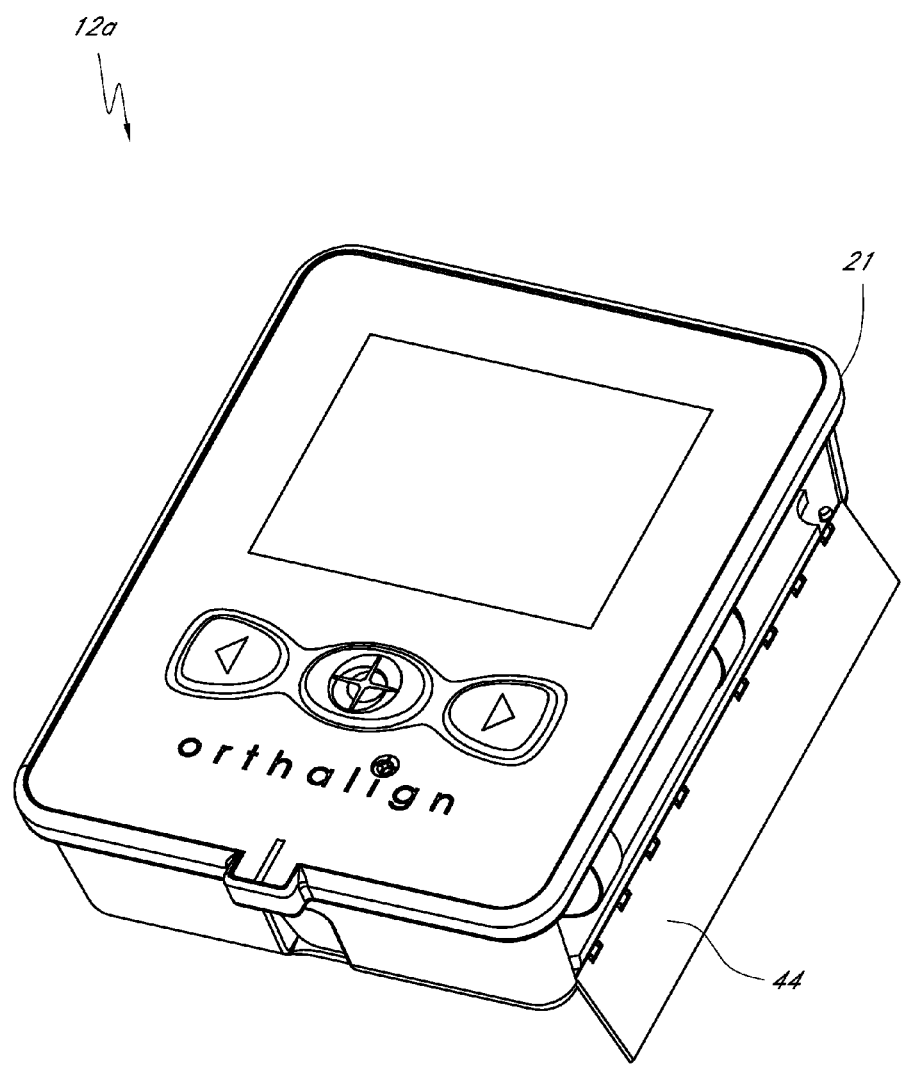
FIG. 13 is a perspective view of a surgical orientation device according to another embodiment.

2. Surgical Orientation Device with a Disposable Portion which Allows Inner Components to be Reused in a Sanitary Manner In one embodiment, a surgical orientation device can be provided with a disposable housing. This arrangement can maximize reuse of internal components while maintaining the cleanliness of the device. FIG. 13 shows an embodiment of a surgical orientation device 12a which comprises a disposable outer housing 21. The disposable outer housing 21 can include, or be releasably attached to, a cover 44. The cover 44 can be in the form of a latch, flap, zipper, plastic-zip fastener, or other similar structure which covers and/or seals an opening in the disposable outer housing 21. The cover 44 can be pivotally connected to a portion of the disposable outer housing 21, such that when the cover 44 is swung open or removed, visual inspection and removal/insertion of interior, reusable components (e.g. the electronic control unit 1102, display 24, optical components 32) of the surgical orientation device 12a is provided.

The disposable outer housing 21 can be manufactured and packaged in a sterile state and can provide a sterile barrier between the reusable components inside the surgical orientation device 12 and their outside environment. Thus, once the surgical orientation device 12 has been used, the disposable outer housing 21 can be discarded or destroyed, and the interior, reusable components can be used again.

The disposable outer housing 21 can also be manufactured such that it engages and/or receives one or more interior reusable components of the surgical orientation device 12. Preferably these components are received within the housing 21 without the interior reusable components contacting any outside surface of the disposable outer housing 21, thereby protecting the outside surfaces of the disposable outer housing 21 from contact with the interior reusable components. A separate, sterile shield can provide a temporary barrier between the sterile housing and non-sterile surgical orientation device 12 during insertion to prevent accidental contact between the surgical orientation device 12 and outside surfaces of the housing. Once the surgical orientation device 12 is inserted the shield can be removed and discarded allowing the door to be closed.

The disposable outer housing 21 can contain slots or grooves on one or more interior walls of the disposable outer housing 21 to enable the interior reusable components, or a combined set of interior reusable components in the form of a reusable assembly, to be positioned or set within the disposable outer housing 21. For example, the reusable components or assembly can contain slots or grooves which mate with the slots or grooves of the disposable outer housing 21. This mating arrangement can minimize contact between more delicate features of the reusable components (e.g. a circuit board) and the inside surfaces of the disposable outer housing 21. In some embodiments the inside of the disposable outer housing 21 and the outside of the interior reusable components or assembly can be tapered to allow easy, low precision insertion of the interior reusable components or assembly but provide secure mating once the disposable outer housing 21 and the reusable interior components or assembly are fully engaged. Electrical contact between the surgical orientation device 12 and housing can be provided by spring loaded probes and conductive contacts. The disposable housing 21 can include touch screen for user interface. (e.g. an LCD display can still be part of the SOD). The disposable housing 21 can be packaged with disposable batteries so users don't have to deal with recharging of batteries.

In yet other configurations, the interior reusable components, assembly, and/or disposable outer housing 21 of the device can contain other mating features, including but not limited to clamps or adaptors, which facilitate sanitary handling of the surgical orientation device 12.

The disposable outer housing 21 can also contain one or more sheets of material, such as a thin plastic layer, temporarily affixed to one or more of its outside surfaces (for example by a weak adhesive), sufficient to protect the disposable outer housing 21 from contamination by the reusable interior components or assembly during the process of engaging the disposable outer housing 21 to the reusable interior components or assembly. The sheets of material temporarily affixed to the disposable outer housing 21 can be removed following the engagement of the disposable outer housing 21 to the reusable interior components or assembly.

In a preferred arrangement, the disposable outer housing 21 can include a transparent section or sections (e.g. a thin plastic membrane) which covers both the display 24 and user inputs 26. This section or sections of the disposable housing 21 can be manufactured to allow the user to manipulate the user interface elements by pressing against this section or sections of the disposable housing 21. For example, the disposable outer housing 21 can include a touch-sensitive overlay which covers the display 24 to enable the display 24 of the surgical orientation device 12 to be operated as a touch screen. The surgical orientation device 12 can include an electrical interface, for example probes or sliding contacts, between the disposable and re-usable elements of the touch screen (i.e. the transparent sections of the disposable outer housing 21 and the display 24) to enable the transfer of information, electricity and/or other energy between the disposable outer housing 21 and the display 24.

With continued reference to FIGS. 12 and 13, the batteries 38 can be in either or both of the reusable and disposable portion or portions of the surgical orientation device 12. If the batteries 38 are contained in the disposable outer housing 21, the surgical orientation device 12 can contain one or more transmission media, connectable between the reusable interior elements or assembly and the disposable outer housing 21, capable of conducting power from the batteries in the disposable outer housing 21 to the reusable interior components or assembly that requires power for the surgical orientation device's operation.

3. Device for Coupling a Surgical Orientation Device to Orthopedic Fixtures

Figure 14:
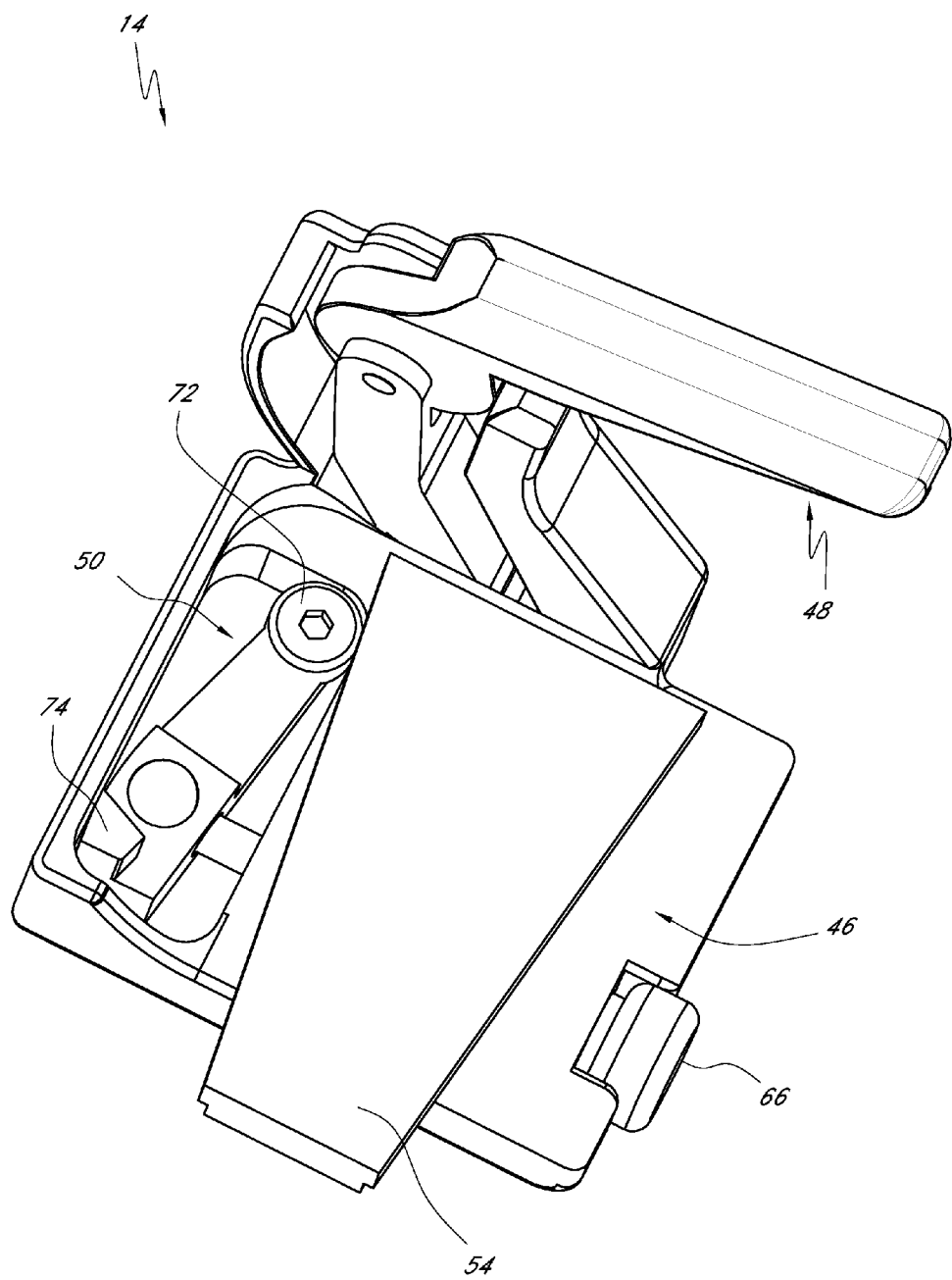
FIG. 14 is a perspective view of a coupling device according to one embodiment that can be used to connect the surgical orientation device of FIG. 7 to other components.

A device can be provided which can be used to couple a surgical orientation device to one or more orthopedic fixtures. For example, FIGS. 2 and 14 show a coupling device 14. The coupling device 14 can comprise a housing 46, cam mechanism 48, and a surgical orientation device attachment mechanism 50. The coupling device 14 can be used generally to attach two surgical instruments and/or components together. For example, in the tibial preparation system 10, the coupling device 14 can be used to couple the surgical orientation device 12 to the universal jig 16.

Figure 15:
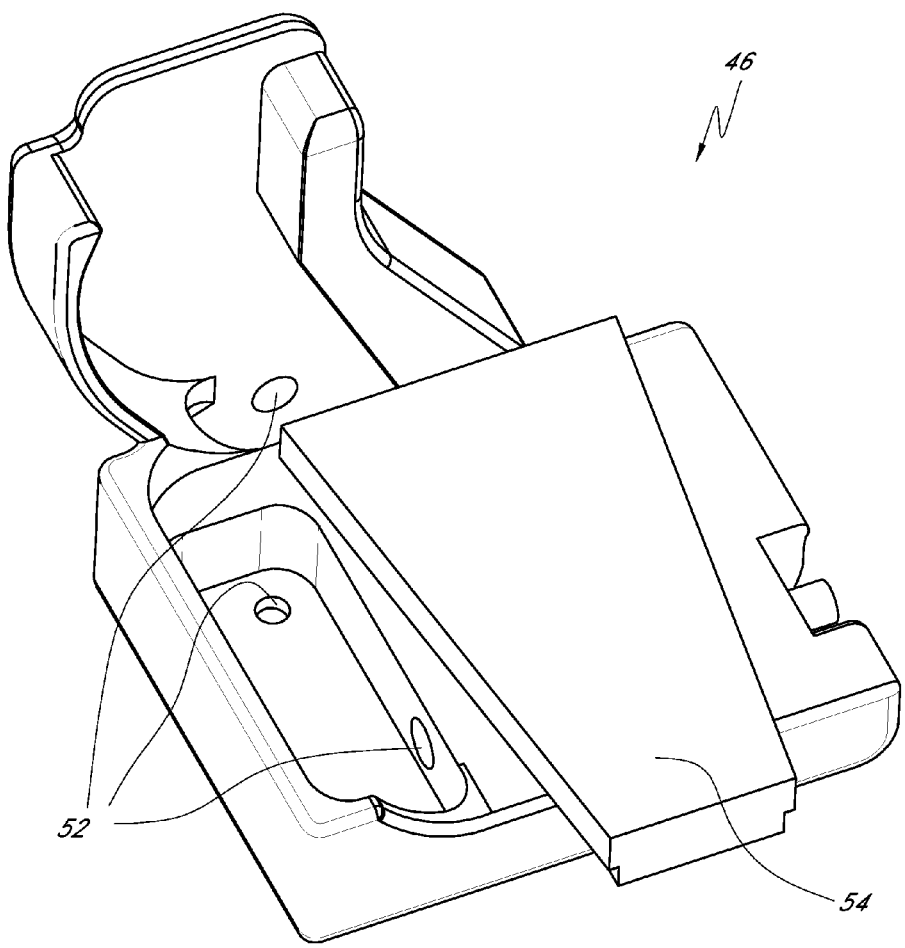
FIG. 15 is a perspective view an outer housing of the coupling device of FIG. 14.

FIG. 15 shows the housing 46, which can be made out of plastic or other suitable material including but not limited to polypropylene or PET. The housing 46 can include openings and/or slots 52 for insertion of the cam mechanism 48 and surgical orientation device attachment mechanism 50. The housing 46 can further include an elongate portion 54, which can be inserted into the grooves or channels 30 along the back portion of the surgical orientation device 12 described above.

Figure 16:
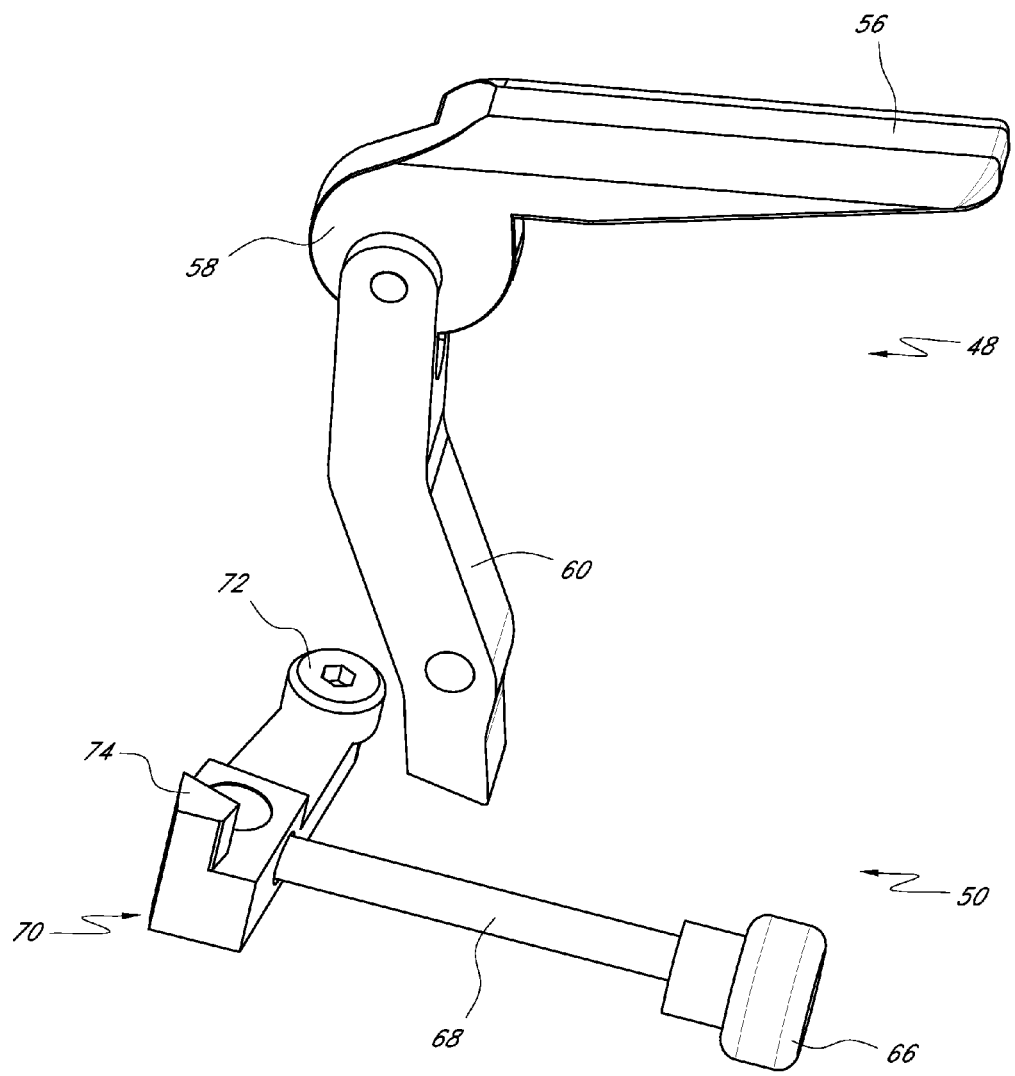
FIG. 16 is a perspective view of interior components of the coupling device of FIG. 14.

FIG. 16 shows the cam mechanism 48, which can comprise a handle 56 with an off-center cam 58 at one end. The off-center cam 58 can be pivotally attached to an arm 60. The arm 60 can include a pin or pivot mechanism which is insertable into an opening 52 of the housing 46.

Figure 17:
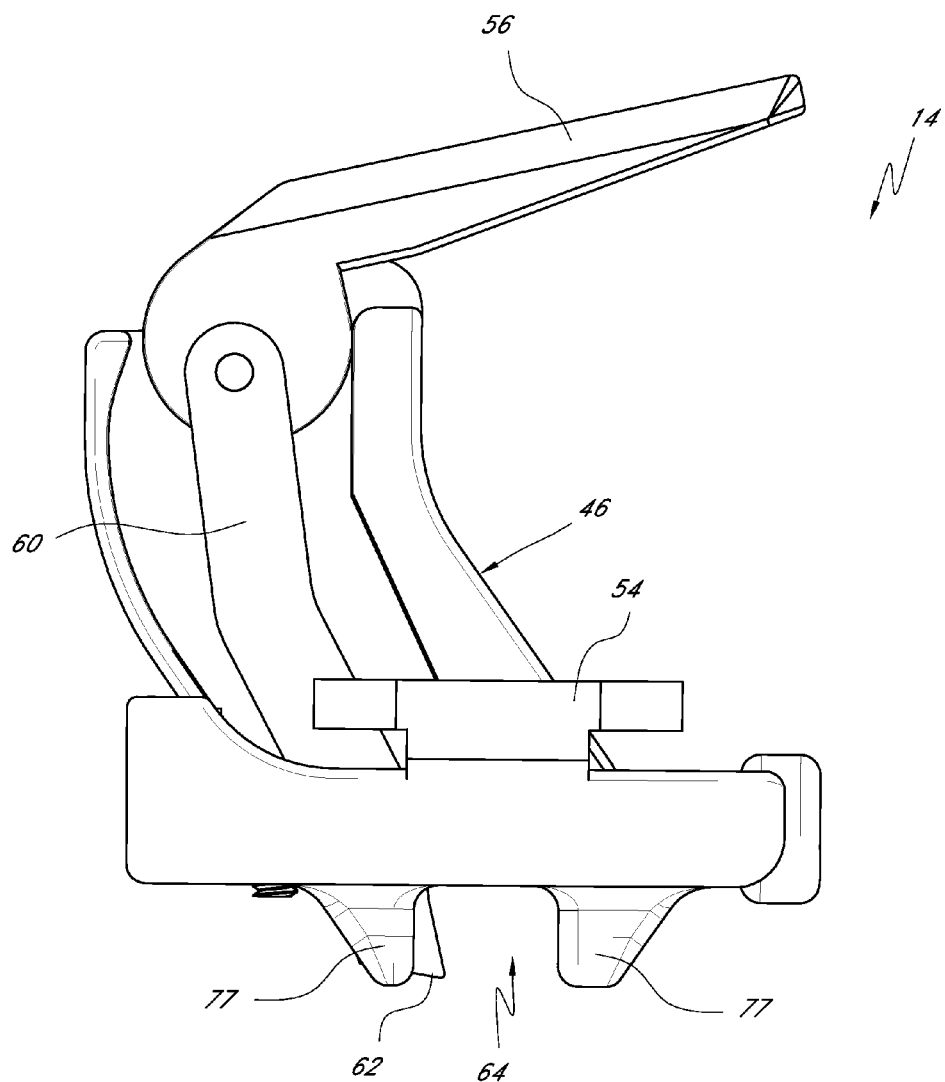
FIG. 17 is a plan view of the coupling device of FIG. 14.

FIG. 17 shows the coupling device 14 fully assembled. The coupling device 14 can be used to frictionally engage and hold onto a surgical instrument or component. For example, as the handle 56 is rotated, the arm 60 can swing into a position such that an end 62 of the arm 60 is frictionally engaged with or clamps onto a portion of a surgical instrument or component extending through the opening 64. The surgical instrument or component can extend between structures 77 of the housing 46 such that as the arm 60 swings, the end 62 can contact the surgical instrument or component and press it firmly against the structure 77, thereby at least partially locking the surgical instrument or component to the coupling device 14.

With reference again to FIG. 16, the surgical orientation device attachment mechanism 50 can comprise a knob 66. The knob 66 can be attached to an arm 68. The arm 68 can be attached to a rotatable structure 70. The rotatable structure 70 can comprise a pin 72 which can be inserted into an opening 62 of housing 46. The rotatable structure 70 can also comprise a protrusion 74. As the knob 66 is pushed, and/or turned, the protrusion 74 can pivot about the pin 72.

With reference to FIGS. 8, 9, 14, and 16, the surgical orientation device 12 can be securely attached to the coupling device 14. To attach the surgical orientation device 12 to the coupling device 14, the elongate portion 54 of the coupling device 14 can be inserted into the grooves or channels 30 along the back of the surgical orientation device 12. Once a portion of the elongate portion 54 is inside the grooves or channels 30, the surgical orientation device attachment mechanism 50 can be used to secure the surgical orientation device 12 to the coupling device 14. For example, the knob 66 can be pulled, and/or turned, such that the protrusion 74 pivots about the pin 72, and moves into a groove 76 shown in FIGS. 8 and 9. Once inside the groove 76, the protrusion 74 can inhibit the surgical orientation device 12 from slipping off of and/or becoming removed from, the coupling device 14. In some embodiments, the knob 66 and/or protrusion 74 can be biased by a compressive member (e.g. spring) housed in the housing 46 to facilitate attachment of the coupling device 14 to the surgical orientation device 12. For example, the protrusion 74 can be biased towards a locking position in which the protrusion is moved towards the groove 76 shown in FIGS. 8 and 9. In some embodiments, the knob 66 can be pushed and/or turned to release the surgical orientation device 12 from the coupling device 14.

While the coupling device 14 described above can be used to attach and/or couple the surgical orientation device 12 with the universal jig 16, other methods and devices for attaching and/or coupling the components of the tibial preparation system 10 are also possible.

Figure 17A:
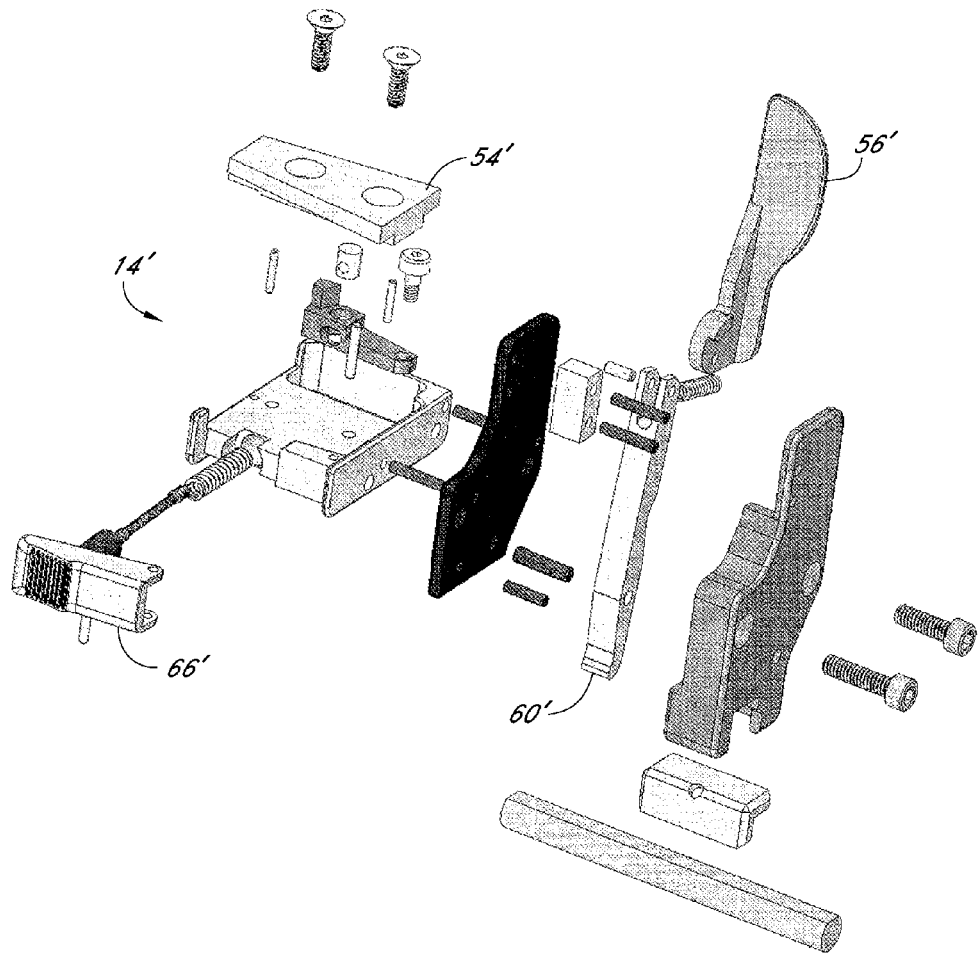
FIG. 17A is an exploded view a coupling device according to another embodiment.

FIG. 17a shows another embodiment of a coupling device 14'. The coupling device 14' can be similar to the coupling device 14 described above, and can include an elongate protrusion 54', a handle 56', an arm 60', and a knob 66'. The knob 66' can comprise a lever-like structure which can pivot in order to lock and unlock a portion of the coupling device.

Figure 18:
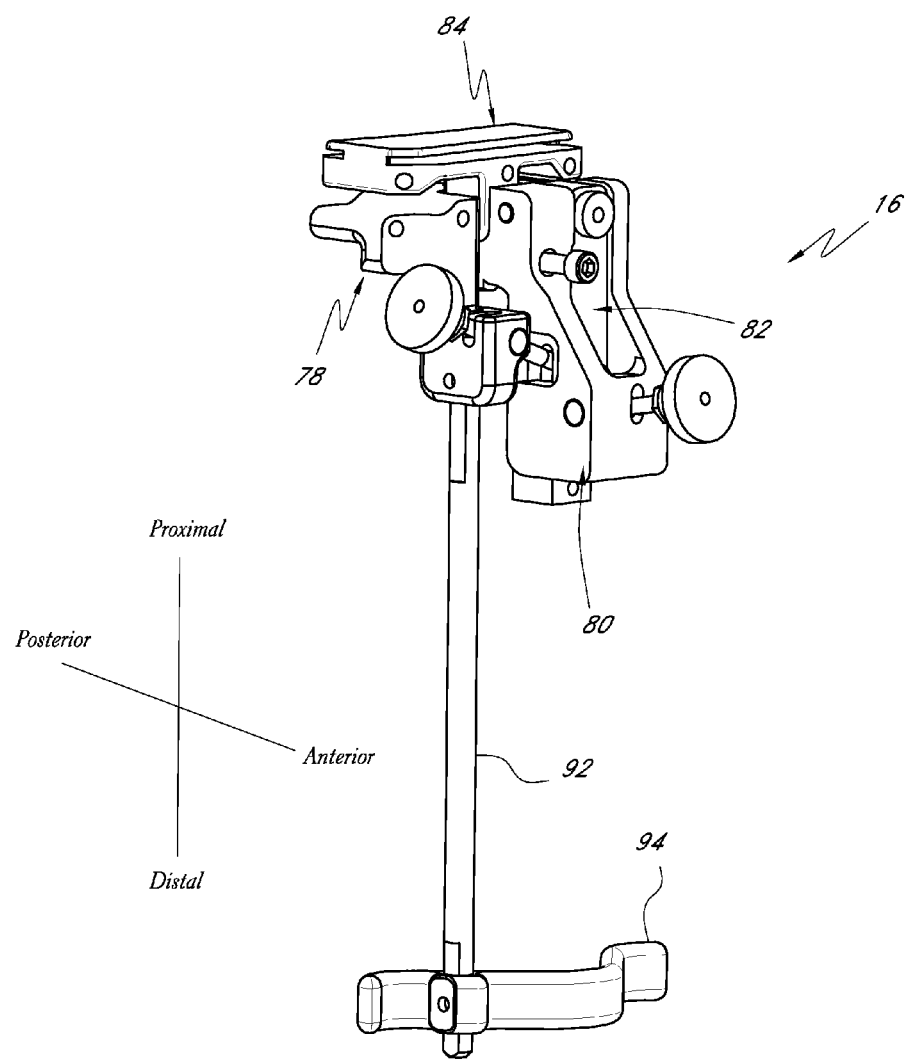
FIG. 18 is a perspective view of an orthopedic fixture according to one embodiment which can be used as a universal jig.
Figure 19:
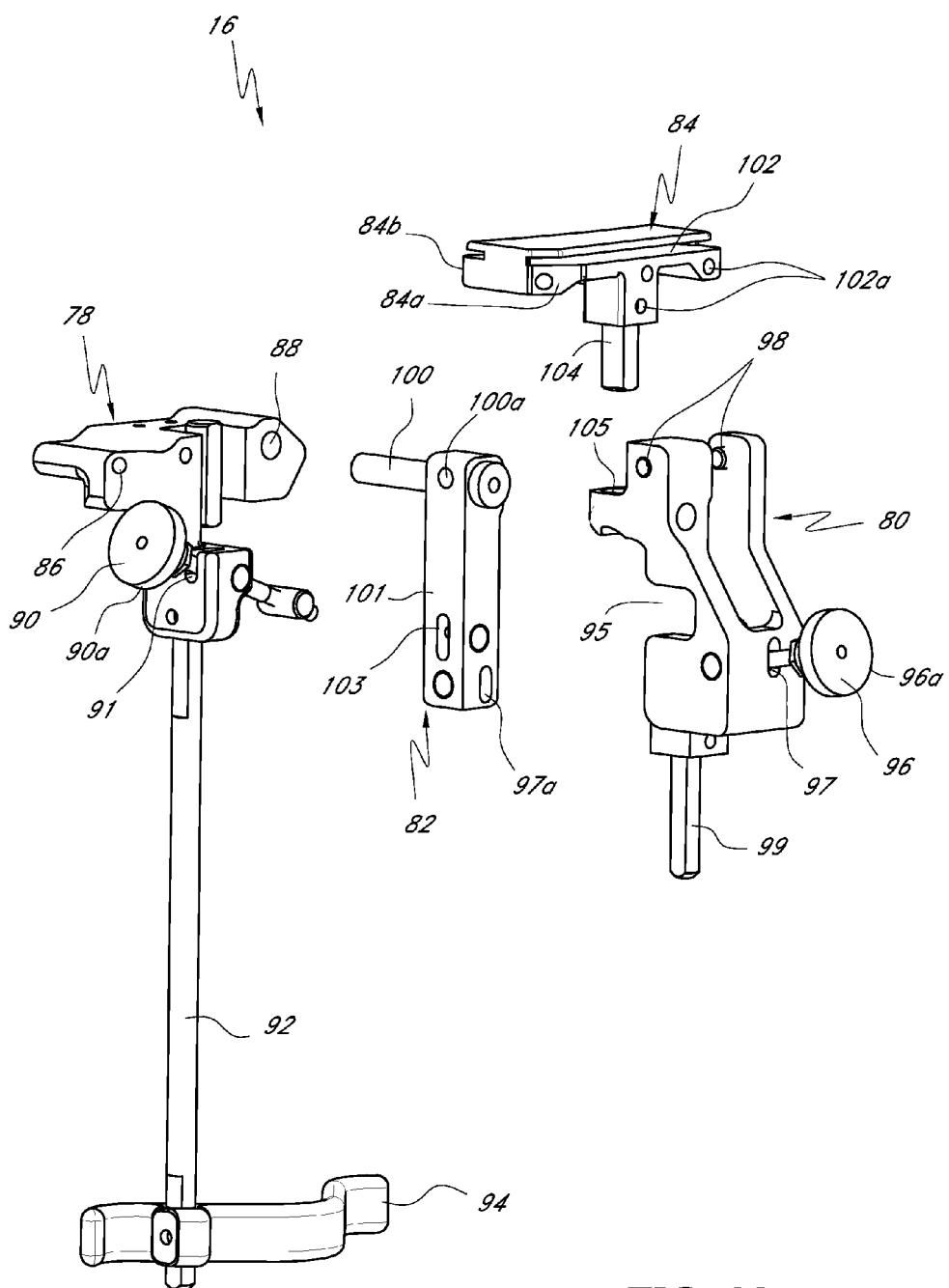
FIG. 19 is an exploded view of the orthopedic fixture of FIG. 18.

4. Orthopedic Fixture for Orienting a Surgical Orientation Device in Multiple Degrees of Freedom An orthopedic fixture can be provided which can have a moveable portion or portions which are used to orient a surgical orientation device. The surgical orientation device can be oriented in multiple degrees of freedom. For example, FIGS. 2, 18, and 19 show an orthopedic fixture in the form of a universal jig 16. The universal jig 16 can comprise a base member 78, a posterior/anterior adjustment block 80, a varus/valgus adjustment block 82, and a cutting block 84 (e.g. an anterior block for placement or attachment along an anterior surface of the tibia). These components provide for multiple degrees of freedom of operation of a moveable portion of the jig 16 such that devices coupled therewith (e.g., the surgical orientation device 12) can be moved to a variety of orientations during the procedure.

a. Base Member for Providing an Anchored or Fixed Initial Position of an Orthopedic Fixture A base member can be provided that anchors an orthopedic fixture and/or provides a fixed initial position of a moveable orthopedic fixture. For example, a base member 78 can comprise a structure that is rigidly and/or fixedly attached to an anatomical structure. The base member 78 can be attached to an anterior surface of a patient's tibia. In a preferred arrangement, the base member 78 can comprise at least one base member attachment opening 86. For example, the base member 84 can comprise two base member attachment openings 86. Attachment openings, apertures, and/or holes as described herein with respect to tibial preparation system 10 and other systems described herein, can comprise bores, non-threaded holes, threaded holes, and/or other types of holes or openings which extend partially or entirely through a structure.

For example, the base member attachment openings 86 can extend entirely through the base member 78. Each of the base member attachment openings 86 can be configured to receive a fastening device, such as for example a screw, to anchor the base member 78 into a bone or other anatomical structure and fix the base member 78 relative to the bone or anatomical structure.

The base member 78 can further comprise a base member receiving opening 88. The receiving opening 88 can be located along an anterior side of the base member 78, and can be sized and shaped so as to receive a pin of the varus/valgus adjustment block 82. The receiving opening 88 can extend entirely or partially through the base member 78, and in some embodiments can be partially or entirely threaded.

The base member 78 can further comprise a base member pin 90. Pins, as described herein with respect to tibial preparation system 10 and other systems described herein, can be solid, threaded, formed of plastic, metal, or other material, comprise linear bearings, and/or have shapes sizes, and configurations other than those shown and/or described.

The pin 90 can extend through an opening or openings 91 of the base member 78, and can be sized and shaped so as to be inserted through a cut-out 95 of the posterior/anterior adjustment block 80. The pin 90 can be partially or entirely threaded, and can include a knobbed portion 90a on one end which can be gripped and turned by a user.

The base member 78 can further comprise an elongate base member rod 92. The elongate base member rod 92 can extend distally beneath the pins 90, 96, and can include a brace-like structure 94 on a distal end thereof. The brace-like structure 94 can be curved, and used to brace and/or hold the universal jig 16 against the patient's skin overlying the tibia during the knee replacement procedure. The base member rod 92 and structure 94 can provide a stabilizing force against a portion of the tibia. For example, the structure 94 can be placed around, or wrapped, against the skin near a proximal portion of the tibia. The universal jig 16 can, while being anchored or moved as described herein, experience a force or forces which can tend to cause the universal jig 16 as a whole to twist or rotate. The structure 94 can at least partially absorb these forces by bracing itself against the tibia. For example, the structure 94 can minimize a torquing motion of the universal jig 16 while an anchoring pin or pins are being inserted through the base member and into the tibia. Also, once the universal jig 16 is locked in position for resection it can resist torquing during resection caused by pressure of a cutting tool in a slot of the cutting block 84. This can improve accuracy of resection. The base member rod 92 and structure 94 can be adjusted accordingly to account for these forces. For example, the structure 94 can be rotated about the end of the base member rod 92, and/or be made of material capable of withstanding anticipated forces. Additionally or alternatively, the base member rod 92 can be configured to adjust distally so as to extend or shorten, depending on a desired location for the structure 94.

b. Device for Adjusting a Posterior/Anterior Slope of a Cutting Block

A device can be provided which can be used to adjust the orientation in a sagittal plane of a surgical orientation device and/or cutting block. For example, and with continued reference to FIGS. 2, 18, and 19, the posterior/anterior adjustment block 80 of universal jig 16 can comprise a structure which is moveable (e.g. rotatable) in at least one of a posterior and anterior direction.

The posterior/anterior adjustment block 80 can comprise a cutout 95. The cutout 95 can be sized and shaped so as to generally receive and/or surround the base member pin 90. The cutout 95 can extend entirely through the posterior/anterior adjustment block 80, and can generally form a cut-out portion of the block 80.

The posterior/anterior adjustment block 80 can further comprise a posterior/anterior adjustment pin 96. The pin 96 can extend through an opening 97 of the posterior/anterior adjustment block 80. One end of the pin 96 can be sized and shaped so as to contact and/or be inserted within an opening 97a of the varus/valgus adjustment block 82. The pin 96 can be partially or entirely threaded, and can include a knobbed portion 96a on one end which can be gripped and turned by a user.

The posterior/anterior adjustment block 80 can further comprise posterior/anterior adjustment block hinge openings 98. The hinge openings 98 can be sized and shaped to receive a pin-like structure. The posterior/anterior adjustment block 80 can pivot about the pin-like structure and/or about an axis extending through the hinge openings 98 when the knob 96a on the end of the posterior/anterior adjustment block pin 96 is turned.

The posterior/anterior adjustment block 80 can further comprise an opening 105 and/or structure which can receive and/or affix a portion of the cutting block 84 (e.g. rod 104) to the posterior/anterior adjustment block 80. By affixing the posterior/anterior adjustment block 80 to the cutting block 84, movement of the posterior/anterior adjustment block 80 and cutting block 84 can be linked such that movement of the posterior/anterior adjustment block 80 can cause similar or identical movement of the cutting block 80.

The posterior/anterior adjustment block 80 can further comprise a posterior/anterior adjustment block guide rod 99. The guide rod 99 can extend from the posterior/anterior adjustment block 80, and can be sized and shaped to receive and/or couple with the surgical orientation device 12, or coupling device 14.

c. Device for Adjusting a Varus/Valgus Slope of a Cutting Block

A device can be provided which can be used to adjust the orientation in a coronal plane of a surgical orientation device and/or cutting block. For example, and with continued reference to FIGS. 2, 18, and 19, the varus/valgus adjustment block 82 of universal jig 16 can comprise a structure which is moveable (e.g. rotatable) in at least one of a varus/valgus direction.

The varus/valgus adjustment block 82 can comprise a varus/valgus adjustment block pin 100. The pin 100 can extend through a portion or portions of the varus/valgus adjustment block 82. The pin 100 can be received within the base member receiving hole 88, and in some embodiments can be partially or entirely threaded. In some embodiments the pin 100 can be unthreaded. The pin 100 can include a pin opening 100a. The pin opening 100a can receive the same pin-like structure received by the hinge openings 98 described above.

When the base member pin 90 is turned, the varus/valgus adjustment block 82 can pivot about the pin 100, such that the varus/valgus adjustment block 82 pivots in at least one of a varus and valgus direction.

The varus/valgus adjustment block 82 can further include an opening 103 along a side surface 101 of the varus/valgus adjustment block 82, which can receive the base member pin 90. In some embodiments the opening 103 can be threaded or structured in a manner such that turning the knob 90a on the end of the pin 90 in either a clockwise or counterclockwise direction can cause movement of the varus/valgus adjustment block 82.

With continued reference to FIGS. 2 and 18, movement of the varus/valgus adjustment block 82 can cause movement of the posterior/anterior adjustment block 80. For example, a portion or portions of the varus/valgus adjustment block 82 can rest within and/or be contacted on either side by portions of the posterior/anterior adjustment block 80, such that any movement of the varus/valgus adjustment block 82 in a varus or valgus direction likewise causes similar or identical movement of the posterior/anterior adjustment block 80.

d. Cutting Block Which can be Oriented in a Posterior/Anterior, and/or a Varus/Valgus, Direction for Bone Resection A cutting block, or other orthopedic fixture, can be provided for bone resection. The cutting block can be oriented with the aid of a surgical orientation device, an orthopedic fixture, or a surgical orientation device and an orthopedic fixture. For example, and with continued reference to FIGS. 2, 18, and 19, the cutting block 84 can comprise at least one opening 102. One opening 102 can comprise, for example, an elongate slit along a width of an upper, or proximal, portion of the cutting block 84 for receiving and guiding a saw, blade, or other cutting tool. Other openings 102a can extend from an anterior face 84a of the cutting block 84 towards a posterior face 84b thereof, and can comprise holes for insertion of an anchoring pin or pins. In various techniques, such pins are extended through the openings 102a and into an anterior face of the tibia. The cutting block 84 can also include a probe 84 for aiding in referencing an anatomical landmark.

As described above, the posterior/anterior adjustment block 80 can be coupled to the cutting block 84 such that movement of the posterior/anterior adjustment block 80 causes similar or identical movement of the cutting block 84. For example, the cutting block 84 can comprise a cutting block guide rod 104. The guide rod 104 can extend from the upper, or proximal, portion of the cutting block 84, and can be sized and shaped so as to be received within the opening 105 of the posterior/anterior adjustment block 80. The opening 105 can extend through the posterior/anterior adjustment block 80 adjacent the posterior/anterior adjustment block hinge holes 98. This opening can receive the cutting block guide rod 104, and couple the anterior/posterior adjustment block 80 to the cutting block 84 to link movement between the posterior/anterior adjustment block 80 and cutting block 84. The cutting block 84, as well as other cutting blocks described herein, can in some embodiments be removably attachable to one or more components of an orthopedic fixture, and can be attached or removed at various stages of an orthopedic procedure.

5. Target Probes Which can be Used to Identify Anatomical Planes or Axes

Target probes can be provided for identifying anatomical planes and/or axes. For example, and with reference to FIGS. 2 and 20, the at least one target probe 18a, 18b, or other targets or devices, can comprise a structure for contacting an anatomical landmark and serving as a target for an emitted laser beam or beams from the surgical orientation device 12. For example, in a preferred arrangement, the at least one target probe 18a, 18b can comprise an elongate member 106 with an anatomical contact portion 107 and a target portion 108.

The anatomical contact portion 107 can comprise an end of the elongate member 106 or other structure configured to contact an anatomical feature, such as for example the lateral malleolus. The anatomical contact portion 107 can be held against the anatomical feature by hand, can be drilled into the anatomical feature, or can be held against and/or coupled with the anatomical feature in some another fashion.

Figure 20:
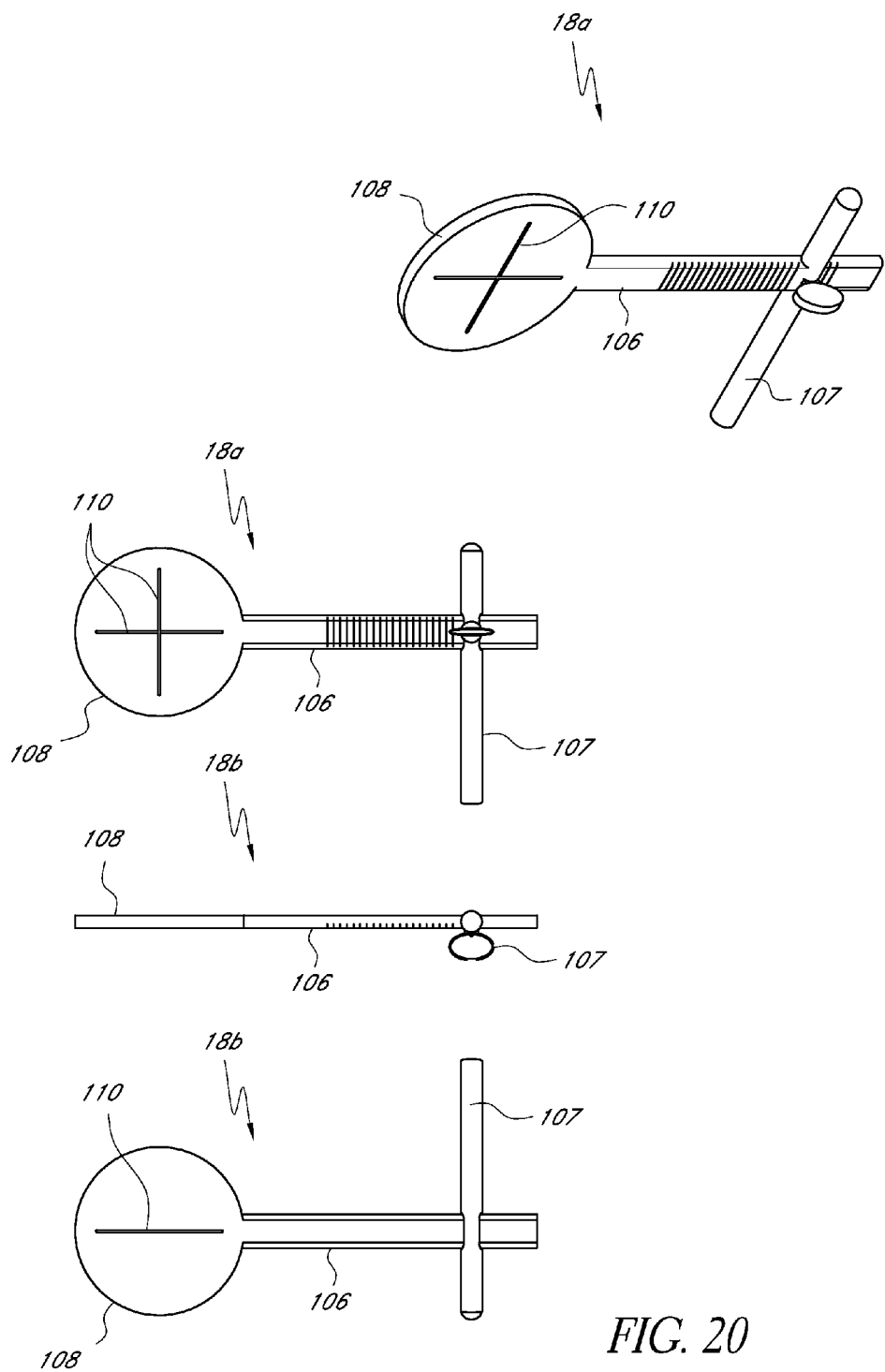
FIG. 20 is a perspective view of a set of target probes according to one embodiment which can be used in conjunction with the orthopedic fixture of FIG. 18.

The anatomical contact portion 107 can be connected to or integrally formed with the target portion 108. The target portion 108 can comprise an area on the target probe 18a, 18b which, as described further herein, is configured to indicate whether the target probe 18a, 18b is aligned with the surgical orientation device 12 and/or cutting block 84. For example, the target portion 108 can comprise one or more target shapes 110, in the form of markings, slits, or other structures. The target shapes 110, if for example in the form of slots, can be wide enough to allow a beam of laser light, such as for example a beam in the form of a plane or a cross-hair beam, to pass through the target shapes 110. FIG. 20 illustrates an embodiment of a target probe 18b with a target shape 110 in the form of a single slot, and a target probe 18a with two slots in the form of a cross, for example formed as two perpendicular lines or slots The target portion 108 can additionally be adjustable, such that as the anatomical contact portion 107 is held in place against the anatomical landmark, the target portion 108 can be moved relative to the anatomical landmark. For example, the target portion 108 can comprise a screw or other element which can be adjusted in order to change the length of the target probe 18a, 18b. In one embodiment, a device is provided to enable the position of the target portion 108 on the elongate member 106 to be adjusted. The device enables the target portion 108 to be moved closer to or away from the contact portion 106. Such adjustment provides one technique for aligning an orthopedic fixture, a surgical orientation device, or an orthopedic fixture and surgical orientation device, with a coronal or sagittal plane.

The target probes 18a, 18b can further include a marking or markings which indicate a current length of the target probe 18a, 18b, and/or indicate the degree or amount of adjustment which has been made to the target probe 18a, 18b. For example, the target portion 108 can comprise millimeter markings or other visual indicia corresponding to lengthwise offset along a length of the target portion 108, indicating adjustments in the length of millimeters.

In some embodiments, the target probes 18a, 18b shown in FIG. 20 can comprise the same target probe. Thus, FIG. 20 can illustrate opposite sides of the same target probe. For example, one side of the target probe can have a cross-hair target 110, and the other side of the target probe can have a single slot target 110.

6. Additional Sensors for Relative Movement

While the embodiment of the tibia preparation system 10 described above is described as having a sensor or sensors 40 located entirely within the surgical orientation device 12, in other embodiments the tibia preparation system 10, or other systems used for joint replacement and/or resection (e.g. for hip and shoulder), can include an additional sensor or sensors 40. These additional sensors 40 can be located on other surgical components and/or anatomical landmarks. U.S. Pat. No. 7,559,931 discloses examples of sensors on multiple surgical components and/or anatomical landmarks, and is herein expressly incorporated by reference and made a part of this disclosure. In one embodiment, the tibia preparation system 10 can include an additional sensor 40 located on the base member 78, or on the proximal tibia. The additional sensor 40 can include a microcontroller and/or communication device (e.g. infrared or other wireless technology (e.g. Bluetooth™)) which can relay information from the additional sensor 40 to the electronic control unit 1102 of the surgical orientation device 12. This additional sensor or sensors 40 can detect changes in movement of the tibia and/or leg during a knee replacement procedure, so as to verify whether the patient's leg (which typically is securely held in place during the procedure) has inadvertently or unintentionally moved in a varus/valgus, posterior/anterior, and/or other direction.

The electronic control unit 1102 can be configured to receive the information from this additional sensor or sensors 40, and/or the sensor's communications device, and combine that information with information from the sensor or sensors 40 located within the surgical orientation device 12 to calculate an overall, or aggregate, movement and orientation of the surgical orientation device 12 relative to an axial line or plane. The electronic control unit 1102 can correct for changes in position of this axis or plane, and the display 24 can indicate to the user an appropriate varus/valgus and/or flexion/extension angle for resection, based on the actual location of the mechanical axis or plane.

Additionally, this additional sensor or sensors 40 can be located in a device. The device can be constructed such that the device is autoclavable and reusable, and can allow insertion and removal of a disposable battery. The additional sensor or sensors 40 can be incorporated with any of the systems and/or methods described herein, and can be placed on any of the components of the systems described herein.

B. Acquiring Orientation Information Using a Visible Indicator and Target Probes

1. Pre-Operative Planning

Pre-operative planning can be used to prepare for a joint replacement procedure. For example, in a knee replacement procedure, the user can assess a desired varus/valgus angle and flexion/extension angle for resection of the tibia along a proximal portion of the tibia. This assessment can be made, for example, by clinical inspection (e.g. x-rays or manual visual inspection) of the knee prior to surgery. The pre-operative planning will usually determine what angle or angles of resection will be appropriate prior to attachment of the prosthetic knee component or components to the tibia.

The leg can then be secured by placement in a leg holder, and the knee can be exposed using a standard surgical procedure. Osteophytes on the proximal tibia can be removed, and a resection depth of the tibia can be determined by using a stylus or other instrumentation. For example, depth of resection can be determined by aligning the stylus length-wise, parallel with the tibia, with the depth of resection being determined by the point of contact between the tip of the stylus and the lowest point of a medial condyle of the proximal tibia. This resection depth can provide an indication to the user of what size prosthetic component or components to use, as well as how far to cut into the tibia with a cutting tool (e.g. saw blade).

2. Registering the Coronal and Sagittal Planes

After pre-operative planning for a joint replacement procedure, the tibial preparation system 10 described above can be used to identify the location and orientation of an axial line, as well as to orient a cutting block relative to the axial line.

For example, once the desired varus/valgus and posterior/anterior angles for resection have been determined pre-operatively, the tibial preparation system 10 can be assembled. The surgical orientation device 12, coupling mechanism 14, and universal jig 16 can be coupled together, and the tibial preparation system 10 can be positioned adjacent the proximal tibia on an anterior side of the tibia (i.e. front of the leg).

In a preferred arrangement, the tibial preparation system 10 can be positioned and/or moved until the surgical orientation device 12 is generally centered with the insertion of an anterior cruciate ligament and a medial tibial insertion of the patella tendon in a patient's knee. To achieve this centering, the surgical orientation device 12 can emit a laser beam or beams proximally from one of its optical components 32. This laser beam or beams can illuminate a portion of the knee joint, and the tibial preparation system 10 can be moved until the laser beam is aligned with at least one of the insertion of the anterior cruciate ligament and the medial tibial insertion of the patella tendon (e.g. the medial third of the tibial tuberosity). For example, if the optical component 32 emits a cross-hair beam, centering can be verified with a vertical portion (e.g. one which is parallel to or coincident with a sagittal plane extending through the leg) of the beam being aligned with both the insertion of the anterior cruciate ligament and the medial tibial insertion of the patella tendon.

Figure 21A:
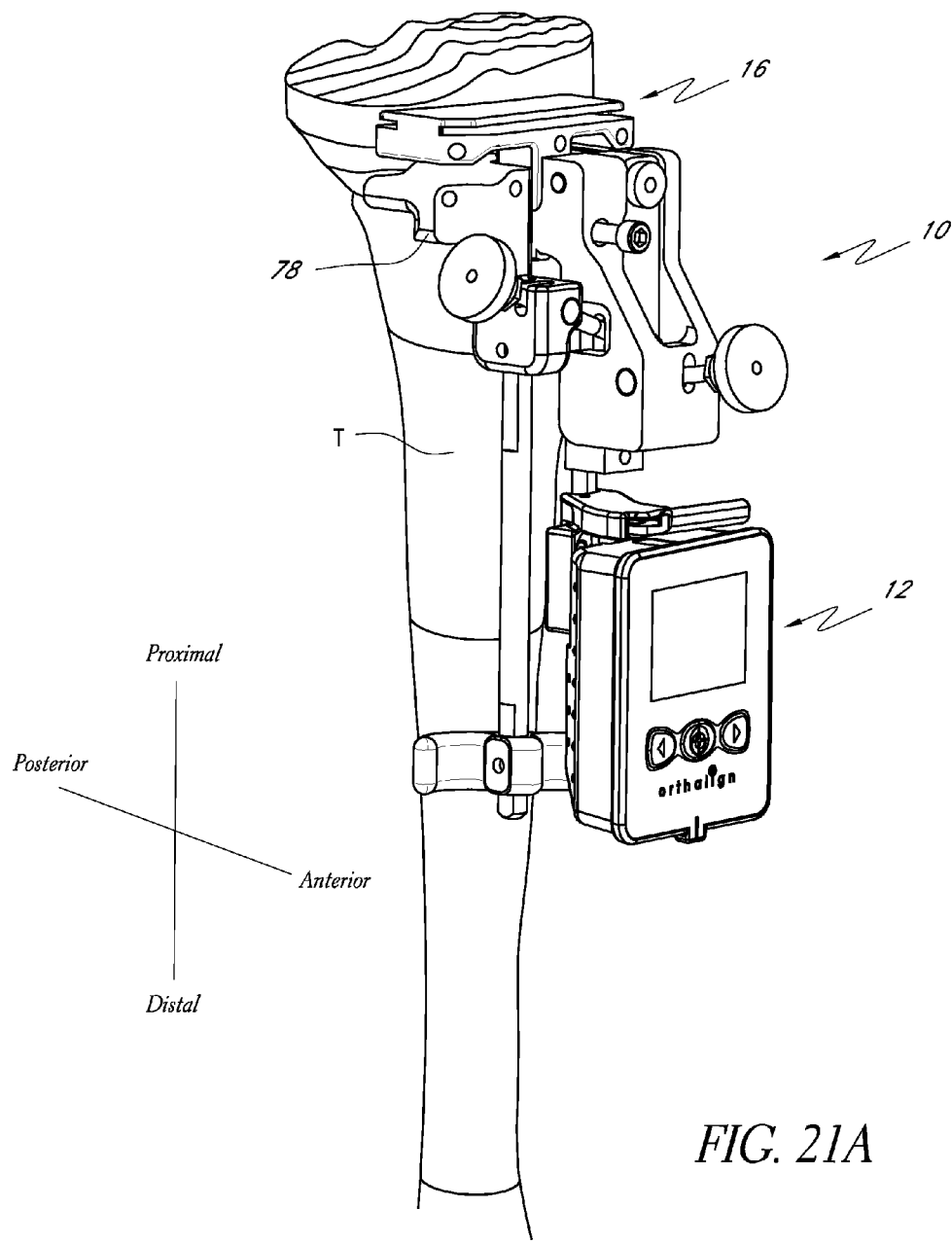
FIG. 21A is a perspective view of the tibial preparation system of FIG. 2A attached to the tibia.

With reference to FIG. 21a, once centering has been achieved, the base member 78 of the universal jig 16 can be coupled to or otherwise secured adjacent to a proximal portion of the tibia T. Preferably, the coupling securement is such that the base member 78 has zero or substantially zero degrees of freedom relative to the tibia T. In one technique, the base member 78 is pinned, which comprises placing at least one pin or other anchoring device through the holes 102a described above and into an anterior face of the tibia.

The user can then pick up and adjust locations of the target portions 108 of the target probes 18a, 18b. For example, the lengths of the target probes 18a, 18b can be adjusted to take into account a distance, which exists after attachment of the universal jig 16 to the tibia, between the optical element 32 of the surgical orientation device 12 and a mechanical axis of the leg.

Figure 21B:
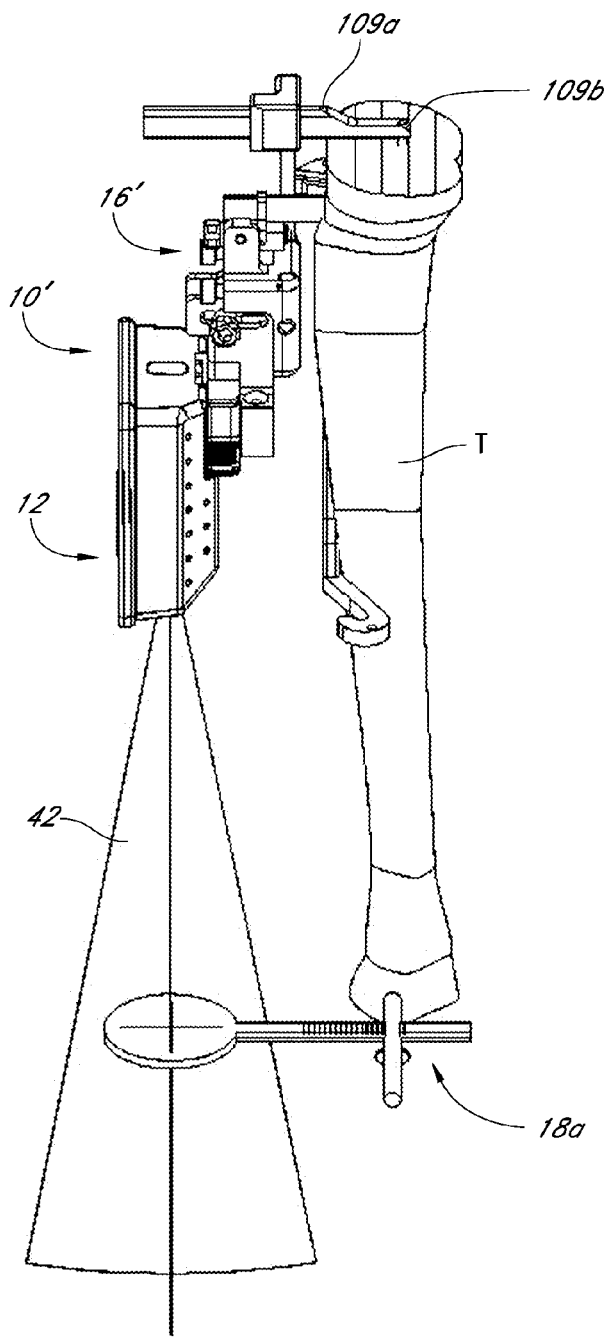
FIG. 21B is a perspective view of a tibial preparation system, as modified from the tibial preparation system of FIG. 2A, emitting laser light onto a target probe.

In a preferred arrangement, a stylus, marker pin, or other measuring device can be used to measure the distance between an A/P point on the proximal tibia and a plane parallel to a coronal plane containing the mechanical axis. This distance can be measured, for example, by referring to analogous numbering systems labeled on both the target probe 18a, 18b and the measuring device. For example, a FIG. 21b shows a tibial preparation system 10'. The tibial preparation system 10' is similar to the preparation system 10 described above, and includes the surgical orientation device 12 and a universal jig 16'. The measuring device 109, as shown in FIG. 21A, can be located proximal the cutting block 84 in a system 10 or 10'. The measuring device 109a can comprise etchings, or markings, to measure distance. The measuring device 109a can be moved, for example, until a tip 109b of the measuring device 109a is resting over the insertion point of the anterior cruciate ligament in the knee (for example as shown in FIG. 21B), and/or a soft point on the top of the tibia commonly referred to as the A/P point of the mechanical axis. This point is located along a tibial spine on top of the tibia, and generally marks the location of a point along the mechanical axis of the leg.

The user can use the measuring device 109a to measure the distance between the coronal plane containing the mechanical axis (including the A/P point) and, for example, the location of the optical element 32 on the surgical orientation device 12. Once this distance is known, the length of the target probes 18a, 18b can be adjusted until the target portions 108 are approximately the same distance anterior of a coronal plane containing the mechanical axis as is optical element 32 on the surgical orientation device 12.

In another embodiment, the distance between the optical element 32 of the surgical orientation device 12 and the coronal plane containing the mechanical axis can be measured directly with the target probe 18a, 18b itself (for example, using a target probe 18a, 18b that contains an adjustable marker), such that a desired length of the target portion 108 on the target probe 18a, 18b can be set directly.

Once the length of the target probe 18a, 18b is set, the user can palpate adjacent to a distal feature of the patient's tibia, such as for example the ankle, to find a location of the lateral malleolus. Once this location is found, the user can hold, couple, and/or affix a first target probe 18a adjacent to a distal feature of the patient's tibia, such as for example onto the lateral malleolus as shown in FIG. 21B.

The laser 42 can then be activated. FIG. 21b shows the tibial preparation system 10' with its laser 42 turned on. For example, an optical element 32 on the surgical orientation device 12 can be activated by pressing one of the user inputs 26 on the surgical orientation device 12, and can emit a crosshair laser beam distally toward the ankle, and toward the first target probe 18a.

With at least one cross-hair laser beam pointing towards the ankle, the knobs on the universal jig 16 can be adjusted until the laser beam illuminates a target shape 110 on the target portion 108 of target probe 18a. As described above, the target shape 110 can be a cross-shaped object, slot, cross mark, T-shaped, L-shaped, or some other shape containing perpendicular lines that meet or intersect. The user can adjust the position of the universal jig 16 until the crosshair beam of the laser beam lines up in both directions along or through the target shape 110.

In some embodiments, the target probe 18a, 18b can contain a sensor to detect feedback from the cross-hair beam of the laser and can be configured to emit noise or other feedback to confirm that the cross-hair beam of the laser has been positioned correctly on the target portion 108 of target probe 18a, 19b.

Once the cross-hair beam of the laser is aligned with the target shape 110, the user can input the orientation of the surgical orientation device 12 (and simultaneously cutting block 84), into the surgical orientation device 12 as a first reference position. For example, the user can press one of the user inputs 26 on the surgical orientation device 12, and the surgical orientation device 12 can register and/or calculate the current orientation of the surgical orientation device 12 based on data collected from the sensor or sensors 40. The orientation of the surgical orientation device 12 in this first reference position can be used to identify the orientation of a coronal plane that contains the mechanical axis of the leg. In one technique, data collected from the sensor 40 in connection with the probe 18a can also be used to determine a first reference point for identifying the location and/or orientation of a sagittal plane containing the same mechanical axis.

The user can then position a second target probe or probes 18b on the medial malleolus, the location of which may be determined by again palpating the ankle. Once the location of the medial malleolus is identified and the second target probe or probes 18b are held in place, the universal jig 16 can be adjusted until a beam of the cross-hair laser beam illuminates a desired target shape 110 on a second target probe 18.

Once the second target probe 18b has been positioned properly, the surgeon can again press one of the user inputs 26 on the surgical orientation device 12, and the surgical orientation device 12 can register and/or calculate the current orientation of the surgical orientation device 12 in the second reference position based on data collected from the sensor or sensors 40 inside the surgical orientation device 12. The orientation of the surgical orientation device 12 in this second reference position can be used to identify the orientation of a plane extending through the tibia which contains the mechanical axis of the leg, and/or can be used to locate a second reference point for identifying the location and/or orientation of a sagittal plane containing the mechanical axis.

When using the surgical orientation device 12 to determine the first and second reference positions, output of the sensors 40 in the surgical orientation device 12 can be monitored after light is directed to the selected location in a manner that minimizes error in the reading. For example, a transient phase can be eliminated in the output of the sensors 40 to arrive at an accurate estimation of the given anatomical landmark and/or target probe 18. The electronic control unit 1102 can be configured to perform stabilization algorithms or methods to minimize or substantially remove erroneous output caused by vibrational or other movements, as described above.

With continued reference to FIGS. 21a and 21b, once information about both the first and second reference positions has been acquired and registered in the surgical orientation device 12, the user can direct the surgical orientation device 12 to calculate the location of a desired point between the lateral malleolus and the medial malleolus. This desired point can lie within the aforementioned sagittal plane containing the mechanical axis. The desired point can vary, depending on the user's medical training and experience. For example, the desired point can be located midway between the lateral malleolus and medial malleolus, or 55% toward the medial malleolus from the lateral malleolus, or at some other predetermined location.

The user can use one or more user inputs 26 to provide commands to direct the surgical orientation device 12 to calculate the location of this desired point and to calculate the location and/or orientation of the sagittal plane containing this desired point. Once the surgical orientation device 12 has calculated where this desired point is, the surgical orientation device 12 can provide location feedback to the user, for example in the form of a visual signal or signals on the display 24, indicating that the location of this desired point, and/or the location of the sagittal plane, has been calculated.

In some embodiments, two target probes 18a can be used, each with a cross target 110. One of the target probes 18a can first be used to identify a coronal plane containing the mechanical axis, and both the target probes 18a can then be used to identify a sagittal plane containing the mechanical axis. Since the coronal plane can be registered by the first target probe 18a with a cross target 110, the user can line up a vertical portion of the cross-hair laser beam (e.g. one which is parallel or coincident with a sagittal plane extending through the leg) with the vertical portion of the second target probe 18a, and the location of the sagittal plane can be calculated. This alignment can be made without lining up both the horizontal and vertical portions of the cross-hair laser beam on the second target probe 18a, since doing so can cause the orientation of the surgical orientation device 12 to deviate from the already registered coronal plane.

3. Adjusting an Orthopedic Fixture to Set a Cutting Block Orientation

Once the location of the coronal and sagittal planes containing the mechanical axis has been acquired and registered by the surgical orientation device 12, the surgical orientation device 12 can calculate and store the location and orientation of the mechanical axis of the leg. Based on this stored information, the surgical orientation device 12 can be used to adjust the cutting block 84 in order to obtain a desired orientation for resection of the proximal tibia. For example, the universal jig 16, 16' can be adjusted to move the surgical orientation device 12.

With reference to FIG. 2, both a varus/valgus angle and posterior/anterior angle of the cutting block 84 can be set by the user. In order to adjust these angles of the cutting block 84, the user can turn the knobs 90a, 96a on the ends of pins 90 and 96 on the universal jig 16. Turning these knobs can change the angle and/or orientation of the varus/valgus adjustment block 82, and posterior/anterior adjustment block 80, respectively. As the varus/valgus adjustment block 82 and posterior/anterior adjustment block 80 are moved (e.g. rotated), the cutting block 84 can also be moved, along with the surgical orientation device 12.

As the cutting block 84 is moved (e.g. swung) in a varus/valgus direction, the surgical orientation device 12 can provide a reading or readings on its display 24 indicating whether the surgical orientation device (and likewise the cutting block 84) is aligned with the sagittal plane containing the mechanical axis, or whether the cutting block 84 is angled at some degree relative to the sagittal plane containing the mechanical axis. For example, the surgical orientation device 12 can indicate on its display 24 a difference in degrees between the current orientation of the cutting block 84, and an orientation of the cutting block 84 in which the cutting block 84 is aligned substantially or exactly parallel to (or exactly on) the sagittal plane containing the mechanical axis.

Similarly, as the cutting block is moved (e.g. swung) in a posterior/anterior direction, the surgical orientation device 12 can provide a reading or readings on its display 24 indicating whether the surgical orientation device (and likewise the cutting block 84) is aligned with the coronal plane containing the mechanical axis, or whether the cutting block 84 is angled at some degree relative to the coronal plane containing the mechanical axis. For example, the surgical orientation device 12 can indicate on its display 24 a difference in degrees between the current orientation of the cutting block 84, and an orientation of the cutting block 84 in which the cutting block 84 is aligned substantially or exactly parallel to the coronal plane containing the mechanical axis.

In some embodiments, the cutting block 84, or other cutting blocks described herein, can be attached to a universal jig after the universal jig has been adjusted. Thus, the final position of the cutting block can be adjusted, and the cutting block can then be attached, as opposed to being attached during the entire adjustment process.

Figure 22A:
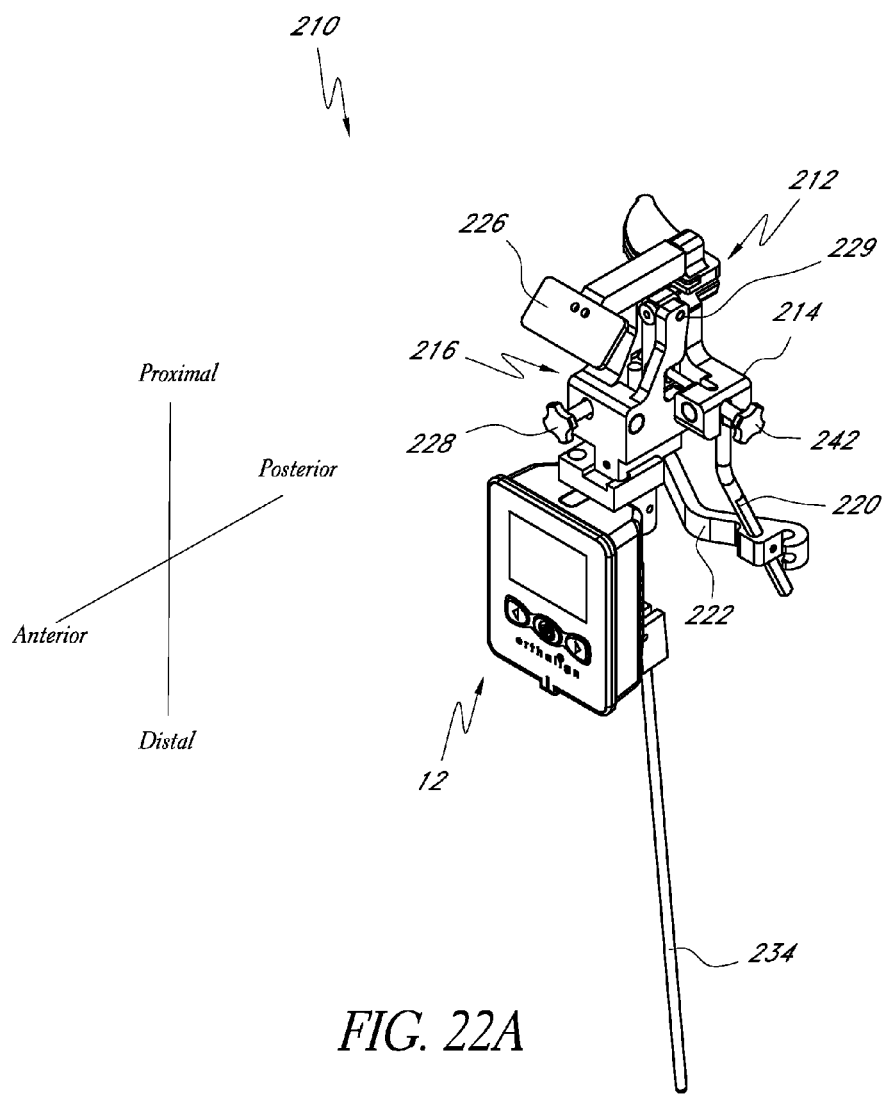
FIG. 22A is a perspective view of the tibial preparation system of FIG. 2B.

The surgical orientation device 12 can further be useful in setting and/or confirming a resection depth of the tibia once the varus/valgus and posterior/anterior angles have been determined. For example, in a preferred arrangement, the user can activate the laser 42 (e.g. a proximal cross-hair beam laser) on the surgical orientation device 12 by pressing one of the user inputs 26, and can hold or attach a device for confirming a cut line or plane, for example a mirror 226 as shown in FIG. 22A of the system 210. The mirror 226 can be coupled to or integrally formed with the universal jig 16 or other surgical component. The mirror 226 can be held or attached at a certain angle such that a horizontal beam of the cross-hair beam, extending, for example, parallel to a coronal plane, is reflected through an opening 102 on the cutting block 84 and onto the tibia, illuminating an area on the tibia which a cutting saw would cut through if moved through the cutting block 84. The points of bone on the tibia which prevent the passage of the laser beam (and which are therefore illuminated by the laser) across the tibia are those which would be resected by the cutting saw. In the event that a different depth of the resection is desired, the user can adjust the cutting block 84 and reconfirm depth of resection.

C. Tibial Preparation System with Mechanical Referencing of a Distal Landmark

Figure 2B:
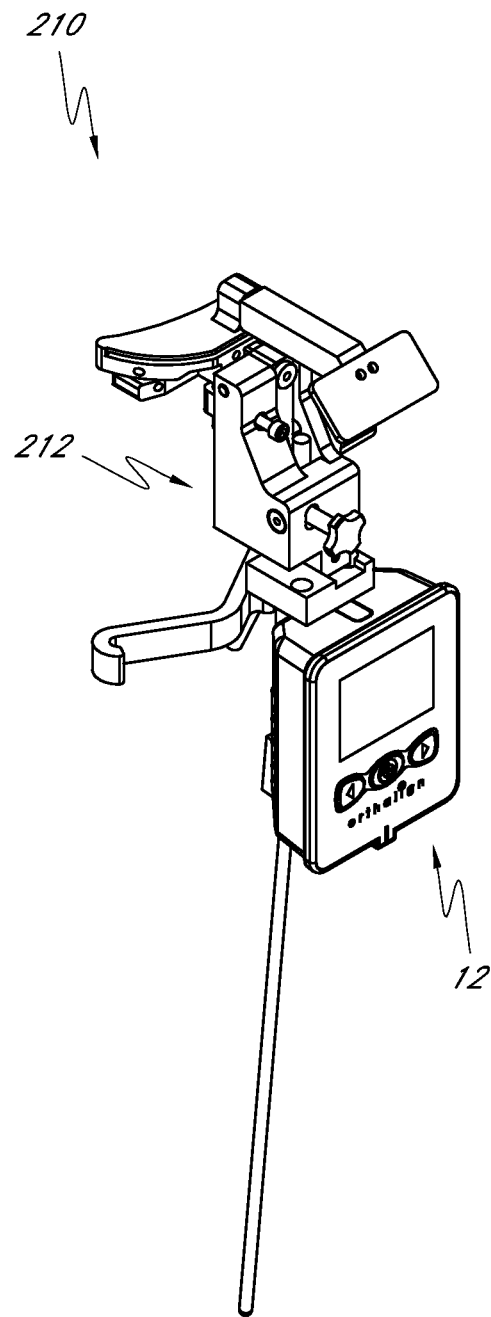
FIG. 2B is a perspective view of another tibial preparation system according to one embodiment that can be used in connection with preparation of an aspect of a knee joint during a knee joint replacement procedure.

A tibia preparation system can be provided which uses a moveable orthopedic fixture with a probe to reference one ore more anatomical landmarks mechanically. The probe can comprise a mechanical swing arm. For example, FIGS. 2b and 22-23 illustrate a tibial preparation system 210. Tibial preparation system 210 is a variation on the tibial preparation system 10 described above, and can comprise the surgical orientation device 12 described above, as well as a universal jig 212. The tibial preparation system 210 can differ from the tibial preparation system 10, for example, in that the system 210 can utilize a mechanical structure or structures to locate anatomical landmarks adjacent the distal tibia, as opposed to using a target or targets with a light source as described above.

Figure 22B:
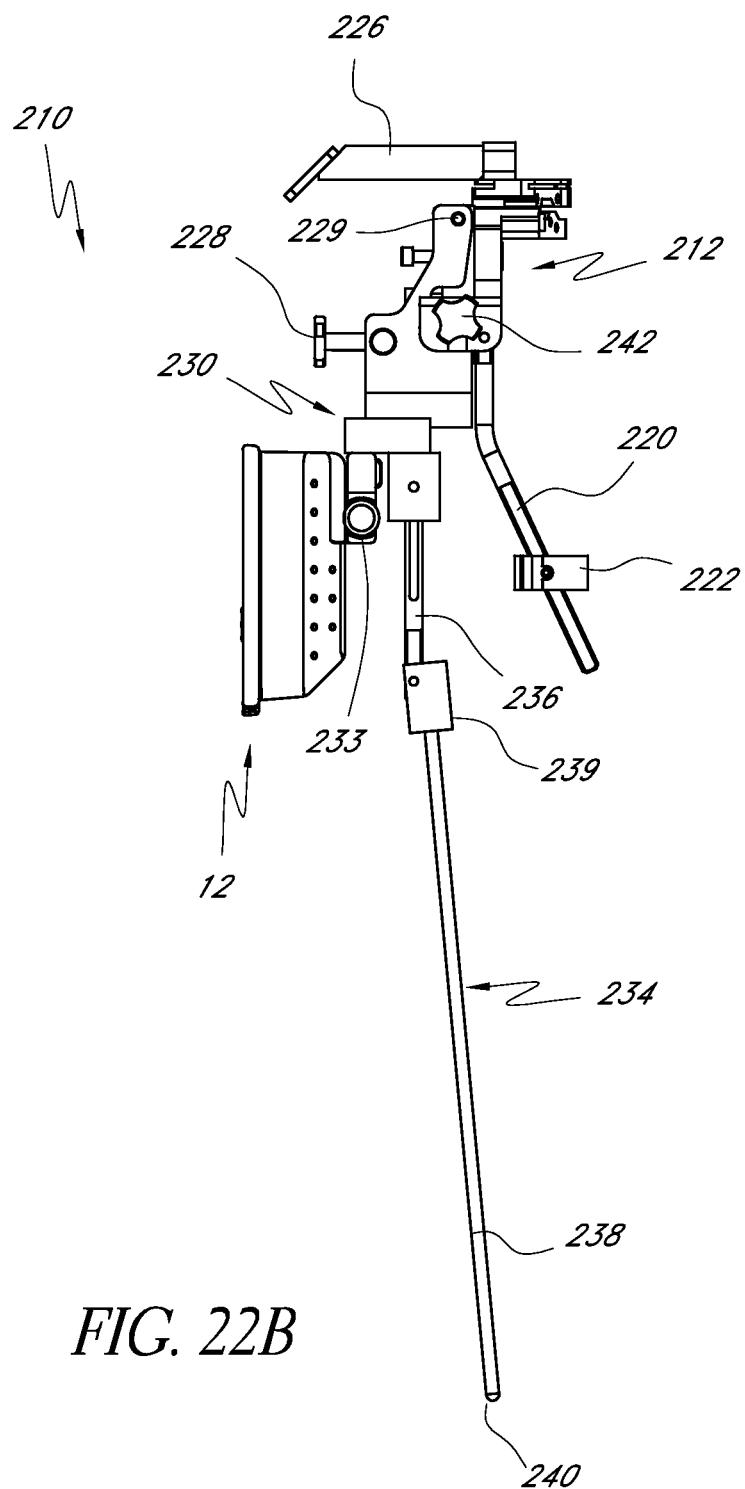
FIG. 22B is a side view of the tibial preparation system of FIG. 2B.
Figure 22C:
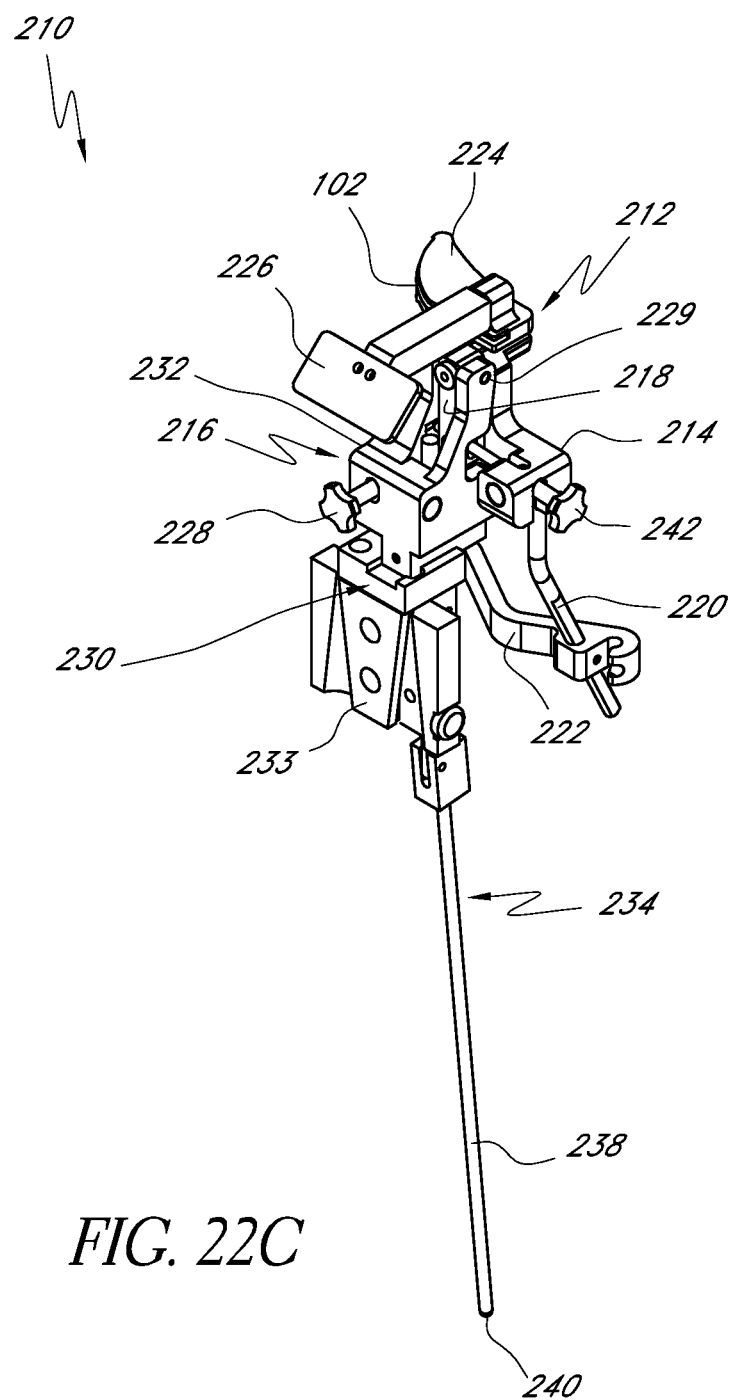
FIG. 22C is a perspective view of the tibial preparation system of FIG. 2B, without a surgical orientation device attached.

1. Orthopedic Fixture for Orienting a Surgical Orientation Device and/or Cutting Block in Multiple Degrees of Freedom An orthopedic fixture can be provided for orienting a surgical orientation device and/or cutting block. For example, the universal jig 212 can be similar to the universal jig 16 described above. With reference to FIGS. 22A-C, the universal jig 212 can comprise a base member 214 operatively coupled to a posterior/anterior adjustment block 216, and/or a varus/valgus adjustment block 218.

a. Base Member for Providing an Anchored or Fixed Initial Position of an Orthopedic Fixture A base member can be provided which anchors an orthopedic fixture and/or provides a fixed initial position of a moveable orthopedic fixture. For example, the base member 214 can comprise a structure which is rigidly and/or fixedly attached to an anatomical structure, such as a bone. In a preferred arrangement, the base member 214 can comprise a proximal mounting structure, such as for example at least two base member attachment openings (not shown) which are in the form of holes extending through the base member 214. Each of the base member attachment openings can be configured to receive a fastening device, such as for example a screw, to anchor the base member 214 into a bone or other anatomical structure and fix the base member 214 relative to the bone or anatomical structure. For example, the base member 214 can be mounted on a proximal portion of the tibia.

The base member 214 can further comprise an elongate base member rod 220, similar to rod 92 described above. The elongate base member rod 220 can extend distally from an upper, or proximal, portion of the base member 214, and can include a brace-like structure 222 on its distal end, similar to structure 94 described above. The brace-like structure 222 can be curved to better conform to the curvature of the anatomy. The brace-like structure 222 can be used to brace and/or hold the universal jig 212 against the patient's skin overlying the tibia during the knee replacement procedure. For example, and as described above, the brace-like structure 222 can provide a stabilizing force.

Similar to the system 10, the base member 214 can be operatively connected to a cutting block 224, as described further herein. The cutting block 224 can be located proximal the base member 214, and can move relative to the base member 214.

The base member 214 can further comprise a device for confirming a cut line or plane, as described above. For example, the base member can comprise a mirror 226. The mirror 226 can be formed as part of the cutting block 224, or other surgical component. The mirror 226 can comprise a 45 degree (or other angle) reflective surface, which can reflect a light beam or beams along the surface of an anatomical feature. For example, and as described above, the mirror 226 can be angled and/or fixed such that a beam of a cross-hair laser beam is reflected through an opening 102 on the cutting block 224 and onto the tibia, illuminating an area on the tibia which a cutting saw would cut through if moved through the cutting block 224.

b. Device for Adjusting a Posterior/Anterior Slope of a Cutting Block

An adjustment device can be provided which can be used to adjust the orientation of a surgical orientation device and/or cutting block. For example, and with continued reference to FIGS. 22 and 23, a posterior/anterior adjustment block 216 can comprise a structure that is moveable (e.g. rotatable) in at least one of a posterior and anterior direction. For example, the universal jig 212 can include at least one knob 228. When the knob 228 is turned, the posterior/anterior adjustment block 216 can rotate about a hinge, pin, or other structure, such as for example pin 229, in the universal jig 212 to change a posterior/anterior angle of the cutting block 224. As discussed further below, the surgical orientation device 12 can be coupled to the adjustment block 216 for movement therewith. Thus, movement of the adjustment block 216 can also change the plane angle of the surgical orientation device 12.

The posterior/anterior adjustment block 216 can further comprise a connector 230. The connector 230 can comprise a structure which operatively connects the posterior/anterior adjustment block 216 to the surgical orientation device 12. For example, the connector 230 can comprise a structure which facilitates translational movement of the surgical orientation device 12 relative to the posterior/anterior adjustment block 216. The connector 230 can comprise a channel 231. The channel 231 can facilitate movement of an upper, or proximal, portion 232 of the posterior/anterior adjustment block 216 relative to the connector 230 (e.g. sliding movement).

With reference to FIGS. 22b and 23, the connector 230 can comprise, or be attached to, a clamp 233. The clamp 233 is a coupling device similar to the coupling device 14 described above. For example, the clamp 233 can be secured to the back side of the surgical orientation device 12 to couple the surgical orientation device 12 to another structure or structures. In the tibia preparation system 210, the clamp 233 can be used to couple the surgical orientation device 12 to the posterior/anterior adjustment block 216.

With reference to FIGS. 22-23, the connector 230 can further comprise, or be attached to, a swing arm 234. The swing arm 234 can comprise a landmark acquisition device which can be used to locate and/or identify specific landmarks, such as for example landmarks adjacent the distal tibia. The swing arm 234 can comprise an elongated structure or structures, such as for example a metal rod or rods, which can extend from a proximal portion of the tibia (e.g. near the knee joint) to a distal portion of the tibia (near the ankle). The swing arm 234 can extend generally vertically (e.g. in a proximal to distal direction) behind the surgical orientation device 12, and/or can be hinged, such that at least one of a distal portion 236 and proximal portion 238 of the swing arm 234 can swing and/or rotate relative to the other proximal or distal portion 236, 238. For example, the distal and proximal portions 236, 238 can comprise elongate structures connected by a hinge portion 239 located between the distal and proximal portions 236, 238. The hinge portion 239 can permits relative movement of the distal portion 236 with respect to the proximal portion 238. In other embodiments the swing arm can comprise more than one hinge portion 239. The hinge portion or portions 239 can be located at other locations than that shown in FIGS. 22a, 22b, and 23. The swing arm 234 can also comprise a distal end 240. The distal end or tip 240 can comprise a pointed structure or structures, and/or a distal mounting structure, which can contact and/or couple with an anatomical landmark. For example, the hinge portion 239 of the swing arm 234 can be moved or swung until the tip 40 is in contact with, or is coupled to, an anatomical landmark adjacent the distal tibia.

Similar to the universal jig 16 described above, the posterior/anterior adjustment block 216 of universal jig 210 can be operatively connected to the cutting block 224. Movement of the posterior/anterior adjustment block 216 and cutting block 224 can be linked (e.g. by pins, hinges, etc.) such that movement of the posterior/anterior adjustment block 216 can cause similar or identical movement of the cutting block 224. Movement of the cutting block 224 can, at the same time, cause similar or identical movement of the surgical orientation device 12.

While the swing arm 234 is described as forming part of the posterior/anterior adjustment block 216, the swing arm 234 can alternatively be formed as part of the base member 214 and/or varus/valgus adjustment block 218 described below. Similarly, while the base member 214 is described as being separate from the posterior/anterior adjustment block and varus/valgus adjustment block 218, the base member can, in at least some embodiments, refer generally to a combination or combinations of the posterior/anterior adjustment block 216, swing arm 234, and/or varus/valgus adjustment block 218.

c. Device for Adjusting a Varus/Valgus Slope of a Cutting Block

An adjustment device can be provided which can be used to adjust the orientation of a surgical orientation device and/or cutting block. For example, and with continued reference to FIGS. 22A-C, the varus/valgus adjustment block 218 can comprise a structure which is moveable (e.g. rotatable) in at least one of a varus/valgus direction. For example, the universal jig 212 can include at least one knob 242. When the knob 242 is turned, the varus/valgus adjustment block 218 can rotate about a hinge, pin, or other structure in the universal jig 212 to change a varus/valgus angle of the surgical orientation device 12, as well as the cutting block 224.

Movement of the varus/valgus adjustment block 218 can correspond to or result in movement of the posterior/anterior adjustment block 216. For example, a portion or portions of the varus/valgus adjustment block 218 can rest within and/or be contacted on either side by portions of the posterior/anterior adjustment block 216, such that any movement of the varus/valgus adjustment block 218 in a varus or valgus direction likewise causes similar or identical varus/valgus movement of the posterior/anterior adjustment block 216.

d. Cutting Block Which can be Oriented in a Posterior/Anterior, and/or a Varus/Valgus, Direction for Bone Resection A cutting block, or other orthopedic fixture, can be provided for bone resection. The cutting block can be oriented with the aid of a surgical orientation device, an orthopedic fixture, or a surgical orientation device and an orthopedic fixture. The cutting block 224, as described above, can comprise at least one opening 102. For example, one opening 102 can comprise an elongate slit along a width of an upper, or proximal, portion of the cutting block 224 for receiving and guiding a saw, blade, or other cutting tool. Other openings 102a (not shown) can comprise holes for insertion of an anchoring pin or pins, or other structures.

2. Modified Orthopedic Fixture

Figure 23A:
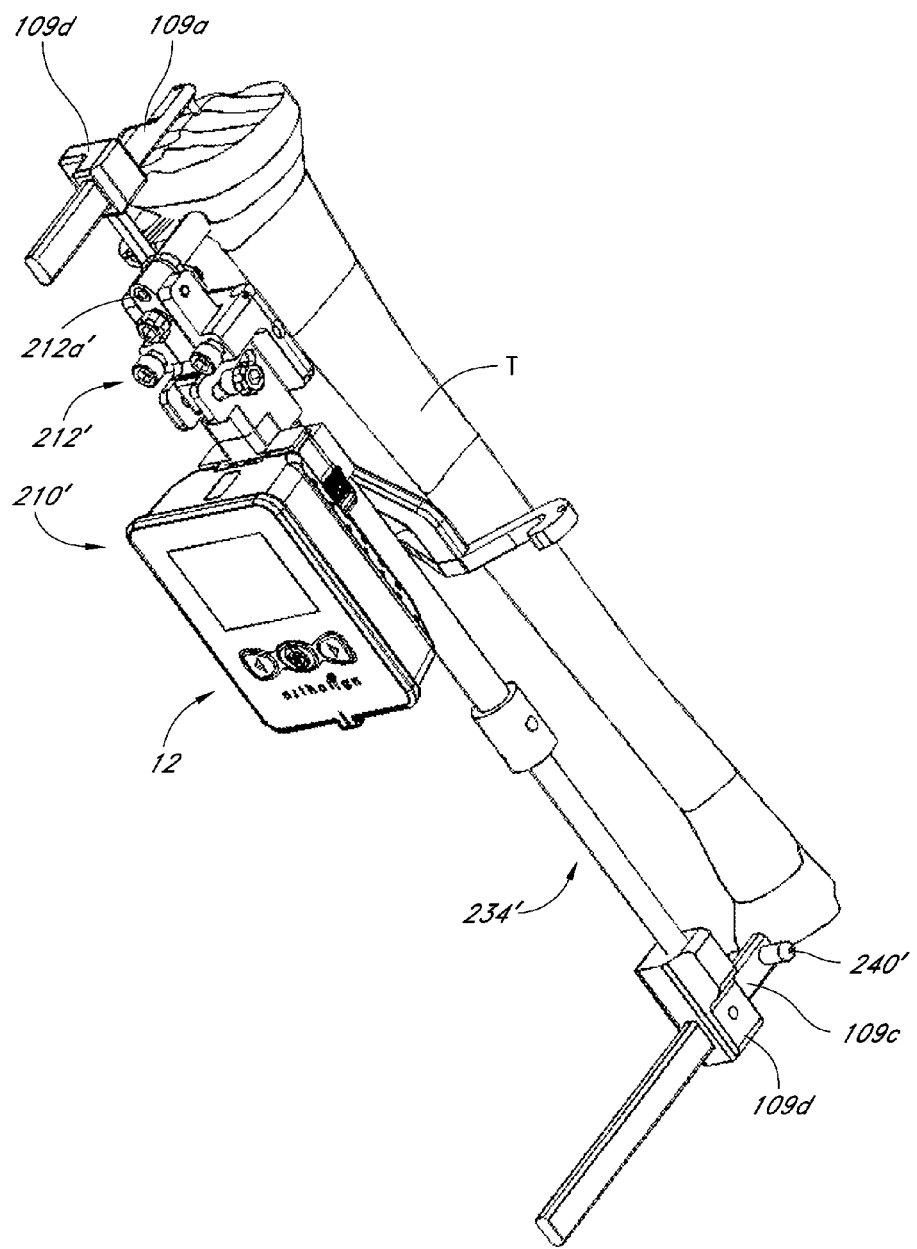
FIG. 23A is a perspective view of a tibial preparation system, as modified from the tibial preparation system of FIG. 2B, showing measuring devices.
Figure 23B:
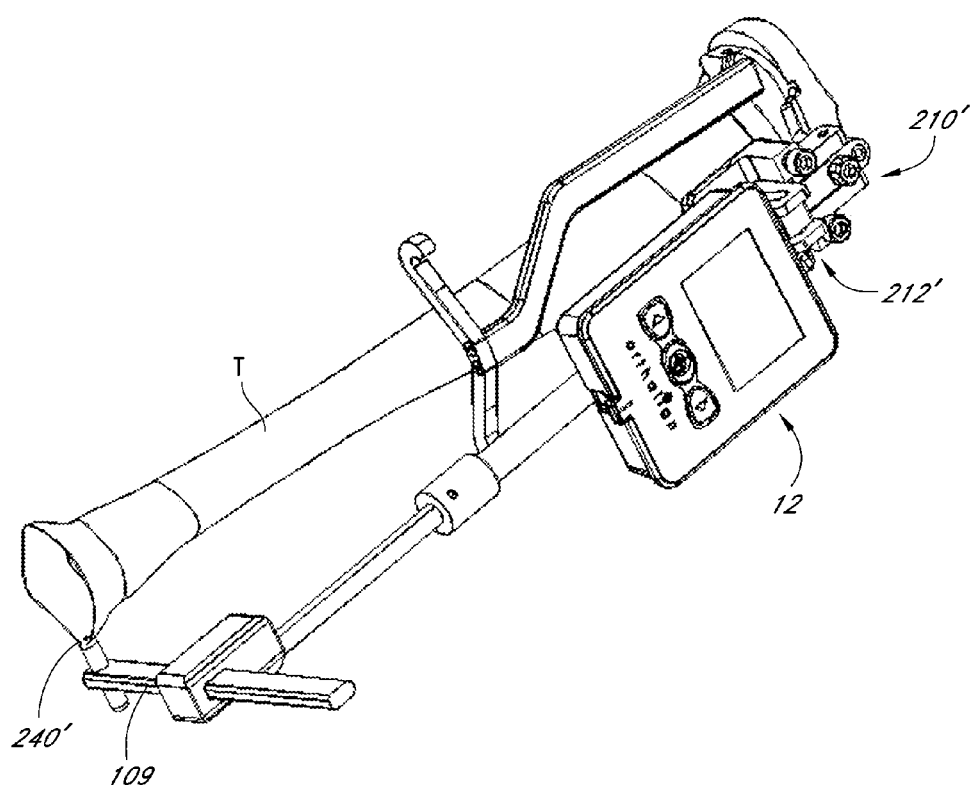
FIG. 23B is a perspective view of the tibial preparation system of FIG. 23A being used to reference an anatomical landmark.

The system 210 described above can be modified. For example, FIGS. 23A and 23B show a system 210'. The system 210' is a modification of system 210, and can comprise a universal jig 212' similar to the jig 212 described above. The system 210' can also comprise a surgical orientation device 12. The universal jig 212' can be adjusted by moving (e.g. pivoting) a swing arm 234' by hand about a proximal portion 212a of the universal jig 212', rather than adjusting knobs by hand. The proximal portion 212a can comprise a varus/valgus adjustment device (such as the one described above), a posterior/anterior adjustment device (such as the one described above), and/or a pivot pin or pins. Knobs can be included for locking the swing arm 234' in place. In some embodiments the universal jig 210' can comprise knobs for fine-tune adjusting. In one embodiment, the swing arm 234' can comprise an extendable portion that enables a distal portion thereof to be extended away from a base portion. The distal portion can include a moveable rod extendable from another member (e.g., a hollow rod) that is fixed to the base. The distal portion can be fastened in any of a range of positions relative to the fixed, proximal portion. The distal portion preferably can be clamped in a range of positions. In one embodiment a distal portion of the swim arm 234' can be coupled with a block to enable adjustment of a tip into contact with anatomical landmarks. In some embodiments, the jig 212' can be coupled with a proximal tibia and the arm 234' is adapted to contact lateral or medial malleolus. In some embodiments, the jig 212' can be coupled with a distal femur and the arm 234' is adapted to contact a structure corresponding to a femoral head, a lesser trochanter or a greater trochanter, as discussed herein.

With reference to FIG. 23A, the modified system 210' can comprise a measuring device 109a, and a measuring device 109c. As described above with respect to system 10, the measuring device 109a can be used to measure a distance between an A/P point along the top of the tibia and a coronal plane parallel to the coronal plane containing the mechanical axis. The measuring device 109a can include a marking or markings providing a visual indication of distance, and can slide within a block 109d. The measuring device 109c can also measure a distance, and can include a marking or markings to provide a visual indication of distance.

D. Acquiring Orientation Information Using Mechanical Referencing of a Distal Landmark 1. Registering the Coronal and Sagittal Planes After pre-operative planning for a joint replacement procedure, the tibial preparation system 210, 210' described above can be used to identify the location and orientation of an axial line, as well as to orient a cutting block relative to the axial line.

For example, once the desired varus/valgus and posterior/anterior angles for resection have been determined pre-operatively for a knee replacement procedure as describe above, the tibial preparation system 210, 210' can be provided. In one technique at least some of the components are modular, enabling using such component with multiple other orthopedic components. As such, the tibial preparation system 210, 210' can be assembled from these components.

The surgical orientation device 12 can be coupled to the universal jig 212, and the tibial preparation system 210, 210' can be positioned adjacent the proximal tibia on an anterior side of the tibia (i.e. front of the leg). In other techniques, the tibial preparation system 210, 210' is partially or completely pre-assembled or integrated.

In a preferred arrangement, the tibial preparation system 210, 210' can be positioned such that the surgical orientation device 12 is generally centered with the insertion of an anterior cruciate ligament and a medial tibial insertion of the patella tendon in a patient's knee, for example as described above with respect to tibial preparation system 10. Once centering has been achieved, the base member 214 of the universal jig 212, 212' can be pinned, anchored, and/or otherwise secured to the tibia, such that the base member 214 has zero or substantially zero degrees of freedom relative to the tibia.

The user can then slide the connector 230 in a posterior and/or anterior direction (e.g. translate the connector 230 forwards or backwards), until the swing arm 234, 234' is located proximate an anatomical landmark. For example, the connector 230 can slide until the tip 240 of the swing arm 234, 234' is located adjacent the lateral malleolus on the patient's ankle. The lower, or distal, portion 238 can swing and/or rotate during such movement in order to get the tip 240 closer to the lateral malleolus.

In a preferred arrangement, measuring devices 109a and 109c, such as the ones illustrated in system 210', can be used. For example, one measuring device 109a can be located proximal the universal jig 212 or 212', and another measuring device 109c can be located at a distal end of the swing arm 234 or 234'.

The measuring devices 109a can be moved until a tip of the measuring device 109a is resting over the insertion point of the anterior cruciate ligament in the knee; and/or a soft point on the top of the tibia commonly referred to as the A/P point of the mechanical axis. As described above, this point is located along a tibial spine on top of the tibia, and generally marks the location of a point along the mechanical axis of the leg.

The measuring device 109c can then be moved until a tip 240 or 240' is positioned next to the lateral malleolus (for example as shown in FIG. 23B). For example, the user can palpate adjacent to a distal feature of the patient's tibia, such as for example the ankle, to find a location of the lateral malleolus of the tibia. Once this location is found, the user can position the tip 240, 240' of the swing arm 234, 234' adjacent to a distal feature of the patient's tibia, such as onto the lateral malleolus as shown in FIG. 23B.

The measuring devices 109a, 109c can then be adjusted until portions 109d are approximately the same distance anterior of a coronal plane containing the mechanical axis, placing the surgical orientation device 12 in an orientation parallel to that of the coronal plane containing the mechanical axis. Each measuring device 109a, 109c can have analogous numbering systems. For example, the measuring devices 109a, 109c can comprise etchings, or markings.

The user can activate the surgical orientation device 12, such as by pressing one of the user inputs 26 on the surgical orientation device 12. Once activated, the, surgical orientation device 12 can register (e.g. record) the orientation of the surgical orientation device as a first reference position. For example, the surgical orientation device 12 can register and/or calculate the current orientation of the surgical orientation device 12 based on data collected from the sensors 40. The orientation of the surgical orientation device 12 in this first reference position can be used to identify and register the orientation of a coronal plane which contains the mechanical axis of the leg, as well as to determine a first reference point for identifying the location and/or orientation of a sagittal plane containing this same mechanical axis.

The user can then swing the swing arm 234, 234' over to the other (e.g. medial) side of the leg, such that the tip 240, 240' is located adjacent the medial malleolus. For example, the user can turn the knob 242 on system 210 so that the posterior/anterior adjustment block 216, connector 230, and swing arm 234 are moved in a varus/valgus manner, until the swing arm 234 has moved to the other side of the leg. The lower, or distal, portion 238 of the swing arm 234 can swing and/or rotate during such movement in order to avoid hitting or contacting the an anterior side of the leg.

The user can then again palpate the ankle, and position the tip 240, 240' of the swing arm adjacent to the medial malleolus. Once the location of the medial malleolus is identified, the user can press one of the user inputs 26 on the surgical orientation device 12 to cause the surgical orientation device 12 to determine the orientation of the surgical orientation device 12 in a second reference position. For example, the surgical orientation device 12 can register and/or calculate the current orientation of the surgical orientation device 12 based on data collected from the sensors 40.

The orientation of the surgical orientation device 12 in this second reference position can be again be used to identify the orientation of a coronal plane extending through the tibia that contains the mechanical axis of the leg; and/or can be used to locate a second reference point for identifying the location and/or orientation of a sagittal plane containing the same mechanical axis.

When using the surgical orientation device 12 to determine the first and second reference positions, output of the sensors 40 in the surgical orientation device 12 can be monitored in a manner that minimizes error in the reading. For example, a transient phase can be eliminated in the output of the sensors 40 to arrive at an accurate estimation of the given anatomical landmark as discussed above.

Once information about both the first and second reference positions has been acquired and registered in the surgical orientation device 12, the surgical orientation device 12 can determine (e.g. calculate) the location of a desired plane between the lateral malleolus and the medial malleolus. As described above, the desired plane corresponds to the sagittal plane containing the mechanical axis. The desired plane can vary, depending on factors such as the patient's specific anatomy and the surgeon's training and experience. For example, the desired plane can be located midway between the lateral malleolus and medial malleolus, or 55% toward the medial malleolus from the lateral malleolus, or at some other predetermined location.

The user can use one or more user inputs 26 to direct the surgical orientation device 12 to calculate the location of and/or orientation of the sagittal plane. Once the surgical orientation device 12 has calculated where the sagittal plane is, the surgical orientation device 12 can provide location feedback to the user, for example in the form of a visual signal or signals on the display 24, indicating that the location of the sagittal plane has been calculated.

2. Adjusting an Orthopedic Fixture to Set the Orientation of a Cutting Block

Once the locations of the coronal and sagittal planes containing the mechanical axis have been acquired (e.g. registered) by the surgical orientation device 12, the surgical orientation device 12 can calculate and store the location and orientation of the mechanical axis of the leg. Based on this stored information, the surgical orientation device 12, and universal jig 212, 212', can be used to adjust a cutting block in order to obtain a desired orientation for resection of the top of the tibia.

For example, and as described above with respect to tibial preparation system 10, the knob or knobs 90a, 96a on the universal jig 212 can be turned to set a desired varus/valgus and posterior/anterior angle for resection. During this adjustment, the surgical orientation device 12 can provide a reading or readings on its display 24 indicating whether the surgical orientation device (and likewise the cutting block 224) is aligned with the sagittal plane and/or coronal plane containing the mechanical axis, or whether the cutting block 224 is at an acute angle relative to the sagittal plane and/or coronal plane containing the mechanical axis.

Once the orientation of the cutting block 224 has been adjusted and set, the mirror 226 can be used. For example, the user can press one of the user inputs 26 on the surgical orientation device 12 to direct a laser beam out of the optical element 32 and onto the mirror 226. The laser beam can be reflected through an opening 102 on the cutting block 224 and onto the tibia, illuminating an area on the tibia for resection through the cutting block 224. The points of bone on the tibia illuminated by the laser are those which would be resected by the cutting saw. In the event that a different depth of the resection is desired, the user can adjust the cutting block 224 and reconfirm depth of resection.

E. Other Target Systems and Methods

While the tibial preparation systems 10, 10', 210, and 210' and their methods of use are described above specifically in terms of a system that incorporates a surgical orientation device 12, a universal jig 16 or 212, a laser system, and/or a set of target probes 18 or swing arm 234, in other embodiments other components can be used to determine anatomical planes on the human body and/or facilitate alignment of surgical devices, systems, and/or anatomical parts.

For example, a light system other than a laser system can be attached to a surgical orientation device that is otherwise similar to the surgical orientation device 12 described above. A user can position the surgical orientation device until the light is illuminating a target, such as for example an anatomical landmark, and the surgical orientation device can acquire this first position as a reference. The user can then position the device until the laser is illuminating another anatomical landmark and the surgical orientation device can acquire this second position as a reference. Third, fourth, and/or additional reference positions can also be obtained in the same technique.

The surgical orientation device can employ an algorithm that calculates some appropriate point (e.g. a midpoint), as directed by the user, between the two anatomical landmarks that corresponds to the position of a desired anatomical plane. The surgical orientation device can also provide feedback to the user to position the surgical orientation device in alignment with this plane. Alternatively, if a desired plane or axis can be determined based on the position of one, two, three, or more anatomical landmarks, a system can be used to make such determination based on a light-mapping of such landmark(s) and corresponding calculations performed by a surgical orientation device.

In some embodiments, the surgical orientation device 12, or other surgical orientation device, can be held at some distance from the body by the user. The surgical orientation device 12 can be used as a registration guide. For example, the user can activate a light system on the surgical orientation device that illuminates a line along the body, such as for example along the mechanical axis. Once the line is visibly aligned along the mechanical axis, the surgical orientation device can press a user input 24 and the surgical orientation device can register an orientation of the surgical orientation device. This orientation information can later be used to align orthopedic fixtures or cutting blocks.

In some embodiments, the target systems described herein, or other target systems, can be used to locate targets on the hip, femur, or other areas of the body, and to use such targets to acquire planes or axes extending through the body. For example, the universal jig 16 can be attached on the femur, and the system 10, including target probes 18*a*, 18*b* described above, can be used to locate landmarks such as the greater trochanter, center of the head of a femur, a point of entrance of a ligament, or other landmarks, and use these landmarks to reference an anatomical plane or planes. Similarly, the universal jig 212 can be attached on the femur, and the system 210, including swing arm 234' can be used to reference an anatomical plane or planes.

Figure 3A:
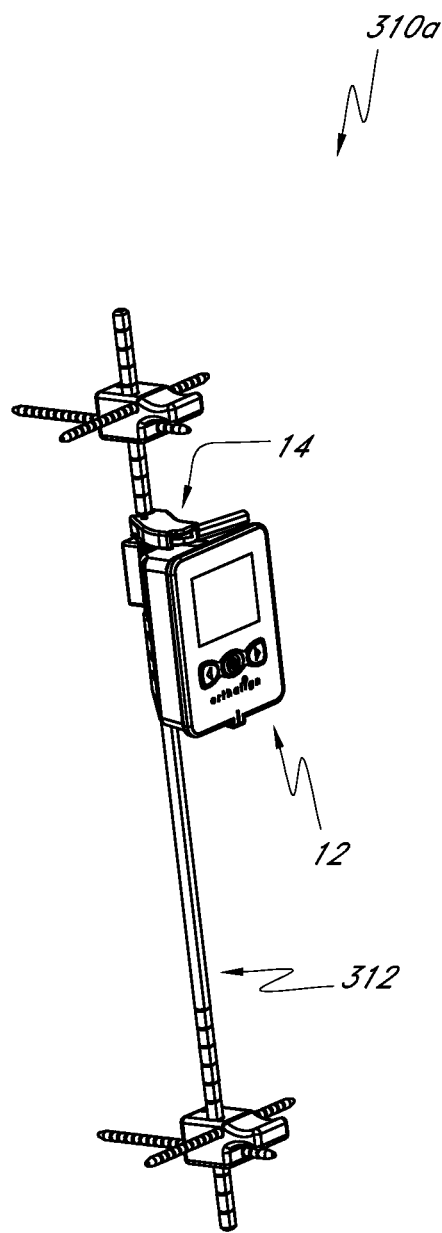
FIG. 3A is a perspective view of a first arrangement of another tibial preparation system according to one embodiment that can be used in connection with preparation of an aspect of a knee joint during a knee joint replacement procedure.

F. Tibial Preparation System with Landmark Acquisition Assembly and Extramedullary Alignment Guide FIGS. 3*a* and 3*b* show a tibial preparation system 310 (shown as assemblies 310*a* and 310*b*) for use in a joint replacement procedure, such as for example a knee replacement procedure. The tibial preparation system 310 can comprise the surgical orientation device 12 described above, the coupling device 14 described above, a landmark acquisition assembly 312, and an extramedullary alignment guide 314. The tibial preparation system 10 can be different from the systems 10 and 210, for example in that the system 310 can utilize both a structural alignment guide and surgical orientation device alongside a lateral side of the tibia (e.g. held alongside the tibia) to locate a plane containing the mechanical axis, and a second structural alignment guide (with surgical orientation device) attached along the anterior side of the tibia.

1. Orthopedic Fixture for Acquiring Anatomical Planes or Axes

An orthopedic fixture can be provided which can be used to identify and acquire anatomical planes and/or axes. For example, FIG. 24 shows an embodiment of a landmark acquisition assembly 312. The landmark acquisition assembly 312 can comprise an orthopedic fixture which can be used to identify the location of an axial line or plane. The landmark acquisition assembly 312 can comprise a structure or structures for contacting an anatomical landmark or landmarks in order to obtain an alignment of an axis or plane extending through those anatomical landmarks.

For example, in a preferred arrangement, the landmark acquisition assembly 312 can comprise an elongate member, for example a primary rod 316, with a proximal end 317*a* and a distal end 317*b*. The landmark acquisition assembly 312 can further comprise a connecting element or elements 318, and secondary rod or rods 320. The secondary rod or rods 320 can comprise transverse members coupled with each of the proximal and distal ends 317*a*, 317*b* of the primary rod 316. While the embodiment shown in FIG. 24 includes a single primary rod 316, two connecting elements 318, and four secondary rods 320, other embodiments can include other numbers or configurations of primary rods, connecting elements, and/or secondary rods. In some embodiments, the connecting element 3218 can be made integral with the primary rod 316 or a secondary rod 320.

The landmark acquisition assembly 312 can be arranged, for example, such that each connecting element 318 connects the primary rod 316 to at least one secondary rod 320. The secondary rods 320 and primary rod 316 can be at right angles to one another, as illustrated in FIG. 11, or can be at angles other than right angles.

Figure 25A:
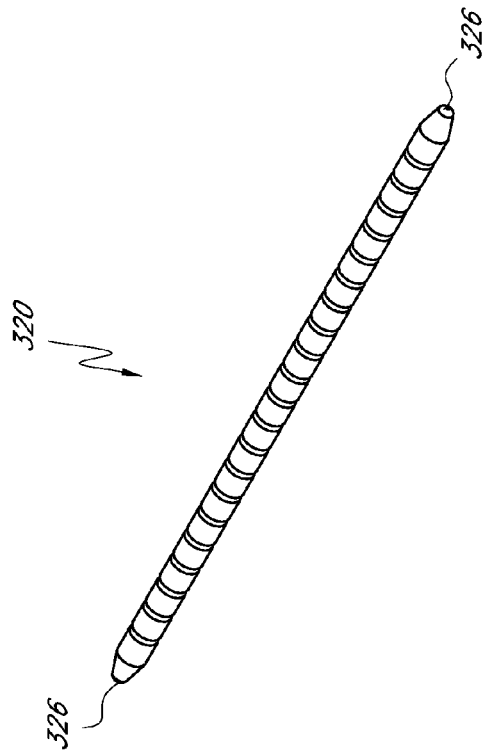
FIGS. 25A-B are perspective views of a primary and secondary rod of the landmark acquisition assembly of FIG. 24.

FIG. 25A shows a first portion 322 and a second portion 324 of a cross-section of the primary rod 316. The first portion 322 can be generally rounded, while the second portion 324 can be generally flat. The second portion 324 can facilitate connection with other components or devices in the system 310. For example, the second portion 324 can be configured to inhibit a connected device from rotating about or pivoting about the primary rod 316. The first and second portions 322, 324 can be arranged to permit only one orientation for the landmark acquisition assembly 312. Other configurations and shapes for a first portion 322 and second portion 324 besides those illustrated in FIG. 25 are also possible.

Figure 25B:
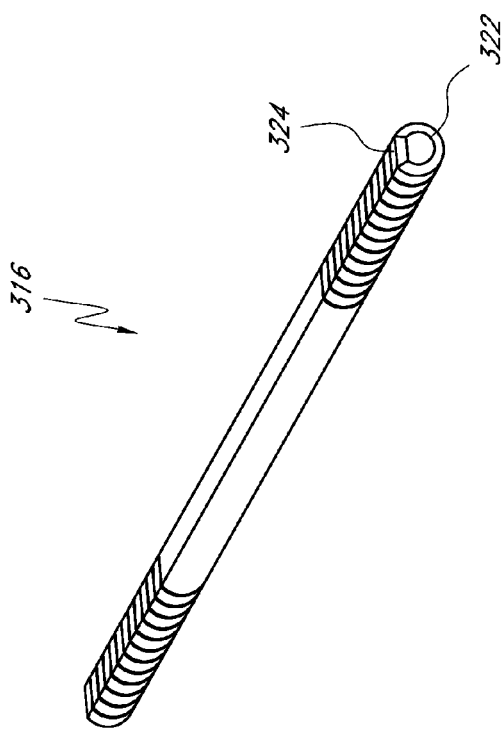

FIG. 25B shows ends 326 of the secondary rod 320 which can be narrowed and/or or pointed. The ends 326 can be used to contact portions of the human body in order to locate and/or pinpoint landmarks on the body, such landmarks including but not limited to the proximal tibia near the ligamentous attachment of the collateral ligaments, and the malleolus protruding out of the ankle region. Other shapes and configurations for the ends 326 are also possible. The secondary rod 320 can further include ribs, protrusions, or other structures which can engage the connecting element 318 and permit the secondary rod or rods 320 to be adjusted within the connecting element 318.

Figure 26:
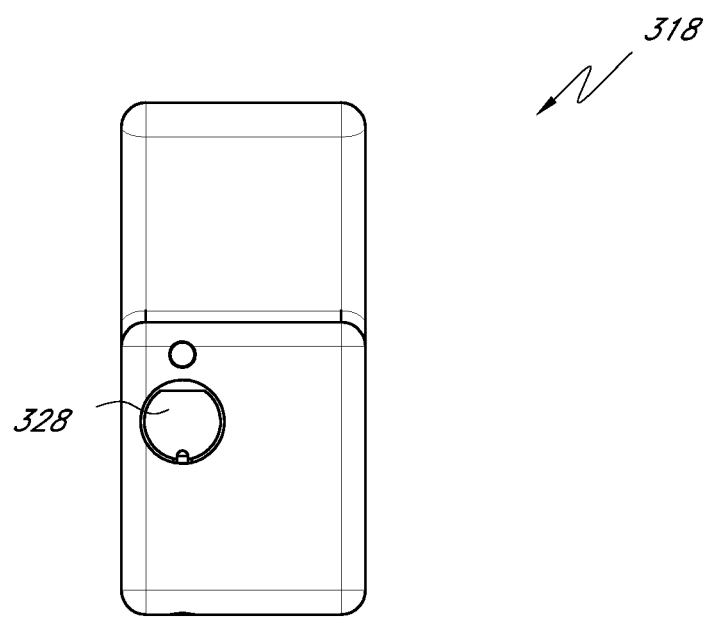
FIG. 26 is a front view of a connecting element of the landmark acquisition assembly of FIG. 24.

FIG. 26 shows an opening 328 in the connecting element 318 which can receive the primary rod 316 and facilitate connection of the primary rod 316 to another structure or structures. As illustrated in FIG. 26, the opening 328 can be shaped to receive the primary rod 316. The opening 328 can include a rounded portion and a flat portion both configured to engagingly receive the first portion 322 and second portion 324 of the primary rod 316.

The connecting element 318 can further include additional openings shaped to receive, for example, the secondary rods 320 shown in FIG. 25. The secondary rods 320 can be threaded, and openings of the connecting element 218 can include internal threads to receive the secondary rods 320. In a preferred arrangement, the opening 328, or other openings in the connecting element 318, can include notches, or grooves, which provide tactile feedback to a user when the primary rod 316 and/or secondary rod or rods 320 are sliding through the openings. The opening 328 or other openings in the connecting element 318 can extend entirely through the connecting element 318, thus allowing the primary rod 316 and/or secondary rod or rods 320 to be inserted entirely through the connecting element 318.

2. Orthopedic Fixture for Orienting a Surgical Orientation Device

Figure 27:
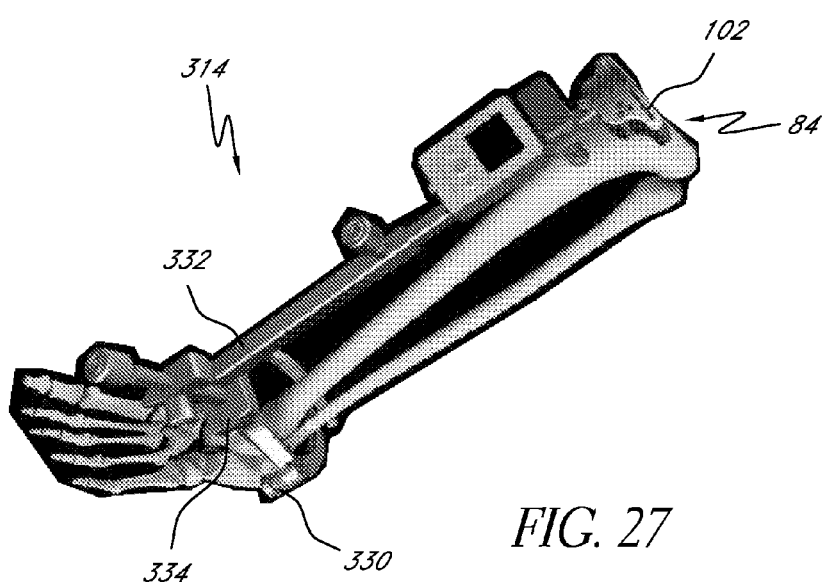
FIG. 27 is a perspective view of the second arrangement of the tibial preparation system of FIG. 3B, showing an extramedullary alignment guide according to one embodiment that can be used along the anterior side of the tibia.

An orthopedic fixture can be provided for orienting a surgical orientation device and/or cutting block. For example, FIG. 27 shows an extramedullary alignment guide 314. The extramedullary alignment guide 314 can comprise an orthopedic fixture which can be attached, at least in part, to an anatomical location, and can extend outside and/or along an appendage of the body. The extramedullary alignment guide can be used to aid in orienting a surgical orientation device, such as for example surgical orientation device 12, and for locating an axial line or plane.

As illustrated in FIG. 27, the extramedullary alignment guide 314 can comprise a distal mounting structure, such as for example a clamping portion 330, which can clamp onto a distal feature of a patient's leg or tibia, such as for example an ankle. The extramedullary alignment guide 314 can further comprise an elongate, extended rod 332 which can extend outside the body and generally parallel to the tibia. The clamping portion 330 can include a slide 334, which permits the extended rod 332 to slide and/or swing in front of the leg and tibia. The slide 334 can comprise an elongate recess or recesses along the clamping portion. The extended rod 332 can include a portion which fits within these recesses, and slides back and forth.

The extramedullary alignment guide can further comprise, or be attached to, a proximal mounting structure, such as for example a cutting block 84. The cutting block 84 can be identical to the cutting block 84 described above. For example, the cutting block 84 can comprise an opening 102 for insertion of a cutting tool (e.g. a cutting saw).

G. Acquiring Orientation Information Using a Landmark Acquisition Assembly and Extramedullary Alignment Guide After pre-operative planning for a joint replacement procedure, the tibial preparation system 310 described above can be used to identify the location and orientation of an axial line, as well as to orient a cutting block relative to the axial line.

For example, the leg to be operated on can be secured by placement in a leg holder, and the knee can be exposed using standard surgical procedure. During this time an extramedullary alignment guide, for example the extramedullary alignment guide 314, can be held in position adjacent the leg. A single spike on an end of the extramedullary alignment guide can be placed in a proximal medial tibial spine, such that an end of the extramedullary alignment guide is in position over the proximal medial tibial spine. Alternatively, a non-spiked rod can be used with an ankle clamp holding the guide in place.

Resection depth of the tibia can then be determined by, for example, using a stylus on the extramedullary alignment guide. For example, a depth of resection can be determined by aligning the stylus length-wise, parallel with the tibia, with the depth of resection being determined by the point of contact between the tip of the stylus and the lowest point of the medial condyle of the tibia.

Once the desired varus/valgus and posterior/anterior angles for resection have been determined pre-operatively for a knee replacement procedure, and the resection depth has been determined, the tibial preparation system (referring to system 310a) can be assembled as shown in FIG. 3a. For example, the surgical orientation device 12, coupling mechanism 14, and landmark acquisition assembly 312 can be coupled together, and the landmark acquisition assembly 312 can be positioned laterally alongside the tibia and outside of the leg.

Figure 28:
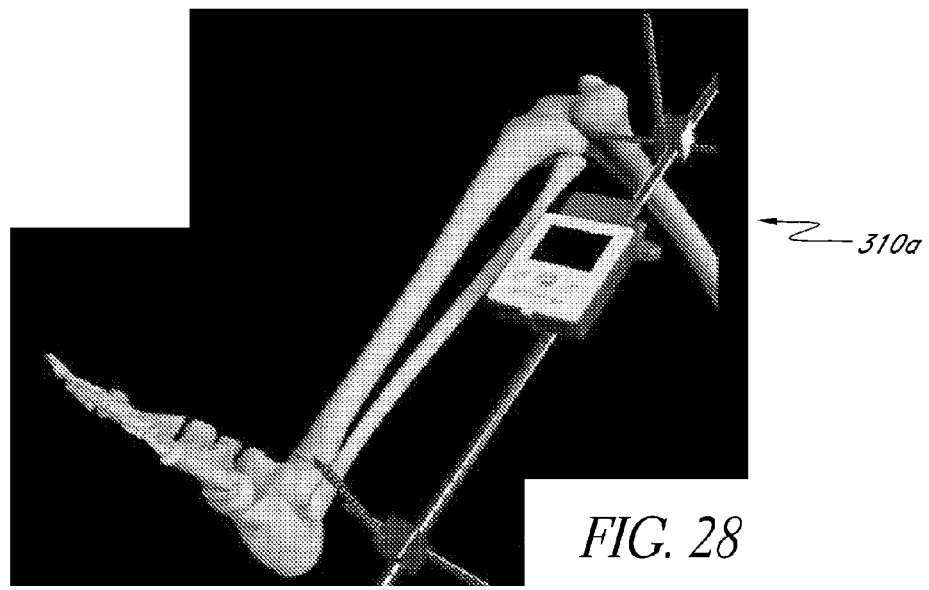
FIGS. 28 and 29 are perspective views of the first arrangement of the tibial preparation system of FIG. 3A during a knee joint replacement procedure.
Figure 29:
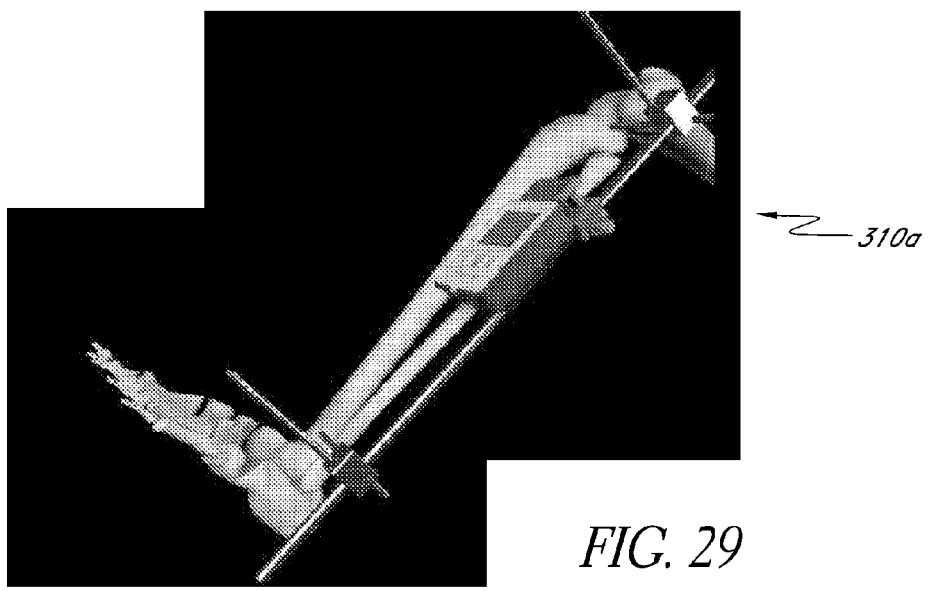

FIGS. 28 and 29 show the tibial preparation system 310a located laterally alongside the tibia. Specifically, FIGS. 28 and 29 show the tibial preparation system 10 being used to locate and reference an orientation of an axial line, in this case the mechanical axis extending through the lower (e.g. distal) leg.

In order to reference the orientation of the mechanical axis, the secondary rods 320 on the landmark acquisition assembly 312 can be adjusted such that their pointed ends 326 contact specified landmarks on the body. These landmarks can be pre-marked on the lower leg prior to a knee joint replacement procedure. Location of the landmarks can be acquired, for example, prior to a resection of the proximal tibia, with the tibia subluxed sufficiently to expose the tibial plateaus.

As shown in FIGS. 28 and 29, the tibia preparation system 310a can be used to acquire the mechanical axis in a coronal plane (i.e. acquire the orientation of a coronal plane containing the mechanical axis). For example, the secondary rods 220 can be adjusted and positioned such that one secondary rod 220 contacts the lateral collateral ligament of the proximal fibula head and another secondary rod 320 contacts the apex of the lateral malleolus. Once the secondary rods 320 have been adjusted, and are in contact with the aforementioned anatomical landmarks, the orientation of the mechanical axis can be obtained.

One of the user inputs 26 on the surgical orientation device 12 (e.g. a middle button below the display 24) can be pushed to record and/or register the orientation of the mechanical axis. The landmark acquisition assembly 312 can then be moved slightly back and forth until the surgical orientation device 12 indicates that the surgical orientation device 12 has acquired a plane containing the mechanical axis and verifies that the orientation has been recorded in the surgical orientation device 12. This indication can include, for example, a reading of zero on display 24, or some other signal. In a preferred arrangement, the display 24 can display a zero degrees reading and a flashing light (e.g. a green light), as shown in FIG. 29.

Once the surgical orientation device 12 has acquired an orientation of the mechanical axis, the surgical orientation device 12 and coupling device 14 can be removed from the landmark acquisition assembly 312, and the tibia preparation system can be re-assembled into system 310b such that the surgical orientation device 12 and coupling device 14 are coupled with the extramedullary alignment guide 314.

FIG. 30 shows the tibia preparation system 310b in an assembled state. In a preferred arrangement, the extramedullary alignment guide 214 can be aligned with the front of the leg. The clamping portion 330 can be used to clamp and/or secure a lower, or distal, portion of the extramedullary alignment guide 314 to the patient's ankle.

The extramedullary alignment guide 314 can be moved (e.g. rotated) in a first degree of rotation (e.g. roll) until the sensor or sensors 40 in the surgical orientation device 12 observe that the surgical orientation device 12 is in a plane parallel to the coronal plane containing the mechanical axis of the leg. Once the sensor or sensors 40 inside the surgical orientation device 12 observe that the surgical orientation device 12 is in this orientation, the surgical orientation device 12 can provide an indication to the user. For example, the surgical orientation device 12 can display zero degrees and a flashing light on the display 24. In a preferred arrangement, a pictorial representation of a bubble can be displayed that, for so long as the surgical orientation device 12 remains aligned with gravitational zero within an allowable range, stays within the confines of two vertical lines, each on one side of the bubble. The two vertical lines marking the confines of the "level" orientation range can correspond to a relative angle or tilt of plus and minus three degrees or plus and minus one degree, for example. In another embodiment, the graphical display of a bubble can be combined with a secondary indication to cue the user as to the state of alignment. For example, if the bubble moves beyond the lines, the background color of the screen behind the bubble can change from a first state (e.g., a first color, such as green) to a second state (e.g., a second color, such as amber) to indicate that the orientation is out of the acceptable range. Once the user has received this indication, the user can press a user input 26 (e.g. a middle button below display 24), confirming and/or registering the orientation of the surgical orientation device 12.

The extramedullary alignment guide 314 can then be moved (e.g. rotated) in a second degree of rotation (e.g. pitch) until the sensor or sensors 40 observe that the surgical orientation device 12 is in a plane parallel to the coronal plane containing the mechanical axis of the patient's leg. Once the sensor or sensors 40 inside the surgical orientation device 12 observe that the surgical orientation device 12 is in this orientation, the surgical orientation device 12 can again provide an indication to the user. For example, the surgical orientation device 12 can display zero degrees and a flashing green light on the display 24, and/or a bubble as described above. FIG. 31 shows such a flashing light on a display 24. Once the user has observed this light or other indication, the user can press a user input 26 (e.g. a middle button below display 24), confirming and/or registering the orientation of the surgical orientation device 12.

In some embodiments, the surgical orientation device can provide an indication when the surgical orientation device 12 is aligned in both degrees of freedom at the same time, rather than providing an indication each time separately. The user can then press the user input 26 once, rather than twice, to confirm registration of the orientation of the surgical orientation device 12.

In yet other embodiments, the surgical orientation device 12 can monitor and store the output of tilt meter sensors 40 in the surgical orientation device 12, such that when the tilt meter sensors 40 have been steady for a certain period, the surgical orientation device 12 can record the output to confirm and/or register the orientation of the surgical orientation device 12. In one technique, the surgical orientation device 12 can average the data recorded over a period of time (e.g. data recorded over the last second or several seconds prior to pressing a user input 26) and use the average as the acquired data for the coronal plane. This process can be used in other instances of the procedures described herein, for example when the surgeon or other medical personnel is directing the surgical orientation device 12 to acquire a plane or orientation of the surgical orientation device 12. This method can be advantageous in that it can reduce and/or eliminate inaccuracies caused by physical movement during a key-press (or other force imposed by the surgeon or other medical personnel onto the surgical orientation device 12, electrical noise due to the current flow during a key-press (or other user action), other vibrational movement, or electrical and physical (audio) noise. In certain embodiments, the surgical orientation device 12 can be configured to identify the data corresponding to the time a button is pressed and then use the most recent "good" data obtained before the button was pressed by the user (for example, before the fluctuations in the data occurred due to the button press).

Figure 32:
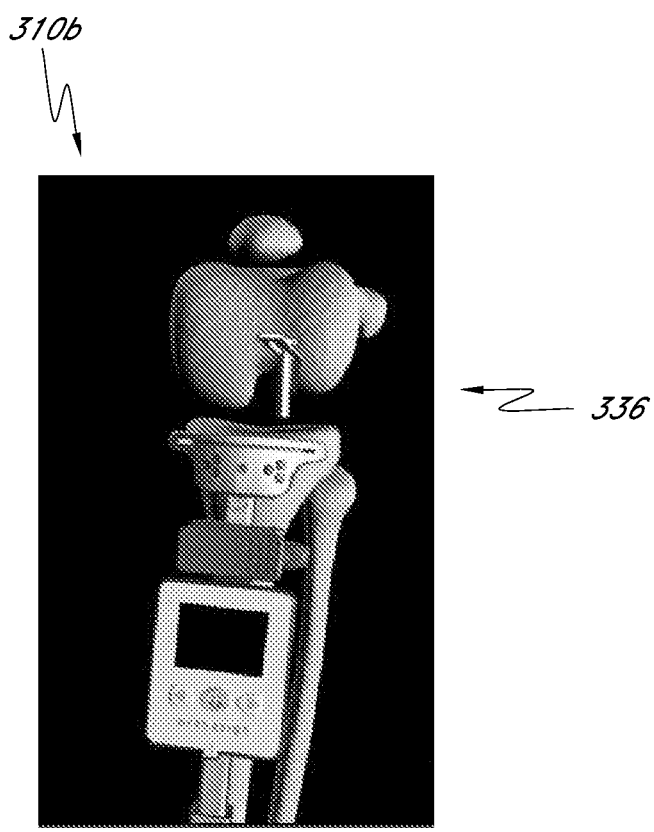

After registering the orientation of the mechanical axis as described above, the resection depth can be verified with a stylus. FIG. 32 shows a stylus 336. The stylus 336 can be attached to the extramedullary alignment guide 214. The stylus 336, or other surgical instrument, can be used to confirm and/or select a desired depth of resection for the tibial cut. This resection depth can be specified, for example, in an implant manufacturer's technique guide, and can help determine what size prosthetic component or components to use for the replacement knee joint.

Figure 33A:
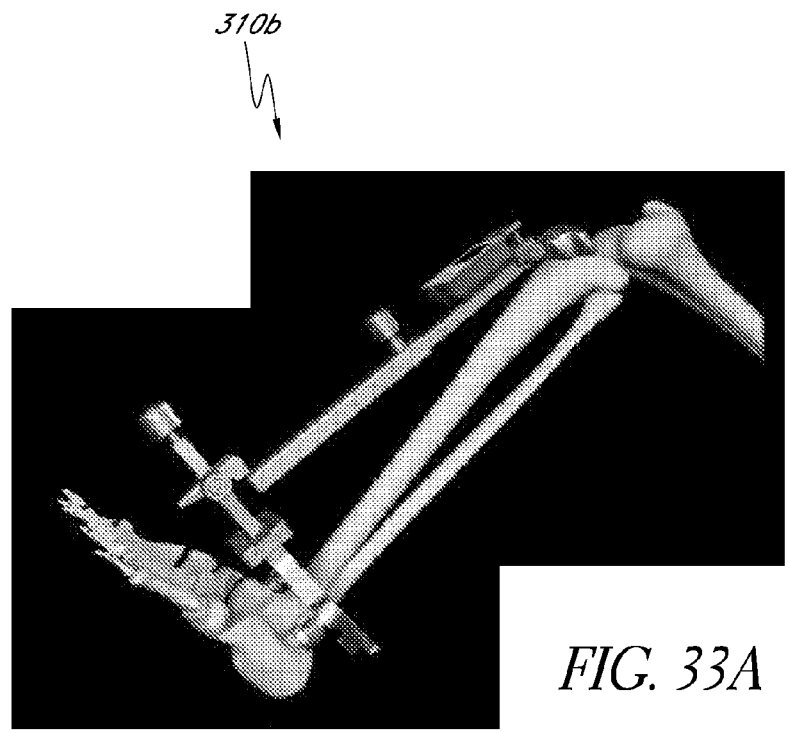
Figure 33B:
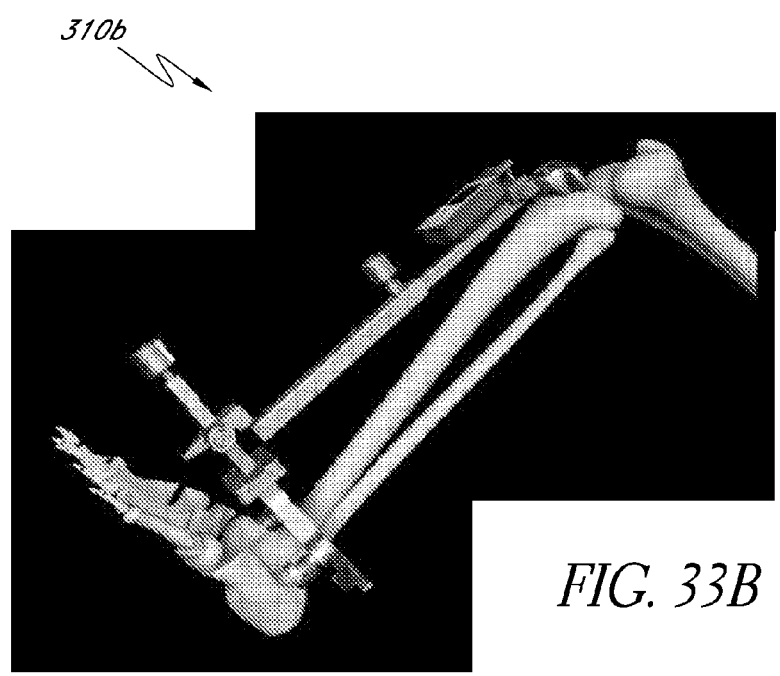

The user can then orient the cutting block 84 into the pre-operatively determined varus/valgus and posterior/anterior angles for resection. For example, the extended rod 332 of the extramedullary alignment guide 214 can be adjusted (e.g. swung) in the sagittal (i.e. flexion/extension) plane in order to move the cutting block 84 into the pre-operatively determined posterior/anterior angle. In one arrangement, a lower, or distal, portion of the extended rod 332 can be moved and/or adjusted further away from or closer to the clamping portion 330. FIGS. 33A and 33B illustrate movement of the extended rod 332 towards the clamping portion 330. By moving the distal, end of the extended rod 332 away from or closer to the clamping portion 330 of the extramedullary alignment guide 313, the posterior/anterior angle the cutting block 84 can be altered.

The extramedullary alignment guide 314 can additionally include markings, for example, which give an indication of the angle created by adjustment of the extended rod 332. In a preferred arrangement, the surgical orientation device 12 can also provide a read-out on its display 24 of the angle of orientation of the resection plane created by moving the extended rod 332.

Once the extended rod 332 is positioned as desired, a first mounting pin 333, or other anchoring device, can be inserted through the cutting block 84, for example as shown in FIGS. 34A and 34B. Once this first mounting pin 333 is inserted, the cutting block 84 and extending rod 332 can be restricted from movement in all but a varus/valgus plane along the front of the tibia.

The user can then locate the sagittal plane containing the mechanical axis through use of a laser guide or guides. For example, the user can press one of the user inputs 26 (e.g. the middle button beneath the display 24) on the surgical orientation device 12 to activate a laser system in the surgical orientation device 12. When the laser system is activated, the optical elements 32 on the top and bottom of the surgical orientation device 12 can emit red (or other color) laser beams out of the surgical orientation device 12. The laser beams can be in the form of lines, planes, cross-hairs, or other configurations.

Other locations for a laser system or systems can also be used. For example, the laser system can be attached to or integrated with the primary rod 316, secondary rods 320, and/or adjacent the surgical orientation device 12. In some embodiments, the laser system can be an entirely separate feature or device. In some embodiments, the laser system can be used for establishing the correct cutting angle during resection of the tibia and/or femur by providing beams which illuminate the epicondyles and/or a Whiteside's line to establish proper rotational orientation of a femoral implant.

FIGS. 35*a* and 35*b* illustrate how a laser system can be used to align the cutting block 84 with the sagittal plane which contains the mechanical axis. Once activated, the laser system in the surgical orientation device 12 can project a red laser light against the lower leg, with the laser light forming a line or lines along the exterior of the lower leg to provide visual cues as to alignment. For example, and as shown in FIGS. 35*a* and 35*b*, the laser light (dashed line in the figures) can emanate down the leg and extended rod 332 from an optical element 32 on the surgical orientation device 12, and can illuminate a landmark or landmarks, such as for example an anatomical landmark between the first and second toes on the patient's foot. Because only one pin or other anchoring device is inserted into the cutting block 84, the extended rod 332, surgical orientation device 12, and cutting block 84 can swing about the inserted first pin in a varus/valgus plane until the laser light is pointing to the desired landmark on the foot. FIGS. 35A and 35B illustrate an example of this movement.

Once the laser light has hit the desired landmark, the user can press a user input 26 on the surgical orientation device 12, and the surgical orientation device 12 can register the orientation of the sagittal plane. The surgical orientation device 12 can then provide a display of the varus/valgus angle as the varus/valgus angle changes relative to this recorded initial position. For example, the display 24 can indicate zero degrees when the cutting block is aligned with the sagittal plane, and can read other values when the cutting block is swung one way or the other relative to the initial position. This can allow the user to change the varus/valgus angle until the varus/valgus angle of the cutting block is at its pre-operatively determined value.

Figure 36A:
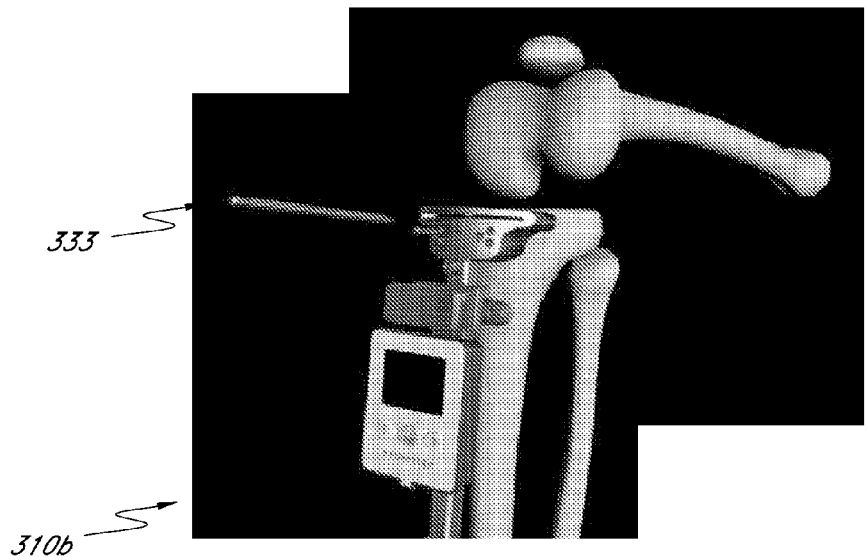
Figure 36B:
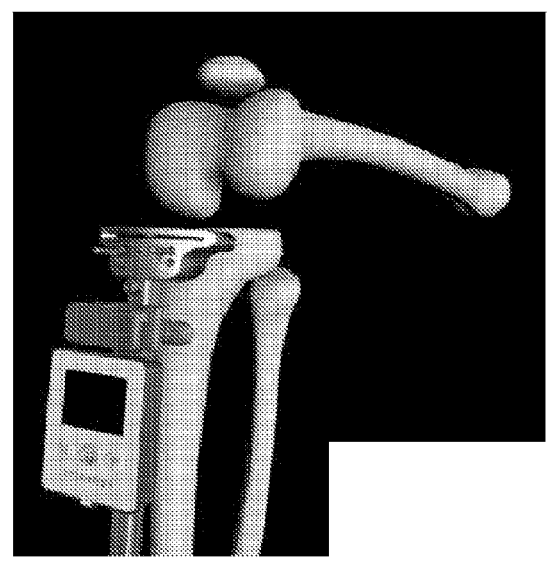

Once this desired value is obtained, the user can insert a second pin or pins, or other anchoring device or devices, through the cutting block 84 and into the tibia. FIGS. 36A and 36B illustrate a second mounting pin insertion. Once the second mounting pin 333 is inserted, the cutting block 84 can be fixed in place, or substantially fixed in place.

Figure 37:
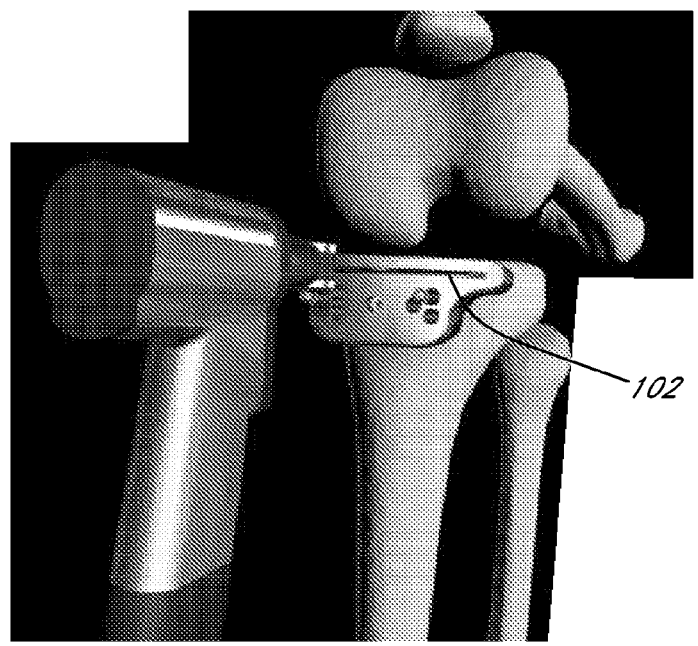
FIG. 37 is a perspective view of a cutting block and a cutting tool being used to resect a portion of the proximal tibia.

Once the cutting block is fixed, the rest of the extramedullary alignment guide 313, as well as the surgical orientation device 12 and coupling device 14, can be removed. FIG. 37 illustrates the cutting block 84 fixed to the tibia, with a cutting tool beginning to resect the tibia by moving a saw blade through the opening 102.

H. Tibial Preparation System with a Single Orthopedic Fixture

Figure 4A:
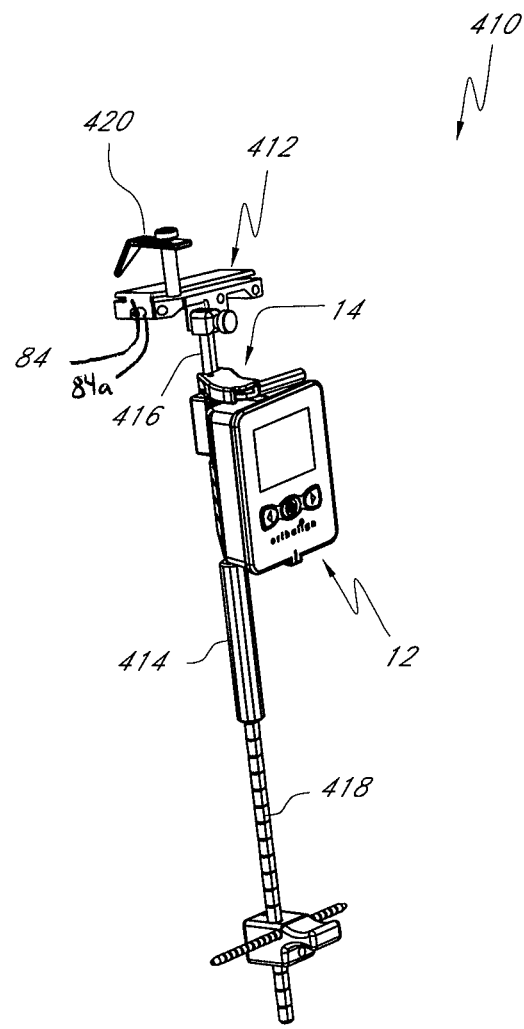
FIG. 4A is a perspective view of a first arrangement of another tibial preparation system according to one embodiment that can be used in connection with preparation of an aspect of a knee joint during a knee joint replacement procedure.
Figure 4B:
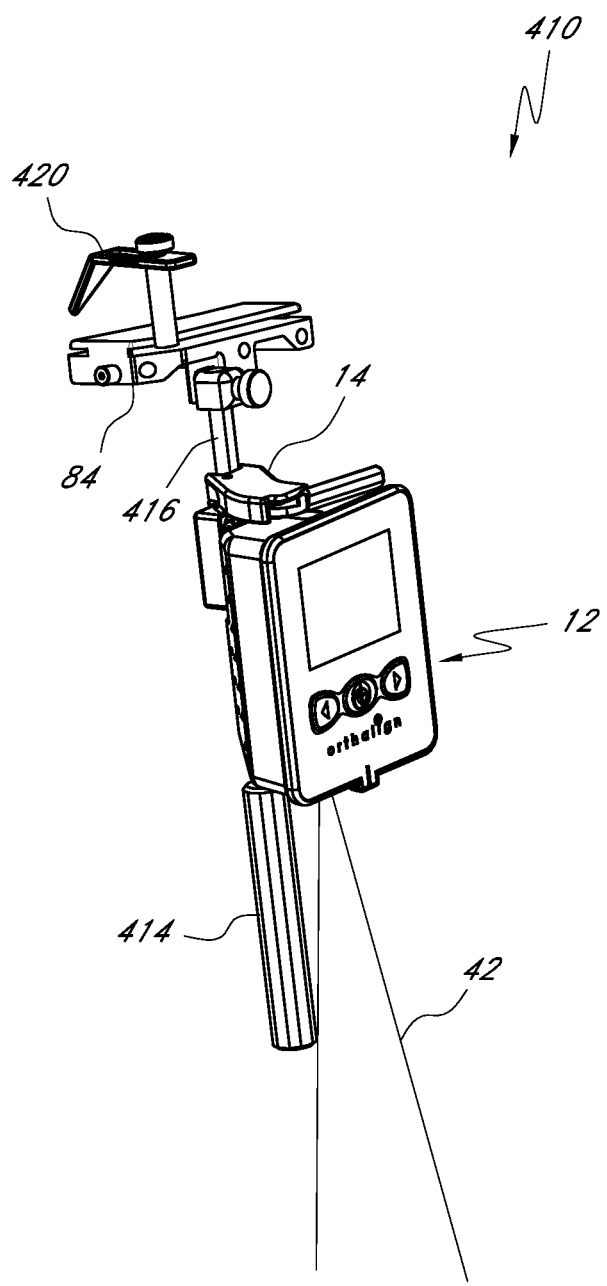
FIG. 4B is a perspective view of a second arrangement of the tibial preparation system of FIG. 4A.

A tibial preparation system can be provided which uses a single orthopedic fixture, instead of two orthopedic fixtures as described above. For example, FIGS. 4a and 4b show a tibial preparation system 410 for use in a joint replacement procedure, such as for example a knee replacement procedure. The tibial preparation system 410 can comprise the surgical orientation device 12 described above, the coupling device 14 described above, and a landmark acquisition assembly 412. The tibial preparation system 410 can be different from the systems 10, 210, and 310, for example in that the system 410 can utilize a single structural alignment device with a surgical orientation device, the alignment device being used along the lateral side of the tibia (e.g. held alongside the leg), as well as along the anterior side of the tibia.

The landmark acquisition assembly 412 can be similar to the landmark acquisition assembly 312 described above. For example, the landmark acquisition assembly 412 can comprise a primary rod, connecting element or elements, and secondary rod or rods.

The landmark acquisition assembly 412 can further include a handle 414. The handle 414 can attached to or integrally formed with a first portion 416 of the landmark acquisition assembly 414. For example, the handle 414 can be attached to or integrally formed with a primary rod, or other extending structure, of the first portion 416 of the landmark acquisition assembly 412.

The handle 414 can also be releasably coupled to a second portion 418 of the landmark acquisition assembly 412. For example, one end of the handle 414 can be screwed onto, and/or latched onto, an end of the second portion 418, such that the second portion 418 of the landmark acquisition assembly 412 can be removed from the first portion 416.

The surgical orientation device 12 can be coupled to the landmark acquisition assembly 412. For example, the surgical orientation device 12 can be coupled to the first portion 416 of the landmark acquisition assembly 412 with the coupling device 14. As shown in FIG. 4b, the surgical orientation device 12 can comprise a laser system or systems 42.

A cutting block 84 can also be attached to or integrally formed with the first portion 416, and can itself be attached to or integrally formed with a stylus 420 used for determining resection depth.

I. Acquiring Orientation Information Using a Single Orthopedic Fixture

After pre-operative planning for a joint replacement procedure, the tibial preparation system 410 described above can be used to identify the location and orientation of an axial line, as well as to orient a cutting block relative to the axial line.

For example, once the desired varus/valgus and posterior/anterior angles for resection have been determined pre-operatively for a knee replacement procedure, the tibial preparation system 410 can first be assembled as shown in FIG. 4a. The surgical orientation device 12, coupling mechanism 14, and landmark acquisition assembly 412 can be coupled together, and the landmark acquisition assembly 412 can be positioned laterally alongside the tibia and outside of the leg.

Similar to the method described above with respect to the landmark acquisition assembly 312, the secondary rods or structures on the landmark acquisition assembly 412 can be placed against predetermined anatomical landmarks alongside the leg, and the surgical orientation device 12 can register an orientation of the mechanical axis. Once the orientation of the mechanical axis has been registered, the landmark acquisition assembly can be positioned and/or aligned in front of the tibia, (i.e. anterior to the tibia)

Figure 38:
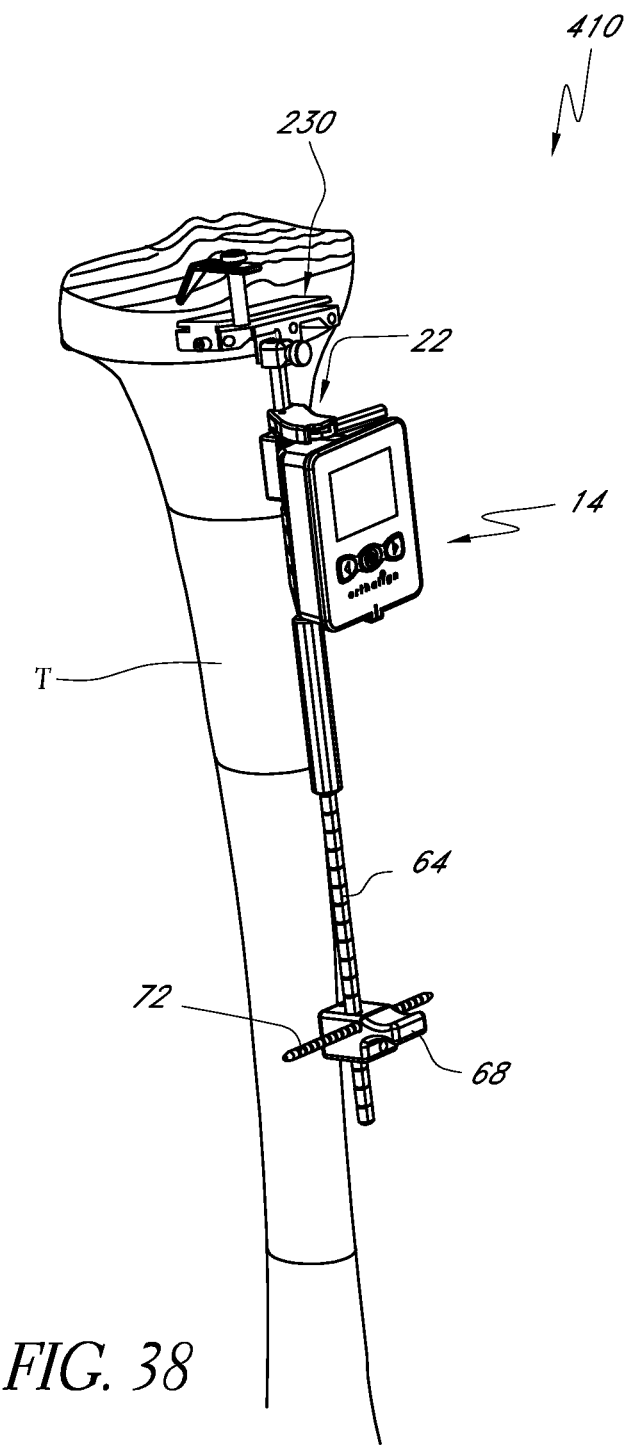
FIG. 38 is a perspective view of the tibial preparation system of FIG. 4B during a knee joint replacement procedure.
Figure 39:
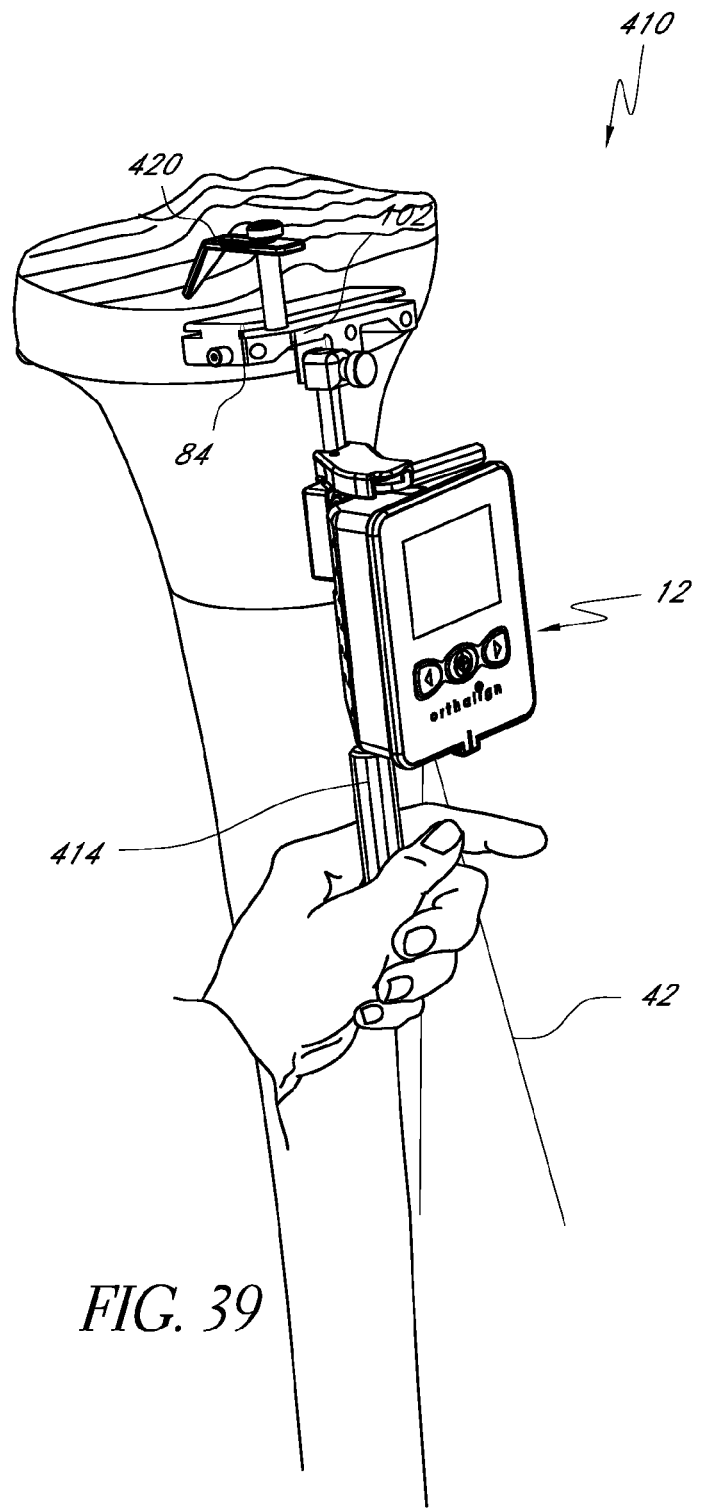
FIG. 39 is a perspective view of a the second arrangement of the tibial preparation system of FIG. 4B

FIGS. 38 and 39 show the landmark acquisition assembly 412 placed in front of the tibia T. The landmark acquisition assembly 412 can be moved and/or rotated in a first degree of rotation (e.g. roll) until the sensor or sensors 40 in the surgical orientation device 12 observe that the roll of the surgical orientation device 12 is aligned with gravitational zero. For example, one axis of a dual-axis accelerometer sensor 40 can be aligned with gravitational zero. Once the sensor or sensors 40 inside the surgical orientation device 12 observe that the surgical orientation device 12 is in this orientation, the surgical orientation device 12 can provide an indication to the user. For example, the surgical orientation device 12 can display zero degrees and a flashing green light on the display 24, or a bubble as described above. Once the user has received this indication, the user can press a user input 26 (e.g. a middle button below display 24), confirming and/or registering the orientation of the surgical orientation device 12.

The landmark acquisition assembly 412 can then be rotated and/or moved in a second degree of rotation (e.g. pitch) until the sensor or sensors 40 observe that the surgical orientation device 12 is in a plane parallel to the coronal plane containing the mechanical axis of the patient's leg. Once the sensor or sensors 40 inside the surgical orientation device 12 observe that the surgical orientation device 12 is in this orientation, the surgical orientation device 12 can again provide an indication to the user. For example, the surgical orientation device 12 can display zero degrees and a flashing green light on the display 24, or a bubble as described above. Once the user has observed this light or other indication, the user can press a user input 26 (e.g. a middle button below display 24), confirming and/or registering the orientation of the surgical orientation device 12.

As described above, in some embodiments the surgical orientation device can provide an indication when the surgical orientation device 12 is aligned in both degrees of freedom at the same time, rather than providing an indication each time separately. Similarly, in some embodiments the user can press the user input 26 once, rather than twice, to confirm registration of the orientation of the surgical orientation device 12.

Once the cutting block 84 is aligned with the mechanical axis, the opening 102 which comprises an elongated slot for receiving a cutting saw can extend generally perpendicular to the mechanical axis extending through the tibia. If pins were inserted through the cutting block 84 into the proximal end of the tibia to anchor the cutting block 84, and a cutting saw was inserted through this elongated slot 102, the cutting saw would resect the top of the tibia and leave a flat tibial plateau perpendicular to the mechanical axis.

However, as with the other methods described above, the cutting block 84 can be adjusted in order to orient the cutting block into the pre-operatively determined varus/valgus and/or posterior/anterior angles for resection. For example, the first portion 416 and second portion 418 of the landmark acquisition assembly 412 can be separated, and the second portion 418 can be placed to the side. The first portion can then be moved and/or rotated by hand in a varus/valgus direction and/or posterior/anterior direction.

FIG. 39 shows the landmark acquisition assembly 412 being maneuvered by hand. For example, the handle 414 can be moved towards or away from the distal end of the tibia in a sagittal plane to move the first portion 416 and cutting block 84. This movement can alter the angle of any pin placement in the cutting block 84, and consequently, alter the posterior/anterior angle of the cutting block 84.

Once the landmark acquisition assembly 412 and cutting block 84 are aligned as desired, a pin or other anchoring device can be inserted through a hole 102 of the cutting block 84 and into the tibia, for example as shown in FIG. 39. This first pin can anchor the cutting block in place, yet allow the cutting block 84 to swing in a varus-valgus direction about the first, fixed pin.

The handle 414 can then be used to swing the first portion 416 about the fixed pin, and to orient the cutting block in the varus/valgus plane. For example, a laser system, such as one described above, can be used while the cutting block 84 is pinned and swung by the handle 414. A laser beam or beams can emanate form the surgical orientation device 12 out of the optical element or elements 32. Similar to what is shown in FIGS. 35a and 35b, the laser beam can identify a landmark, such as the area between the first and second toes on the patient's foot, in order to acquire an orientation of the sagittal plane containing the mechanical axis.

Once the orientation of the sagittal plane containing the mechanical axis has been acquired and registered in the surgical orientation device 12, the handle 414 can be moved again to change the varus/valgus angle until the display 24 on the surgical orientation device 12 indicates that the varus/valgus angle of the cutting block is at its pre-operatively determined value.

Once the desired pre-operatively determined angles are obtained, a second pin or pins, or other anchoring device or devices, can be placed through the openings 102 in the cutting block 84, and the cutting block 84 can be anchored firmly, such that there is substantially no freedom of motion. The handle 414 and rest of first portion 416 can then be removed completely, leaving only the cutting block 84 securely anchored to the tibia. A cutting tool (e.g. cutting saw) can then be moved through the elongate opening 102 on the cutting block 84 to resect a portion or portions of the proximal tibia.

III. Femoral Cut/Knee Distraction Systems and Methods

As discussed above, knee replacement procedures commonly involve a resection of the tibia along the proximal tibia. This resection of the tibia typically leaves a tibial plateau or plateaus along the proximal tibia, which can provide a location for placement and/or attachment of a prosthetic knee joint.

In addition to a tibial resection, or alternatively to a tibial resection, a knee replacement procedure can further comprise a resection of a portion or portions of the distal femur. Resecting a portion or portions of the distal femur can provide a location for placement and/or attachment of a femoral knee joint prosthetic. As with the tibial resection, the orientation of a cutting block, and/or cutting plane or planes, can be pre-operatively determined in order to provide a desired fit and/or orientation for the femoral knee joint prosthetic. Properly orientating the cutting plane or planes along the distal femur can facilitate alignment of the femoral knee joint prosthetic with the tibial knee joint prosthetic. This alignment can create a set of knee joint prosthetics which function smoothly, continuously, and/or without substantial wear during their life of use.

Along with attaining and/or facilitating proper alignment between the femoral knee joint prosthetic and the tibial knee joint prosthetic, the user can additionally prepare the knee joint such that the ligaments and/or soft tissue surrounding the knee joint is substantially balanced after attachment of the knee joint prosthetics. A balanced joint refers generally to a joint in which one side of the knee is not substantially straining, pulling, and/or constraining the other side of the knee. For example, in an unbalanced knee joint, the ligaments and soft tissue on the lateral side of the knee may be experiencing tension at a substantially higher degree as compared to the ligaments and soft tissue on the medial side of the knee. During a knee joint replacement procedure, it can be advantageous to balance the tension on either side of the knee joint, so as to prevent undesired strain or stress within the knee joint. This balancing can be achieved, for example, by use of a knee distraction device or instrument which distracts the distal femur from the proximal tibia in a manner that achieves substantial balancing of the knee joint prior to attachment of the knee joint prosthetics.

Systems and methods of preparing a femoral cut, and/or distracting the knee are described further herein. While the systems and methods are described in the context of a knee joint replacement procedure, the systems and/or their components and methods can similarly be used in other types of medical procedures, including but not limited to shoulder and hip replacement procedures.

A. Femoral Preparation System with a Moveable Orthopedic Fixture

Figure 5:
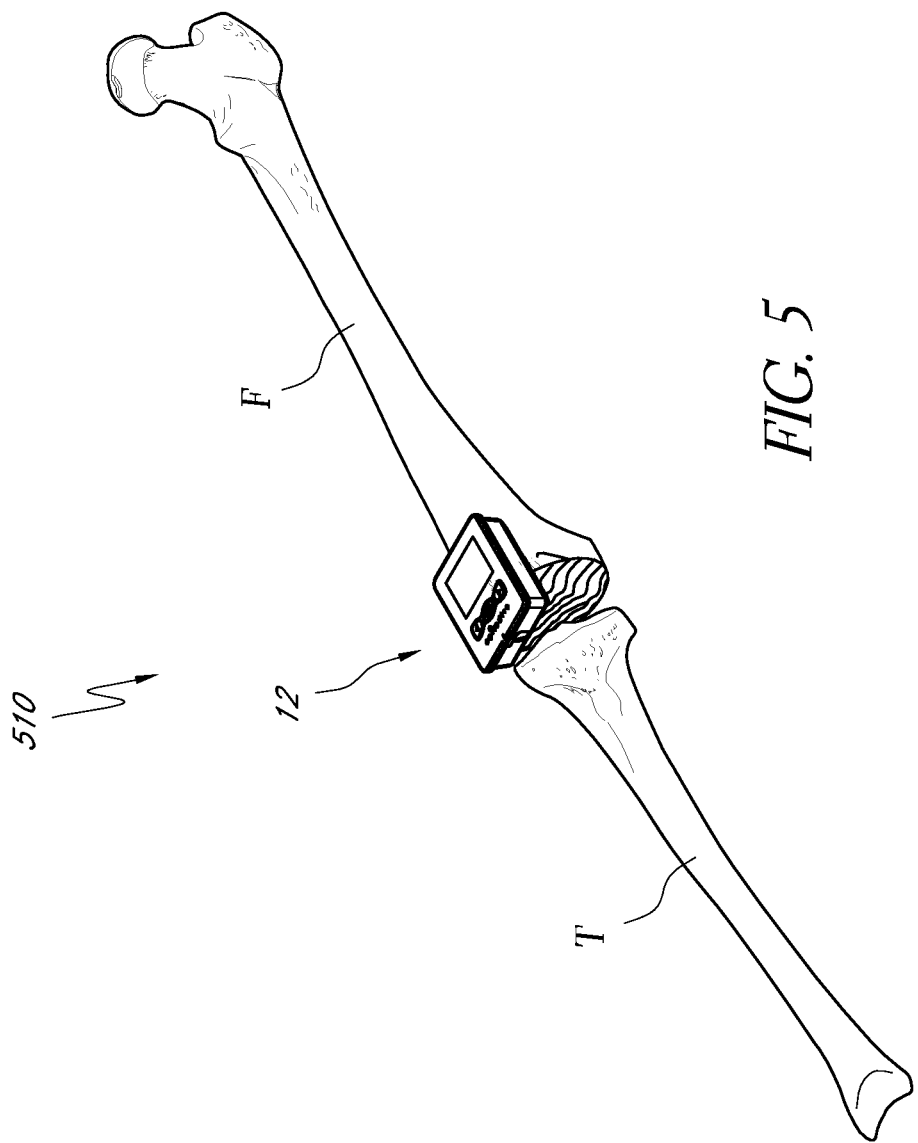
FIG. 5 is a perspective view of femoral preparation system according to one embodiment that can be used in connection with preparation of an aspect of a knee joint during a knee joint replacement procedure.

FIG. 5 shows a femoral preparation system 510 for use in a joint replacement procedure, such as a knee joint replacement procedure. The femoral preparation system 510 can be used to resect a portion of a femur, and can comprise the surgical orientation device 12 described above, the coupling device 14 described above, and an orthopedic fixture, such as a universal jig 512.

Figure 40:
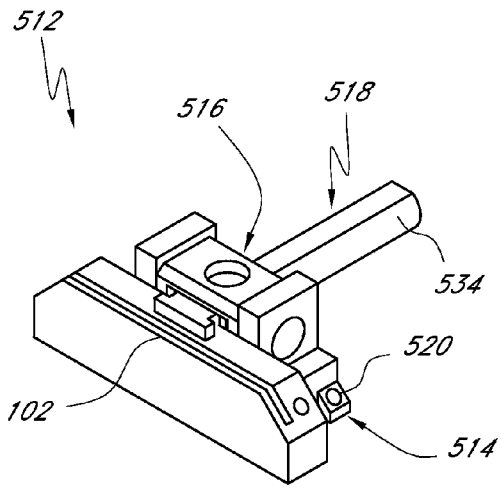
FIG. 40 is a perspective view of an orthopedic fixture according to one embodiment which can be used in the femoral preparation system of FIG. 5.
Figure 41:
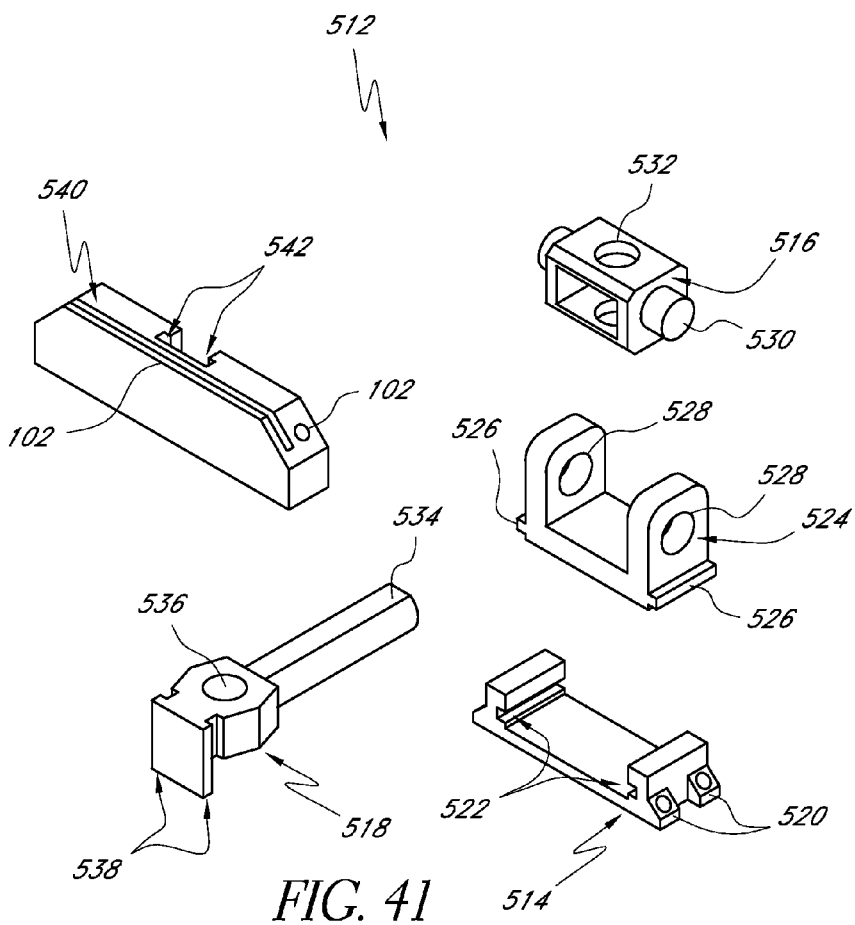
FIG. 41 is an exploded view of the orthopedic fixture of FIG. 40.

1. Orthopedic Fixture for Orienting a Surgical Orientation Device in Multiple Degrees of Freedom An orthopedic fixture can be provided which can have a moveable portion or portions which are used to orient a surgical orientation device. The surgical orientation device can be oriented in multiple degrees of freedom. For example, FIGS. 40 and 41 illustrate the universal jig 512. The universal jig 512 can be similar to the universal jigs described above. For example, the universal jig 512 can comprise a base portion 514, a posterior/anterior adjustment block 516, and a varus/valgus adjustment block 518.

The universal jig 512 can facilitate movement of a cutting block in at least two degrees of freedom. For example, the universal jig 512 can be configured to enable the surgeon to move a cutting block in a direction that changes the angle of the cut on the femur such that the cutting angle slopes either from the posterior to the anterior side of the knee or from the anterior to the posterior side (flexion-extension), providing one degree of freedom. The cutting block 512 can additionally or alternatively be configured so that a cutting block can be moved such that the cutting angle slopes in a varus-valgus manner, thereby providing a second degree of freedom.

In some embodiments, it can be desirable to provide multiple degrees of freedom in a translation direction. For example, the universal jig 512 can be configured to enable a cutting block to be moved in a proximal (toward the hip joint) or distal (toward the foot) direction, providing a first degree of freedom in translation. The universal jig 512 can further be configured such that a cutting block can be moved posteriorly toward the surface of the knee joint or anteriorly away from the surface of the knee joint to create more space between the block and the joint. In one technique it can be desirable to have the ability to move a cutting block posteriorly into contact with the anterior surface of the femur.

a. Base Member for Providing an Anchored or Fixed Initial Position of an Orthopedic Fixture, and Slide Member for Allowing Translational Movement A base member can be provided which can anchor or fix an initial position of an orthopedic fixture. A slide member can also be provided for allowing translation movement of a portion or portions of the orthopedic fixture. For example, and with continued reference to FIGS. 40 and 41, the base member 514 can be attached to a distal portion of the femur. For example, a pin, screw, or other anchoring device can be inserted through a hole or holes 520 located along the base member 514. The holes 520 can take any suitable configuration and orientation. For example, the holes 520 can be angled at 45° with respect to the posterior surface of the base member 514. Once the anchoring devices are inserted through the base member 514 and into the distal femur, the base member 514 can be held stable relative to the femur, while other portions of the universal jig 512 can move relative to the base member 514.

The base member 514 can comprise a slot or slots 522 extending along a portion or portions of the base member 514. The slots 522 can be configured to receive corresponding, or mating, flanges formed on a slide member 524. For example, the slots 522 can be configured to receive flanges 526 along slide member 524, as shown in FIG. 41. The slots 522 and flanges 526 can be configured such that slide member 524 can slide and/or translate both distally and proximally relative to the base member 514 and femur.

The slide member 524 can further comprise receiving holes 528. The receiving holes 528 can be sized and/or shaped so as to receive a pivot pin on the posterior/anterior adjustment block 516.

b. Device for Adjusting a Posterior/Anterior Slope of a Cutting Block

A posterior/anterior adjustment device can be provided which can be used to adjust the orientation of a surgical orientation device and/or cutting block adjacent the femur. For example, the posterior/anterior adjustment block 516 can comprise a pivot pin 530. As described above, the pivot pin 530 can be received by the receiving holes 528 on the slide member 524. The pivot pin 530 can facilitate pivoting motion and/or rotation of the posterior/anterior adjustment block 516 relative to the slide member 524 and/or base member 514 in a posterior/anterior direction. In a preferred arrangement, the pivot pin 530 can facilitate pivoting of the posterior/anterior adjustment block 516 within a range of approximately twenty degrees (e.g. +− ten degrees on either side of a predetermined angle). Other ranges are also possible.

The posterior/anterior adjustment block 516 can further comprise a receiving hole or holes 532. The receiving holes 532 can be sized and/or shaped so as to receive a pivot pin. The pivot pin can extend through the receiving holes 532 as well as through a receiving hole or holes on the varus/valgus adjustment block 518.

c. Device for Adjusting a Varus/Valgus Slope of a Cutting Block

A varus/valgus adjustment device can be provided which can be used to adjust the orientation of a surgical orientation device and/or cutting block adjacent the femur. For example, the varus/valgus adjustment block 518 can comprise an elongate rod 534. The elongate rod 534 can extend distally from the base member 514 when the universal jig 512 is attached to the distal femur. In a preferred arrangement of the universal jig 512, the elongate rod 534 can be coupled to the coupling device 14, and the coupling device 14 can be couple to the surgical orientation device 12.

With continued reference to FIG. 41, the varus/valgus adjustment block 518 can further comprise a receiving hole 536. As described above, the receiving hole 536 can receive a pin which extends through the receiving holes 532. The pin extending through the receiving holes 532 and 536 can facilitate pivoting motion and/or rotation of the varus/valgus adjustment block 518 relative to the base member, 514 in a varus/valgus direction. In a preferred arrangement, the pivot pin 530 can facilitate pivoting of the posterior/anterior adjustment block 516 within a range of approximately twenty degrees (e.g. +− ten degrees on either side of a predetermined angle). Other ranges are also possible.

The varus/valgus adjustment block 518 can further comprise a flange or flanges 538. The flanges 538 can be configured to be received by corresponding, or mating, slots in a cutting block or other structure.

d. Cutting Block Which can be Oriented for Bone Resection

A cutting block, or other orthopedic fixture, can be provided for bone resection. The cutting block can be oriented with the aid of a surgical orientation device and an orthopedic fixture or fixtures. FIGS. 40 and 41 illustrate a cutting block 540. The cutting block 540 can be similar to the cutting block 84 described above. For example, the cutting block 540 can comprise at least one opening 102. One opening 102 can comprise, for example, an elongate slot configured to receive a cutting tool, such as for example a cutting saw.

The cutting block 540 can further comprise a slot or slots 542. The slots 542 can be configured to receive the flanges 538 on the varus/valgus adjustment block 518. The combination of the slots 542 and flanges 538 can facilitate movement (e.g. translational movement) of the cutting block relative to the varus/valgus adjustment block 518. For example, in a preferred arrangement the cutting block 540 can translate in a posterior/anterior direction (i.e. towards or away from the femur).

B. Acquiring Information using a Femoral Preparation System

Figure 42:
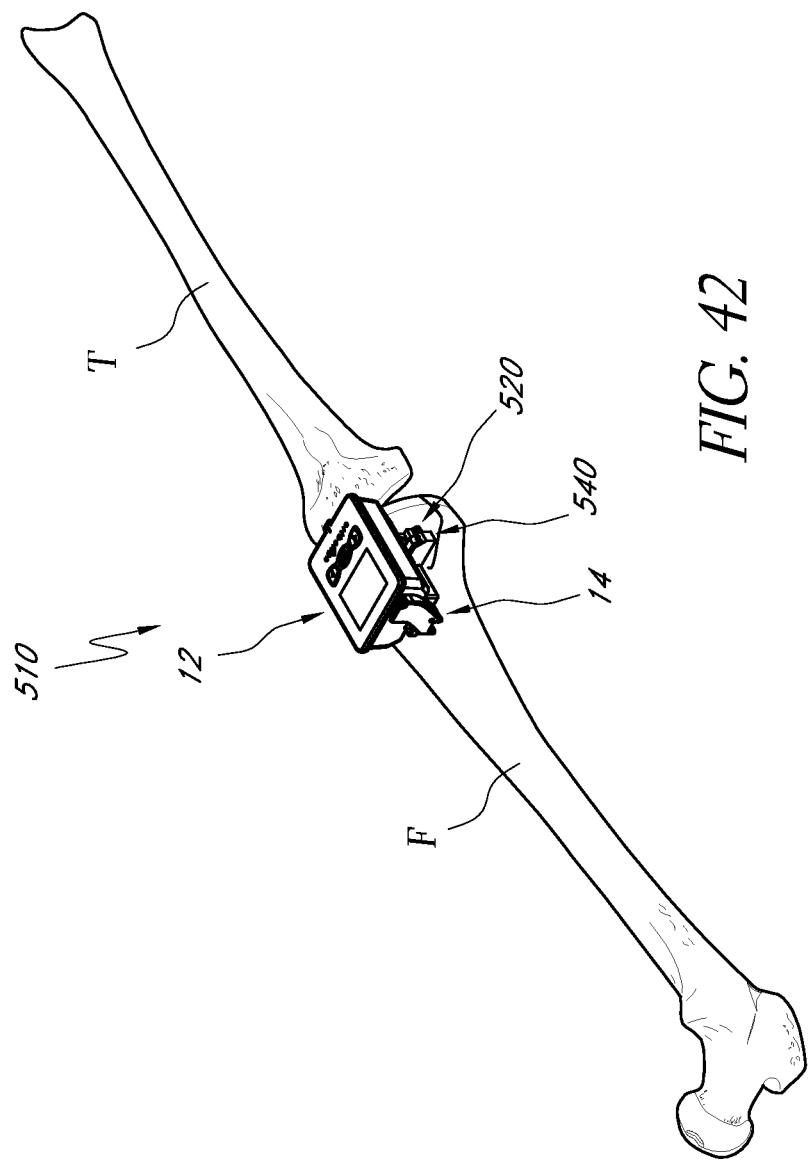
FIG. 42 is a perspective view of the femoral preparation system of FIG. 5 during a stage of a knee joint replacement procedure.
Figure 43:
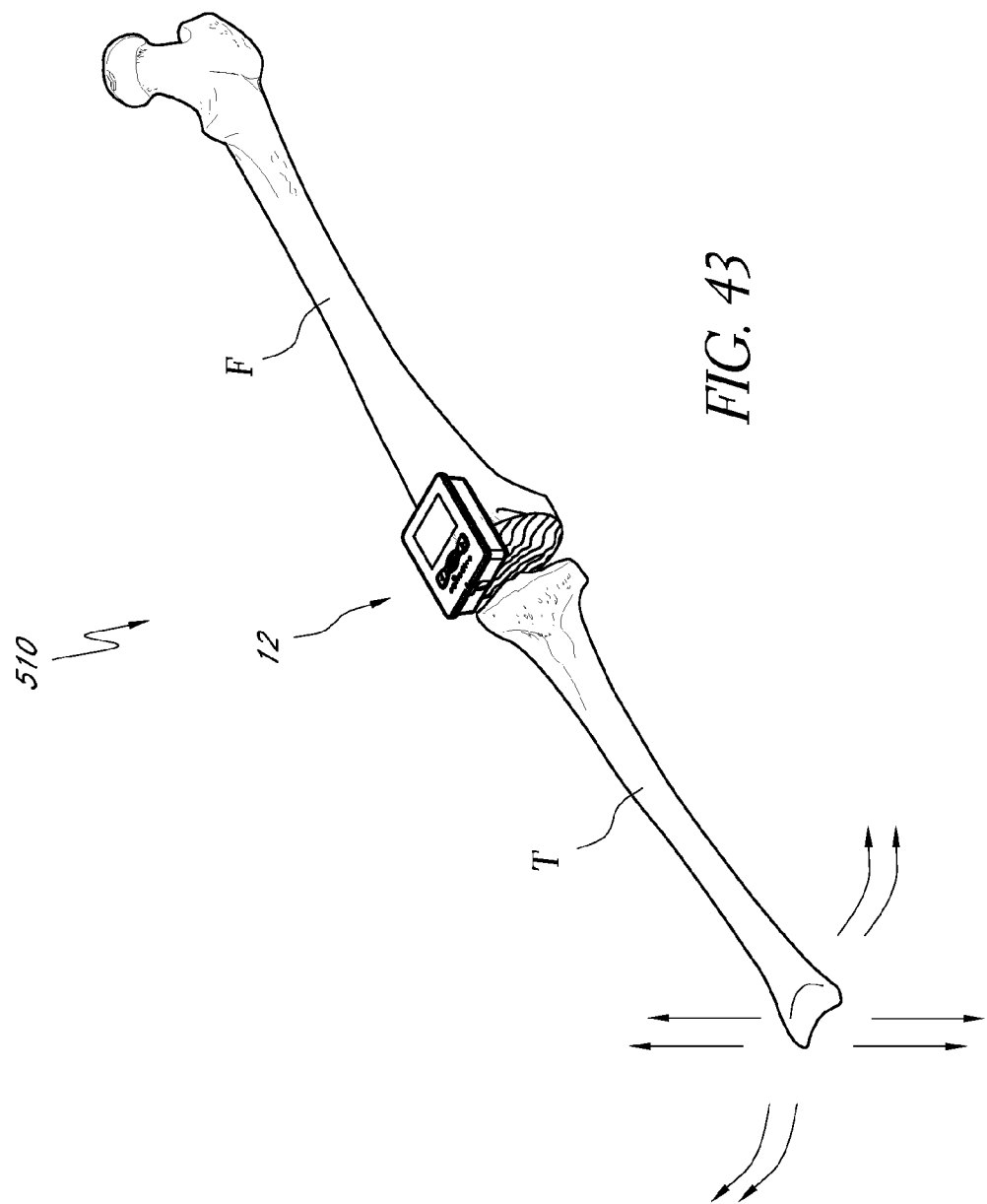
FIG. 43 is a perspective view of the femoral preparation system of FIG. 5 during another stage of a knee joint replacement procedure.

FIGS. 42 and 43 show a method of using the femoral preparation system 510. In a preferred arrangement, the base member 514 is first pinned to a distal aspect of the femur F, which has been exposed in any conventional surgical manner. The orientation device 12 can then be coupled with the elongate rod 534, for example by using the clamping device 14. Thereafter, the femoral preparation system 10, including the surgical orientation device 12, as well as the entire lower leg, can be moved, swung, and/or pivoted about a proximal head of the femur until the location and/or orientation of the mechanical axis of the leg is found.

For example, the center of rotation of the head of the femur, and/or the mechanical axis of the patient's leg, can be detected by moving and/or swinging the leg and attached surgical orientation device 12 on a horizontal plane (e.g. a plane along the operating table), starting from a known fixed position and orientation (referred to as the origin, which can be close to the surface of the horizontal plane) and obtaining inertial readings such as angular displacement and acceleration (referred to as IMU data). The arrows in FIG. 43 illustrate at least one example of how the direction or directions the leg can be moved.

The surgical orientation device 12, which can be coupled to the leg during such movement, can comprise at least one single- or multi-axis gyroscope sensor 40 and/or at least one single- or multi-axis accelerometer sensor 40. The accelerometer(s) can have axes angled with respect to an axis of the surgical orientation device 12. As the leg is swung, the sensors 42 can detect movement of the surgical orientation device 12, and collect the IMU data.

From this IMU data, the surgical orientation device 12 can calculate the location of the center of rotation of the femur, as well as the location of the mechanical axis running through the leg.

Once the surgical orientation device 12 has made the above-described calculation or calculations, the surgical orientation device 12 can be rotated and/or moved by the universal jig 512 to align the surgical orientation device 12 with the mechanical axis of the leg. When the surgical orientation device 12 is aligned with the mechanical axis of the leg, the surgical orientation device 12 can provide a signal, such as for example a flashing green light on its display 24.

The user can then use the universal jig 512 to move and/or change the position of the surgical orientation device 12 and cutting block 540, in order to achieve a pre-operatively determined resection angle or angles for resection of the femur. As with the tibial cut methods described above, the varus/valgus and posterior/anterior angles for resection can be adjusted by moving the varus/valgus adjustment block 518 and/or posterior/anterior adjustment block 516. Other adjustments, movements, translations, rotations, and/or changes in position of the cutting block 540 can also be made.

The surgical orientation device 12 can provide an indication of degrees of movement. For example, the surgical orientation device 12 can inform the user how many degrees (e.g. in half degree increments) the surgical orientation device and cutting block 540 are rotated past the mechanical axis in one or more planes. The surgical orientation device can display this information in its display 24, and/or provide audio indications to the user as well.

The cutting block 514 can then be brought into contact with the distal femur. The cutting block 540 can be immobilized, for example, by advancing pins through one or more openings 102. The user can then disconnect the surgical orientation device 12 from the universal jig 512, e.g. by releasing the clamping device 14. Additionally, or alternatively, the user can disconnect a portion or portions of the universal jig 512 from the cutting block 540, thereby leaving the cutting block 540 behind on the distal femur. Thereafter, the cutting block 540 can be used to resect the distal femur. For example, a cutting tool or tools can be moved through an elongate opening or openings 102, so as to prepare the distal femur for receiving a knee joint prosthetic.

C. Alternative Method of Using Femoral Preparation System

In other embodiments, the center of rotation and the mechanical axis can be detected by moving the leg about the junction of the femoral head and an acetabulum in several different planes, as opposed to one plane, and obtaining IMU inputs of the femur for various locations of the distal end of the femur approximating a portion of a spherical surface, with the center of the sphere being the femoral head center. For example, in one embodiment of the surgical orientation device 12 incorporating one or more multi-axis accelerometers and gyroscopes, IMU data for each movement of the femur can be numerically integrated over time to obtain a trajectory of position and velocity points (one point for each IMU input) without imposing any plane trajectory constraints on movements of the femur. The location of the sphere center (e.g., the femoral head center) can be calculated using, for example, a non-linear least-squares fit algorithm. Examples of three possible leg movement trajectories for calculating IMU data are: (i) a horizontal swing from the leg's position of origin to the surgeon's right and then back again; (ii) a horizontal swing from the origin to the surgeon's left and then back again; and (iii) a vertical swing upward and then back again. During each swing trajectory the IMU data can be stored for future processing.

Accuracy in determining the femoral head center can be improved if both positive and negative time integrations are performed for each movement of the femur from an origin at t=T0 to a given position at t=T1 and then back again to the origin at t=T2. The negative integrations (which correspond to integration from T2 to T0 in one technique) can be used to reduce the integration errors which may arise, for example, because of imperfect calibration or drift. For example, following each inertial measurement for a given location of the distal femur, the leg can be returned to its origin, with input provided to the surgical orientation device 12 that the surgical orientation device 12 has been returned to the origin. In one embodiment, the surgical orientation device 12 can be configured to assume or recognize that it has been returned to the origin. The surgical orientation device 12 can include a microcontroller in its electronic control unit 1102, for example, that can be configured to perform forward and backward integration over the maneuver and compare the results. This can be done as a way to calibrate the sensors 40.

When taking inertial readings, the surgical orientation device 12 can assume that roll motion of the femur (with respect to a femur line) is zero. In one method, the user can restrict the femur roll motion as much as possible and endeavor to move the femur in pitch and yaw motions (with respect to the femur line) when taking readings.

In one embodiment, the surgical orientation device 12 can be placed at the origin with no motion for a pre-determined time period to signal positioning at the origin, e.g., at least one second in between swing trajectories. This can facilitate the surgical orientation device's recognition of the start and end of a swing trajectory. In such an embodiment, a numerical value for magnitude of the acceleration of gravity or the location of the device in an Earth Centered Rotating (ECR) coordinate system can be an input to the processing inside the electronic control unit 1102.

In one embodiment of the device, there can be a parameterized function mapping of the IMU readings to the assumed or estimated acceleration and angular orientation in a frame attached to the device. This set of trajectory points (i.e. free trajectory points) along with the set IMU readings can be referred to as spherical independent values. There can be four individual dynamic sets of independent values, which are: position, velocity, IMU gyro values, and IMU accelerometer values. During the processing, a corresponding set of spherical dependent values can be generated, assuming the motion of the surgical orientation device 12 is constrained to the surface of the sphere and there is no roll motion about the line connecting the center of the sphere and the surgical orientation device 12. This set of values can be a function of the center of the sphere (the value for the radius of the sphere can be known since the origin is assumed to lie on the surface of the sphere) and, if needed, a set of IMU calibration parameters. The assumption can be made that at each IMU cycle time the surgical orientation device 12 is at a point of intersection of the sphere and the line connecting the corresponding independent position point and the center of the sphere.

The algorithm employed by the surgical orientation device 12 to determine the femoral head center can utilize a mathematical principle that determines the values for the unknown parameters (femoral head center and IMU calibration parameters) that minimize a cost function consisting of the sum of the squares of the difference between the spherical independent values and the spherical dependent values. The spherical independent IMU values can be provided by the sensor or sensors 40, and the spherical dependent IMU values can be calculated.

The following are two Cartesian coordinate frames that may be used to describe an algorithm:

1. The inertial Trajectory frame or T-frame. The coordinate frame for integrating the IMU input values. The origin is at the center of device at the start and end of each trajectory and the unit vectors are
   Z-axes ($Z_T$) points upward
   X-axes ($X_T$) points in patients foot to head in the horizontal plane
   Y-axes ($Y_T$) points to the surgeons left in the horizontal plane ($Y_T = Z_T \times X_T$).
2. The moving and rotating Device frame or D-frame. The IMU system can be attached to this frame and its origin can be located at the center of the IMU device. At the start/end of each frame it should be aligned with the T-frame.
   X-axes ($X_D$)=($X_T$)
   Y-axes ($Y_D$)=($Y_T$)
   Z-axes ($Z_D$)=($Z_T$)

The following symbols can be used to describe the processing that generates the spherical independent trajectory points for the nth swing trajectory according to one technique that can be incorporated into an embodiment of an orientation device described herein.

$\Delta$—IMU cycle time interval
$t_n^0$—Starting time of the trajectory
$t_n^I$—Ending time of the Ith IMU cycle ($I*\Delta$).
$N_n^I$—Total number of trajectory IMU time intervals.
$t_n^E$—Trajectory ending time ($N_n^I * \Delta$)
$w_n(t)$—IMU angular velocity input value for time t
$w_n^I$—IMU angular velocity input value for cycle I ($w_n(t)=w_n^I$ for $(I-1)*\Delta < t \leq I*\Delta$)
$a_n(t)$—IMU acceleration input value for the nth swing at time t.
$a_n^I$—IMU angular velocity input value for cycle I ($a_n(t)=a_n^I$ for $(I-1)*\Delta < t \leq I*\Delta$)
$W_D(x_w, w(t))$—The function that maps the IMU angular velocity value to the assumed/estimated angular velocity in the D-frame.
$x_w$—Gyro calibration parameters that can be estimated such as biases and scale factors.
$N_w$—Number of Gyro calibration parameters (can be zero)
$\Phi_D^T(t)$: Direction Cosine matrix—maps a vector in the D-frame to a vector in the T-fame. It can be calculated using both forward and backward time integration $$^+\Phi_D^T(t) = I_3 + \int_{t^0}^{t} (^+\Phi_D^T(t) \cdot W_D(x_w, w(s)) \times {}^+\Phi_D^T(s)) ds$$

$$^-\Phi_D^T(t) = I_3 + \int_{t^E}^{t} (^-\Phi_D^T(t) \cdot W_D(x_w, w(s)) \times {}^-\Phi_D^T(t)(s)) ds$$

$$I_3 = \begin{pmatrix} 1 & 0 & 0 \\ 0 & 1 & 0 \\ 0 & 0 & 1 \end{pmatrix}$$

$A_D(x_A, a(t))$—The function that maps the IMU accelerometer value to the assumed/estimated acceleration in the D-frame.

$x_A$: Accelerometer calibration parameters that may need to be estimated such as biases and scale factors.
$N_A$—Number of Accelerometer calibration parameters (can be zero).
$^+R_n^I(x_A, x_W)$—Ith positive trajectory position point
$^-R_n^I(x_A, x_W)$—Ith negative trajectory position point
$^+V_n^I(x_A, x_W)$—Ith positive trajectory velocity point
$^-V_n^I(x_A, x_W)$—Ith negative trajectory velocity point $$^+R_n^I(x_A,x_W) = \int_0^{t_n^I} \int_0^t A_T(x_w,x_A,w_n(s),a_n(s)) ds\, dt$$

$$^-R_n^I(x_A,x_W) = \int_{T_n^I}^{T_n^E} \int_{T_n^I}^t A_T(x_w,x_A,w(s),a(s)) ds\, dt$$

$$^+V_n^I(x_A,x_W) = \int_0^{t_n^I} A_T(x_w,x_A,w_n(s),a_n(s)) ds$$

$$^-V_n^I(x_A,x_W) = \int_{T_n^I}^{t_n^I} A_T(x_w,x_A,w_n(s),a_n(s)) ds$$

$$A_T(x_w,x_A,w_n(s),a_n(s)) = \Phi_D^T(x_w,s) \cdot A_D(x_A,a_n(s))$$

$R_n^I(x_A, x_W)$ Ith trajectory position point.

$$R_n^I(x_A,x_W) = \beta^+({}^+R_n^I(x_A,x_W)) + (1-\beta^+)*({}^-R_n^I(x_A,x_W))$$

$$\beta^+ = (t_n^E - t_n^I)/t_n^E$$

Error in double integration due to white is proportional to the time of integration.

$V_n^I(x_A, x_W)$—The Ith trajectory velocity point $$V_n^I(x_A,x_W) = \beta^{+*}({}^+V_n^I(x_A,x_W)) + (1-\beta^+)*({}^-V_n^I(x_A,x_W))$$

$$\beta^+ = ((t_n^E - t_n^I)/t_n^E)^{1/2}$$

Error in single integration due to white is proportional to the square-root of time of integration.

The following describes a processing for the spherical dependent trajectory parameters. Most of the calculation can be performed in the Inertial Trajectory Frame. This processing assumes the points are constrained to the surface of a sphere. The center of the sphere is denoted by $\vec{R}c$ or the three component vector ($x_c$, $y_c$, $z_c$). Since the origin is assumed to be on the sphere the radius of the sphere is $$Rc = (x_c^2 + y_c^2 + z_c^2)^{1/2}$$

The following symbol and expression are use to describe how the Ith spherical dependent trajectory parameter values can be calculated in terms of the (I−1)th values for the nth swing trajectory.

$^S R_n^I$—Ith position point $$^S R_n^I = \text{unit}(R_n^I) * Rc$$

$^S \theta_n^I$—Ith rotation vector $$^S \theta_n^I = \text{unit}({}^S R_n^{I-1} \times {}^S R_n^I) * \text{arc cos}(\text{unit}({}^S R_n^{I-1}) \cdot \text{unit}({}^S R_n^I))$$

$^S \Omega_n^I$—Ith angular velocity vector $$^S \Omega_n^I = {}^S \theta_n^I / \Delta$$

$^S V_n^I$—Ith velocity point $$^S V_n^I = {}^S \Omega_n^I \times {}^S R_n^I$$

$^S A_n^I$—Ith acceleration vector $$^S A_n^I = ({}^S V_n^I - {}^S V_n^{I-1})/\Delta$$

$^S \Phi_n^I$—Ith Spherical Trajectory direction cosine matrix; transforms a vector in the Device frame to a vector in the Trajectory frame.

$$^S\Phi_n^{I-1} = {}^S\theta_n^I \otimes {}^S\Phi_n^{I-1}; \quad {}^S\Phi_n^0 = \begin{pmatrix} 1 & 0 & 0 \\ 0 & 1 & 0 \\ 0 & 0 & 1 \end{pmatrix}$$

The operator "$\otimes$" produces the direction cosine matrix that results from rotating the direction cosine matrix to the right of the operator about the angle to the left of the operator.

$_D{}^S\Omega_n^I$—Ith angular velocity vector for the nth swing trajectory expressed in the device frame $$_D{}^S\Omega_n^I = \tfrac{1}{2} * ({}^S\Phi_n^{I-1} + {}^S\Phi_n^I)^T \cdot {}^S\Omega_n^I$$

$_D{}^SA_n^I$—Ith acceleration vector expressed in the device frame $$_D{}^SA_n^I = \tfrac{1}{2} * ({}^S\Phi_n^{I-1} + {}^S\Phi_n^I)^T \cdot {}^SA_n^I$$

$^Sw_n^I$: Ith calculated gyro value (the application of the inverse mapping of the gyro calibration function)

$$^sw_n^I = W_D^{-1}(x_w, {}_D{}^S\Omega_n^I)$$

$^Sa_n^I$ Ith calculated gyro value (the application of the inverse mapping of the accelerometer calibration function)

$$^Sa_n^I = A_D^{-1}(x_a, {}_D{}^SA_n^I)$$

The following contains a definition of the four trajectory parameter cost functions and the total cost function. The total cost function represents a weighted average of the four trajectory parameter cost functions.

$\gamma_R(x_c, y_c, z_c, x_A, x_W)$-Position Cost Function $$\gamma_n^R(x_c, y_c, z_c, x_A, x_W) = \left( \sum_{I=1}^{N_n^I} |{}^S R_n^I - R_n^I|^2 \right)$$

$$\gamma_R(x_c, y_c, z_c, x_A, x_W) = \sum_{n=1}^{N_T} \gamma_n^R(x_c, y_c, z_c, x_A, x_W)$$

$\gamma_V(x_c, y_c, z_c, x_A, x_W)$-Velocity Cost Function $$\gamma_n^V(x_c, y_c, z_c, x_A, x_W) = \left( \sum_{I=1}^{N_n^I} |{}^S V_n^I - V_n^I|^2 \right)$$

$$\gamma_V(x_c, y_c, z_c, x_A, x_W) = \sum_{n=1}^{N_T} \gamma_n^V(x_c, y_c, z_c, x_A, x_W)$$

$\gamma_G(x_c, y_c, z_c, x_A, x_W)$-Gyro Cost Function $$\gamma_n^G(x_c, y_c, z_c, x_A, x_W) = \left( \sum_{I=1}^{N_n^I} |{}^S w_n^I - w_n^I|^2 \right)$$

$$\gamma_G(x_c, y_c, z_c, x_A, x_W) = \sum_{n=1}^{N_T} \gamma_n^G(x_c, y_c, z_c, x_A, x_W)$$

$\gamma_A(x_c, y_c, z_c, x_A, x_W)$-Accelerometer Cost Function $$\gamma_n^A(x_c, y_c, z_c, x_A, x_W) = \left( \sum_{I=1}^{N_n^I} |{}^S a_n^I - a_n^I|^2 \right)$$

$$\gamma_A(x_c, y_c, z_c, x_A, x_W) = \sum_{n=1}^{N_T} \gamma_n^A(x_c, y_c, z_c, x_A, x_W)$$

$\gamma(x_c, y_c, z_c, x_A, x_W)$-Total Cost Function $$\gamma(x_c, y_c, z_c, x_A, x_W) =$$
$$\alpha_R * \gamma_R(x_c, y_c, z_c, x_A, x_W) + \alpha_V * \gamma_V(x_c, y_c, z_c, x_A, x_W) +$$
$$\alpha_G * \gamma_G(x_c, y_c, z_c, x_A, x_W) + \alpha_A * \gamma_A(x_c, y_c, z_c, x_A, x_W)$$

The mathematical goal of the algorithm can be to solve the following 3+Na+Nw equations for ($x_c$, $y_c$, $z_c$, $x_A$, $x_W$) that minimize the Total Cost Function.

$$\partial \gamma(x_c, y_c, z_c, x_A, x_W)/\partial x_c = 0$$

$$\partial \gamma(x_c, y_c, z_c, x_A, x_W)/\partial y_c = 0$$

$$\partial \gamma(x_c, y_c, z_c, x_A, x_W)/\partial z_c = 0$$

$\nabla x_A(\gamma(x_c, y_c, z_c, x_A, x_W)) = 0, \nabla x_A$ the gradient wrt accelerometer calibration parameters $\nabla x_W(\gamma(x_c, y_c, z_c, x_A, x_W)) = 0, \nabla x_W$ the gradient wrt gyro calibration parameters

Figure 6:
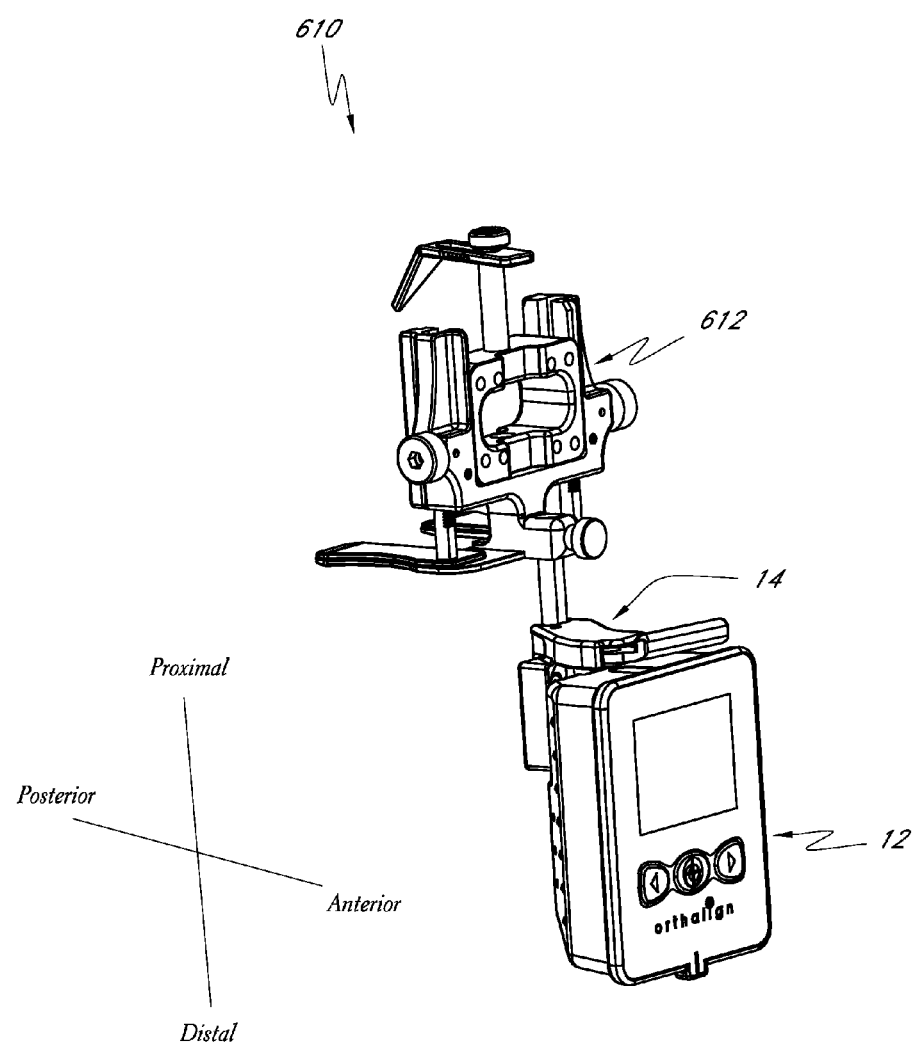
FIG. 6 is a perspective view of a femoral preparation and knee distraction system according to one embodiment that can be used in connection with preparation of an aspect of a knee joint during a knee joint replacement procedure.

D. Femoral Preparation System with Knee Distraction Device for Resecting the Femur and/or Distracting the Knee Joint A femoral preparation system can be provided which can both align a cutting block for resecting a bone, as well as distract a joint so as to balance the tissue surrounding the joint. For example, FIG. 6 shows a femoral preparation system 610 for use in a joint replacement procedure, such as for example a knee joint replacement procedure. The femoral preparation system 610 can comprise the surgical orientation device 12 described above, the coupling device 14 described above, and a distraction instrument, such as for example a knee distraction device 612. As described further herein, the femoral preparation system 610 can be used for both alignment and distraction.

Figure 44:
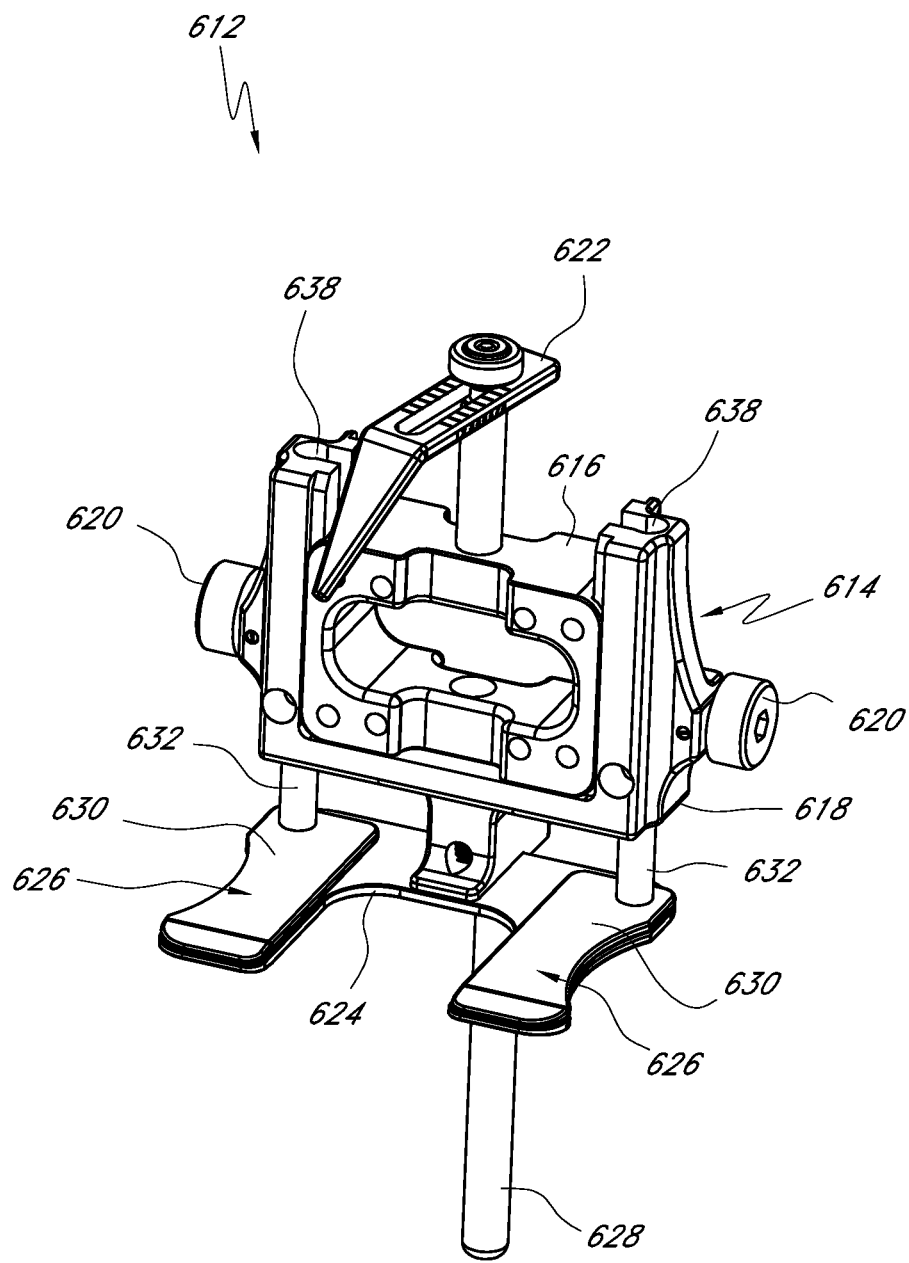
FIG. 44 is a perspective view of a distraction device according to one embodiment which can be used in the femoral preparation system of FIG. 6.

FIG. 44 shows a knee distraction device 612. The knee distraction device 612 can be configured to distract the knee joint during a knee replacement procedure and balance the soft tissue and/or ligaments within the knee joint. The knee distraction device 612 can additionally or alternatively be configured to facilitate attachment of a cutting block to the distal femur for resection of the distal femur.

With continued reference to FIG. 44, the knee distraction device 612 can comprise a distractor body, such as for example a body 614. The body 614 can comprise an inner body portion 616, an outer body portion 618, and at least one adjustment device 620. The knee distraction device 612 can further comprise a reference feature, such as for example a tibial baseplate 624, and at least one distraction element 626. The knee distraction device can further comprise guide portion 628. The body 614, tibial baseplate 624, and distraction element or elements 626 can form an anterior portion of the knee distraction device 612.

In some embodiments the distraction elements 626 can comprise femur contacting components. For example, the distraction elements 626 can include generally flat, thin, foot portions 630 which extend away from the body 614, and can be configured to engage the bottom of a bony landmark, such as for example a femoral condyle. The distraction elements 626 can further include posts 632 which can be movable relative to the tibial baseplate 624, and can extend into a portion or portions of the outer body portion 618.

The posts 632 can be controlled by the adjustment devices 620 on either side of the body 614. The adjustment device or devices 620 can comprise knobs, and the distraction elements 626 can resemble feet, with legs which extend from a lower, or distal, portion of the body 614.

The tibial baseplate 624 can comprise a planar member coupled to the distractor body, and can sit underneath the distraction elements 626. The tibial baseplate can be configured to be positioned on a tibial plateau. The tibial baseplate 624 can extend at an angle perpendicular to a front face of the body 614. The distraction elements 626 can be coupled with the distractor body, and can be configured to be moved relative to the tibial baseplate 624 to increase or decrease a gap therebetween. The distraction elements 626 can also extend at an angle perpendicular to the front face of the body 614, and can individually be moved away from the tibial baseplate 624 (e.g. in a proximal direction), or towards the tibial baseplate 624 (e.g. in distal direction), by turning the adjustment devices 620.

Figure 45:
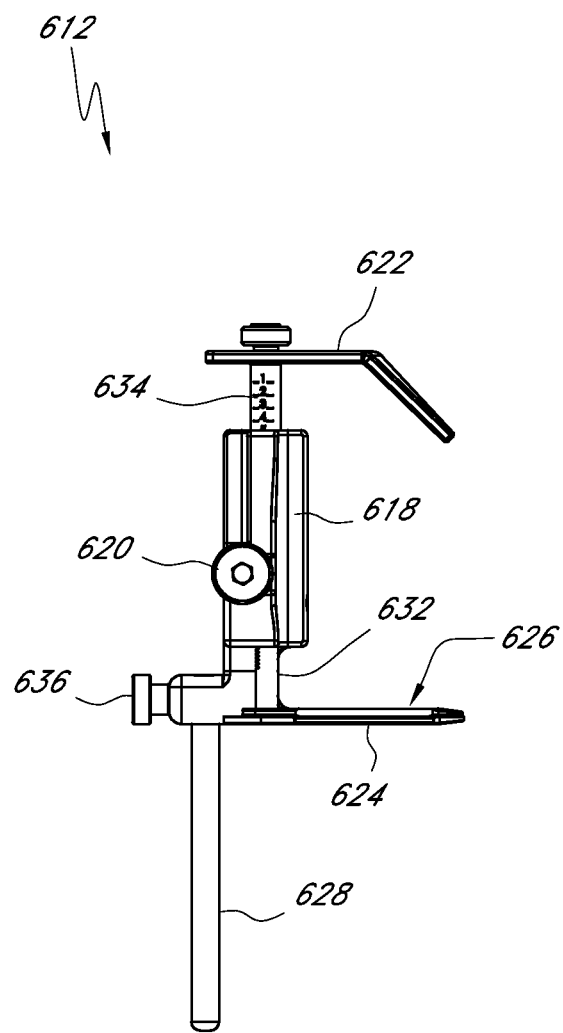
FIG. 45 is a side view of the distraction device of FIG. 44.

FIG. 45 shows a side view of the knee distraction device 612. As shown in FIG. 45, the knee distraction device 612 can comprise a sizing stylus 622. The stylus 622 can form a posterior portion of the knee distraction device 12, and can be a modular device that can be changed to approximate a desired femoral implant size and/or to accommodate anatomical differences between the left and right knee joints. The stylus 622 can reference a particular femoral implant size and a corresponding measurement along an anterior aspect of the femur. The stylus 622 can generally comprise an anterior/posterior (A/P) sizing guide, and in some embodiments can include a marking or markings 634 along an attached post. The marking or markings 634 can provide an indication of how far the stylus 622 has been raised or lowered relative to, for example, the distraction element 626. The stylus 622 can be attached to, and/or move with, the inner body portion 616. The stylus 622 can be used, for example, to help measure the needed size of a knee joint prosthetic during a knee joint replacement procedure.

The body 614 of the knee distraction device 612 can further comprise a securing device 636. The securing device 636 can comprise, for example, a knob which can be turned to lock the guide portion 628 in place. When unlocked, the guide portion 628 can slide within an opening of the outer body portion 618.

In some embodiments, the guide portion 628 can protrude at least 75 mm beyond the tibial baseplate 624. In some embodiments, the guide portion 132 can be 12.7 mm in diameter. Other diameters are also possible. In some embodiments, a cross section of the guide portion 628 can comprise a generally round portion and a generally flat portion similar to the primary rod 316 of the landmark acquisition assembly 312 described above. A portion of the guide portion 628 can be used, for example, as a handle. The guide portion 628 can be used to couple the knee distraction device 612 to the surgical orientation device 12. For example, the coupling device 14 can be attached to the guide portion 628, and the surgical orientation device 12 can be attached to the coupling device 14.

Figure 46:
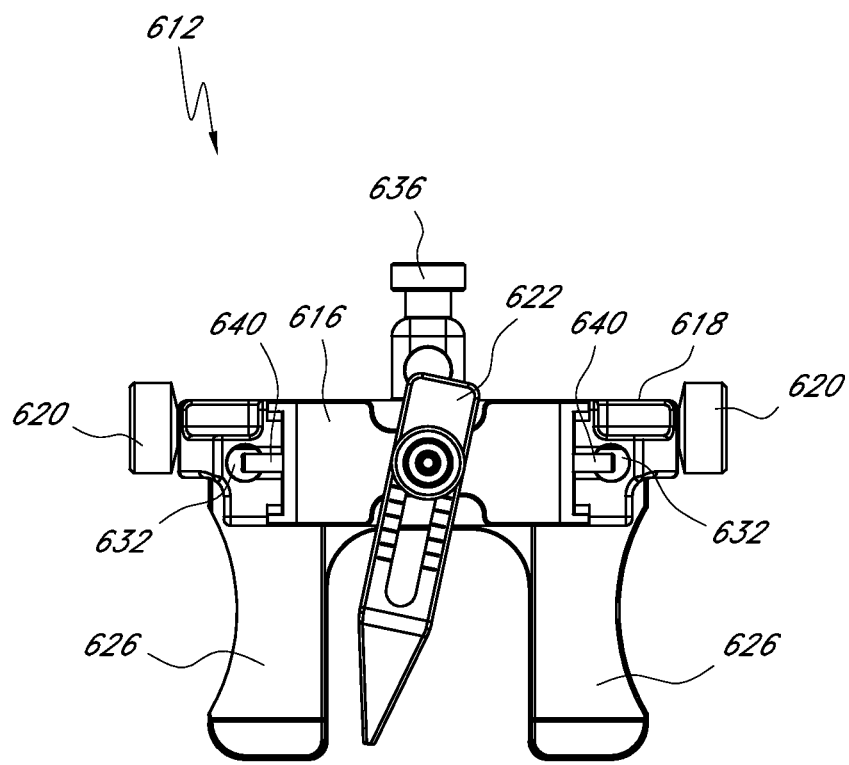
FIG. 46 is a top view of the distraction device of FIG. 44.

FIGS. 44, 45, and 46 illustrate how the inner body portion 616, outer body portion 618, and posts 632 can function together. FIG. 44 shows a channel 638 extending down the outer body portion 618 on either side of the outer body portion 618. The posts 632, which are shown extending from beneath the outer body portion 618 in FIG. 44, can extend up into these channels 638.

FIG. 45 shows a top view of the knee distraction device 612, looking down the channels 638. As illustrated, the tops of posts 632 can be seen inside the channels 638. FIG. 45 also shows extrusions 640. The extrusions 640 can form part of the inner body portion 616, and can extend partially or entirely into the channels 638.

Figure 47:
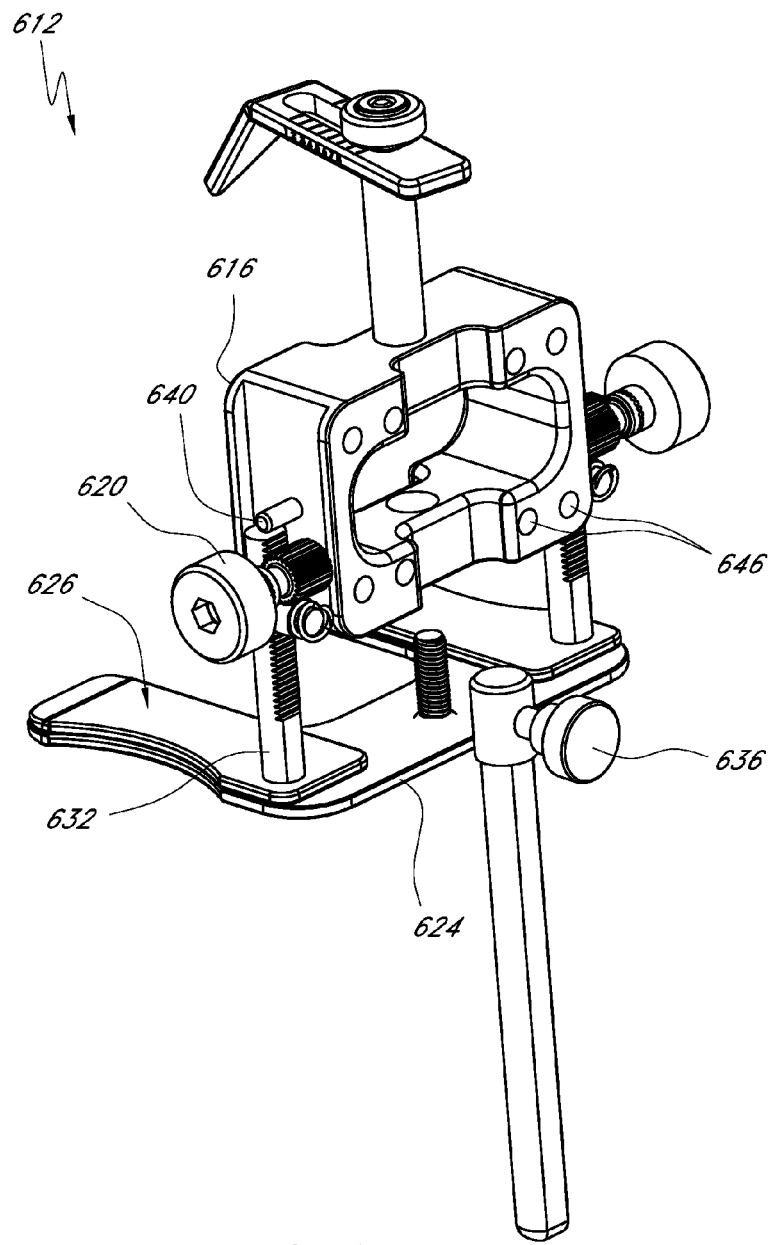
FIG. 47 is a partial perspective view of a portion of the distraction device of FIG. 44.

FIG. 47 shows the knee distraction device 612 with the outer body portion 618 removed. The extrusion 640, which extends from inner body portion 616, can rest on top of the post 632, such that as the post 632 is moved inside the channel 638, the inner body portion 616 is moved as well. In some embodiments, the adjustment device 620 and post 632 can comprise a rack and pinion-like gear system, wherein the post 632 comprises a plurality of gear teeth, and the adjustment device 620 comprises a plurality of corresponding gear teeth. When the adjustment device 620 is turned, the post 632 can be moved either up or down (e.g. proximally or distally) within the channel 638. As the post 632 moves, the post 632 can carry the inner body portion 640, and stylus 636, with it. In some embodiments, only one extrusion 640 can be used to dictate and/or facilitate movement of the inner body portion 616.

With continued reference to FIG. 47, the inner body portion 616 can comprise a modular structure or device, such as for example a sizing guide, which can be used for a specifically-sized implant or implants, and/or for a right leg or left leg only. In some embodiments, the inner body portion 616 can be removable from the knee distraction device 612. The inner body portion 616 can be used to measure femoral implant size, and can contain holes through which pins can be placed into the femur (or other bony structure) for mounting another surgical apparatus or apparatuses.

Figure 48:
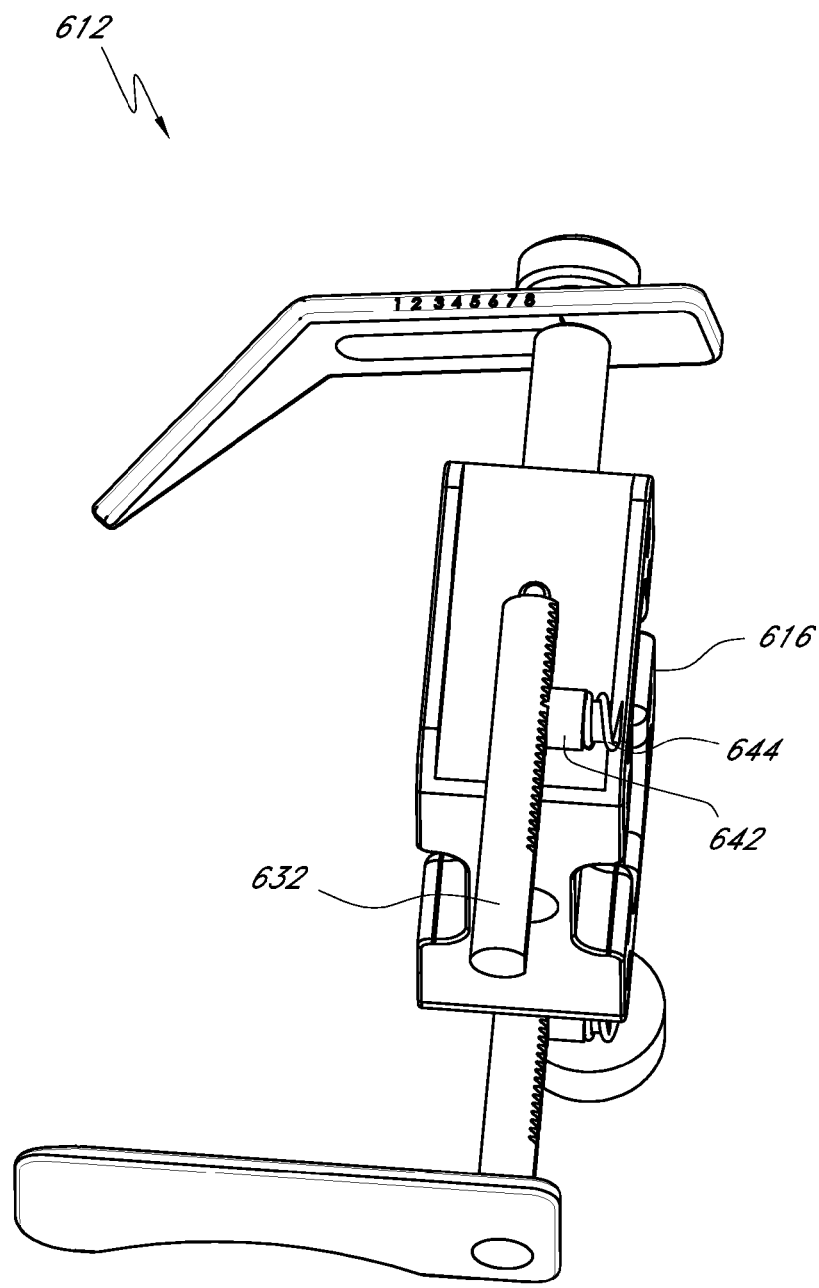
FIG. 48 is a perspective view of a portion of the distraction device of FIG. 44.

In a preferred arrangement of the knee distraction device 612, movement of the post or posts 632 can be tracked or monitored. For example, the knee distraction device 612 can provide audible and/or visual feedback to the user, indicating the degree or extent to which a post 632 and distraction element 626 have been moved relative to an initial starting position. FIG. 48 shows a pin 642 and spring 644 which can be inserted into the outer body portion 618. The spring 644 can bias the pin 642 against gear teeth along the post 632, such that as the post 632 moves up and/or down, a user can hear and/or feel an edge of the pin 642 contacting the gear teeth along the post 632. This contact can produce an audible click, or clicks. This contact can additionally or alternatively provide a force (e.g. frictional) which can hold the post 632 in a desired position, until the adjustment device 620 is turned again.

With continued reference to FIGS. 44-48, the distraction elements 626, including the foot portions 630, can be moved up and down (e.g. proximally and distally) relative to the tibial baseplate 624 by the adjustment device or devices 626. For example, the distraction elements 626 can be moved individually and independently in a vertically upwards (e.g. proximal) direction to apply pressure to the distal condyles of a femur or other bony structure in the body, and move the condyles of the femur to a desired position. This movement can distract the knee joint, surrounding soft tissue, and/or ligaments. In some embodiments, a pressure or force gauge or gauges can be incorporated with the knee distraction device 612 to determine the amount of compressive force which was applied by, or is being applied by, the distraction elements 626 against the condyles of the femur.

The knee distraction device 612 can include an indicator which indicates the distance the inner body portion 616 has traveled relative to the tibial baseplate 624 after the adjustment device or devices 20 has been turned. For example, the indicator can be in the form of markings and/or other structures or components which provide a visual or audio indication.

The knee distraction device 612 can further comprise a spring or springs which can apply a constant spring force to whatever anatomical structure or structures the distraction elements 626 are contacting. For example, each distraction element 626 can include a pre-tensioned spring, such that when the knee distraction device 612 is placed into an anatomical joint (e.g. a knee joint), the pre-tensioned springs can be released, and a constant, pre-determined pressure can be applied by the distraction elements 626 to any contacted anatomical structures (e.g. condyles). In some embodiments, the pressure applied can be approximately 70-80 psi. In other embodiments the pressure applied by can be approximately 60-90 psi. Other pressures and/or pressure ranges are also possible. The pressures applied by each spring can be different.

In some embodiments, when the knee distraction device 612 is being used to distract the knee joint, a ligament or ligaments can be released on either or both sides of the knee. The knee distraction device 100 can be used to modify the ligament(s) of the knee to provide a desired balance of forces around the knee joint.

In a preferred arrangement, the foot portions 630 can be removably attached to the posts 632. The foot portions 630 can be adjustable relative to the body 614 and/or posts 632. For example, the foot portions 630 can be longitudinally slotted, such that the foot portions 630 can be adjusted in a longitudinal direction in a plane containing the tibial baseplate 624. This adjustment can allow the foot portions 630 to be inserted into a knee joint, or other joint, at different depths, for example based on the knee joint size. By making the foot portions 630 slotted and/or adjustable relative to the posts 632, the foot portions 630 can be inserted to a particular desired depth during each step of a procedure. Furthermore, the adjustability of the foot portions 630 can enable a single pair of foot portions 630 to be used throughout a joint procedure. In other contexts, a plurality of depths can be achieved by providing a set of foot portions 630 of different lengths that can be coupled with the posts 632.

In a preferred arrangement, the foot portions 630 can additionally be rotatably adjustable. For example, the foot portions 636 can rotate in one ore more directions about the posts 632. This rotation can facilitate use of the knee distraction device 612 in knee joints which vary in size, and where for example the femoral condyles in a particular knee joint are spaced significantly far apart. This rotation can also allow the foot portions 630 to be inserted through a relatively narrow incision in the body and then spread out once inside the knee joint (e.g. rotate away from one another) to engage the femoral condyles. This rotation can inhibit the use of larger, more undesirable incisions on a patient's body, thereby leaving the patient with a smaller, less visible scar after a joint replacement procedure.

FIG. 47 illustrates an opening or openings 646. The openings 646 can be located on the inner body portion 616, and can extend through the entire inner body portion 616. While eight such openings 646 are shown in FIG. 47, different numbers, sizes, shapes, and/or locations of openings 646 can also be used.

The openings 646 can be used as drill hole and/or pin insertion guides. For example, when the knee distraction device 612 has distracted a distal femoral condyle or condyles in a knee replacement procedure, a pin or pins can be inserted into the distal femur in order to provide a mounting location for a cutting block. The openings 646 can be used as guides for insertion of these pins. The openings 646 can be spaced apart from one another in a pattern or patterns. For example, some of the openings 646 along the bottom of the inner body portion 616 can be spaced slightly higher, and/or further away from the tibial baseplate 624 than other openings 646 along the bottom of the inner body portion 616. Similarly, some of the openings 646 along the top of the inner body portion 616 can be spaced slightly higher, and/or further away from the tibial baseplate 624 than other openings along the top of the inner body portion 616. This spacing can be used, for example, to eventually control the orientation of a cutting block which is later attached to the pins.

The knee distraction device 612 described above can be biocompatible for short term exposure to the inner anatomy of the knee or other body joint, and can be sterilized by autoclave and/or gas. The weight of the knee distraction device 612 can vary. For example, in a preferred arrangement, the knee distraction device 612 can have a maximum weight of 1 kg, and can generally be lightweight for ease of operation and handling. Other maximum weights, including weights greater than 1 kg, are also possible.

The knee distraction device 612 can operate without lubricants. Materials can be selected and treated to prevent galling and provide smooth operation consistent with expectations for a high quality surgical instrument. In general, the knee distraction device 612 described above can be made robust to withstand normal and abusive use, especially rough handling during cleaning and/or sterilization. The knee distraction device 612 can be etched with part numbers, revisions levels, and company name and logo. Other markings can be added to provide clarity.

The knee distraction device 612, or other similar distraction devices, can be used in joints other than the knee joint. For example, the knee distraction device 612 can be used in the elbow, or other joint, to distract a joint.

E. Acquiring Orientation Information and Distracting a Joint Using a Femoral Preparation System During a knee joint replacement procedure, the knee distraction device 612 and femoral preparation system 610 described above can be used to align and balance the ligamentous structure of the knee joint and/or determine an orientation for a cut or cuts along the femur. In some techniques, one cut is referred to as the distal femoral cut (DFC). The DFC removes a distal (i.e., lower) portion of the femur.

Prior to using the femoral preparation system 610, and prior to the DFC, the proximal (i.e. upper) tibia can be cut. For example, and as described above, a tibial preparation system 10, 210, 310, 410, or other tibial preparation system can be used to resect a portion or portions of the tibia, such that the proximal end of the tibia comprises generally a flat plane or plateau. Based on pre-operative determinations of desired varus/valgus, posterior/anterior, and/or other angles for this tibial resection plane, the pleateau can be perpendicular to the mechanical axis, or at an angle other than perpendicular to the mechanical axis.

Prior to insertion of the knee distraction device 612 into the knee joint, an appropriately sized and/or configured inner body portion 616 can be chosen. For example, the inner body portion 616 can indicate "LEFT" for a left leg and "RIGHT" for a right leg. Additionally, prior to insertion of the knee distraction device 612, osteophytes on the femur and/or tibia can be removed to prevent obstruction and interference.

Figure 49A:
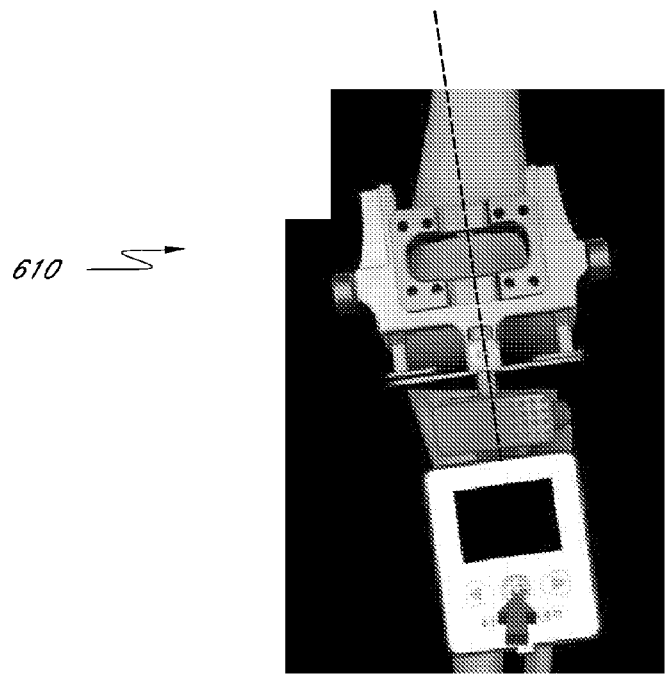
FIGS. 49A-B are anterior views of the femoral preparation system of FIG. 5 being used to distract a knee joint with visual guidance using a visual indicator, such as a laser.
Figure 49B:
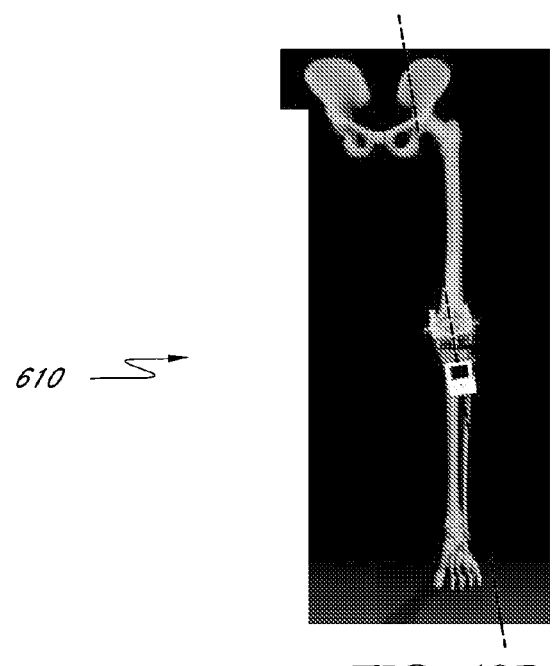

FIGS. 49*a* and 49*b* show the leg in full extension, with a portion of the knee distraction device 612 inserted into the knee joint. The distraction elements 626 are shown inserted underneath the femoral condyles, and above the tibial plateau, such that one distraction element 626 is located generally underneath one condyle, and another distraction element 626 is located generally under the other condyle. The tibial baseplate 624 is also shown inserted into the knee joint.

Prior to or after insertion of the knee distraction device 612, the laser 42 of the surgical orientation device 12 can be turned on, such that a laser beam or beams emanate from the optical element or elements 32. For example, and as shown by the arrow in FIG. 49*a*, the user can press one of the user inputs 26. The laser beams are illustrated in dashed lines in FIGS. 49*a* and 49*b*.

With reference to FIGS. 49*a*, 49*b*, 50*a*, and 50*b*, once a portion of the knee distraction device 612 is inserted into the knee joint, the distraction elements 626 can be moved up or down by turning the adjustment devices 620. For example, the distraction elements 626 can be moved away from the tibial baseplate 624 and into contact with distal aspects of the femoral condyles, thereby causing the knee distraction device 12 to apply an opposing force or forces to the proximal tibia and the distal aspect of the femoral condyles. This force or forces can distract the knee joint and its surrounding soft tissue and/or ligaments. Each distraction element 626 can be moved independently, and as described above, if desired each distraction element 626 can apply a different amount of pressure or force to each femoral condyle. In a preferred arrangement, and as described above, as a distraction element 626 moves, the distraction element 626 can cause identical movement of the inner body portion 616. In other embodiments, the inner body portion 616 can remain stationary while the distraction elements 626 are moved.

Figure 50A:
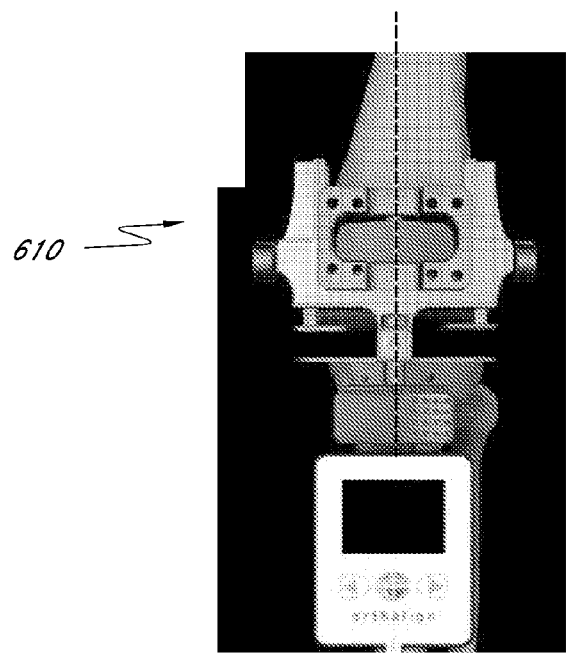
FIG. 50A is an anterior view of the femoral preparation system of FIG. 5 after the knee has been distracted.
Figure 50B:
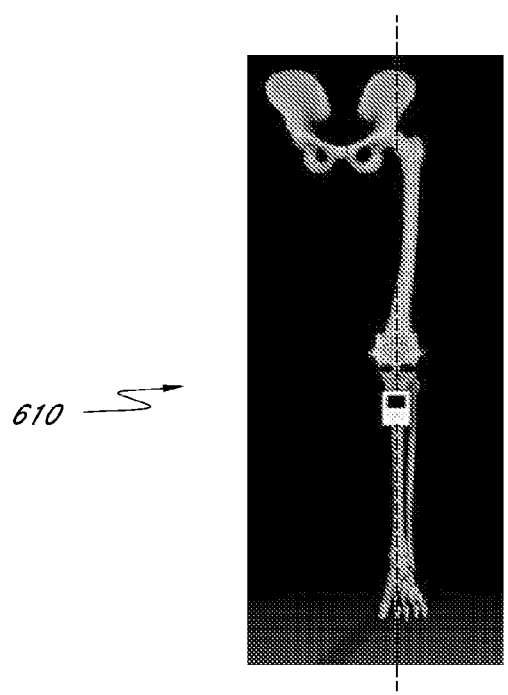
FIG. 50B is an anterior view of the femoral preparation system of FIG. 5 after the knee has been distracted.

With continued reference to FIGS. 49*a*, 49*b*, 50*a*, and 50*b*, the laser beam or beams emanating from the surgical orientation device 12 can provide an indication of, and/or facilitate, alignment of the femoral preparation system 610. For example, while the distraction elements 626 are being moved and/or adjusted, and the knee joint is being distracted, the laser beams can move towards a desired anatomical landmark or landmarks. As shown in FIG. 50*b*, one of these landmarks can be on the hip and/or femoral head, and the other can be on the foot and/or ankle. These landmarks can be used to identify an orientation of the mechanical axis. For example, if the laser beams are pointing to one or more of these landmarks, the user can have a visual indication that the surgical orientation device 12 is generally aligned with the mechanical axis. The user can also have a visual indication that a gap, or distance, between one femoral condyle and the tibial plateau is substantially identical to the gap, or distance, between the other femoral condyle and the tibial plateau. In some embodiments, the user can release one or more ligaments in the knee joint prior to or during the knee distraction in order to facilitate simultaneous symmetry of the gaps, mechanical axis alignment, and/or balancing of the soft tissue and/or ligaments in the knee joint.

During distraction, the surgical orientation device 12 can be configured to measure and display tension within the soft tissue on the medial and/or lateral sides of the knee joint. For example, the knee distraction device 612 can comprise sensors, or other structures, which can relay information to the surgical orientation device about the degree of tensile force being exerted upon the distraction element or elements 626, and/or the tibial baseplate 624. The surgical orientation device 12 can display this information, for example, on the display 24. If the tension on a medial or lateral side of the knee is too great, the user can change the tension by adjusting (e.g. turning) one or more of the adjustment members 620.

Once the distraction elements 626 have applied a desired level of pressure or force against the condyles of the femur, and/or the femoral preparation system 610 is aligned with the mechanical axis (or other axial line), a drill or other cutting tool can be used to drill holes through the openings 646 of the knee distraction device 612 into the femur. In some embodiments, the openings 646 closest to the outer body portion 618 can be used. In other embodiments, different sets of openings 646 can be used. The openings 646 which are selected can determine and/or change an orientation and/or arrangement of reference pins which are placed into the femur. This orientation and/or arrangement of reference pins can determine the orientation of a cutting block which can be attached to the reference pins after the femoral preparation system 10 is removed. For example, if the user has pre-operatively determined that a cutting plane along the distal femur should be oriented at three degrees in a varus/valgus direction relative to the mechanical axis, the user can select a set of openings 646 which provide for a three degree slope, and drill holes through these openings 646.

Figure 51A:
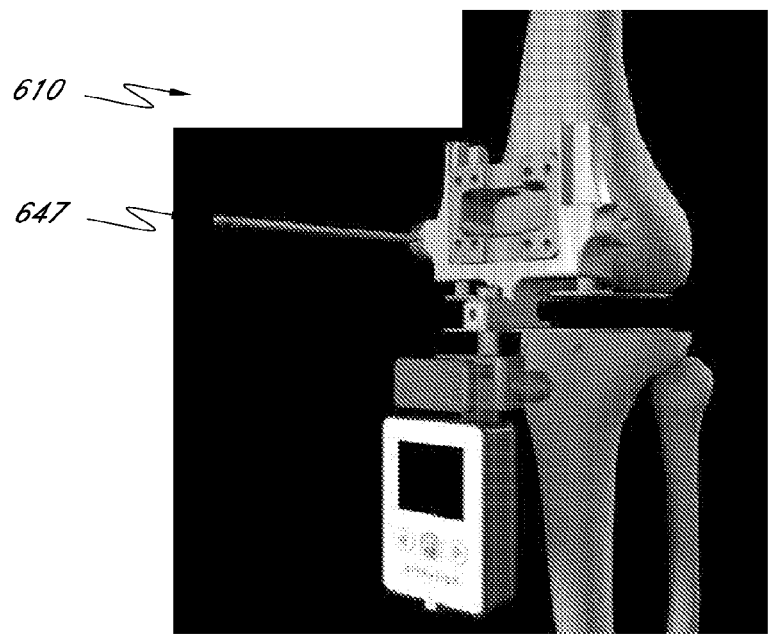
FIG. 51A is a perspective view of a first pin being inserted into an opening in the femoral preparation system of FIG. 5.
Figure 51B:
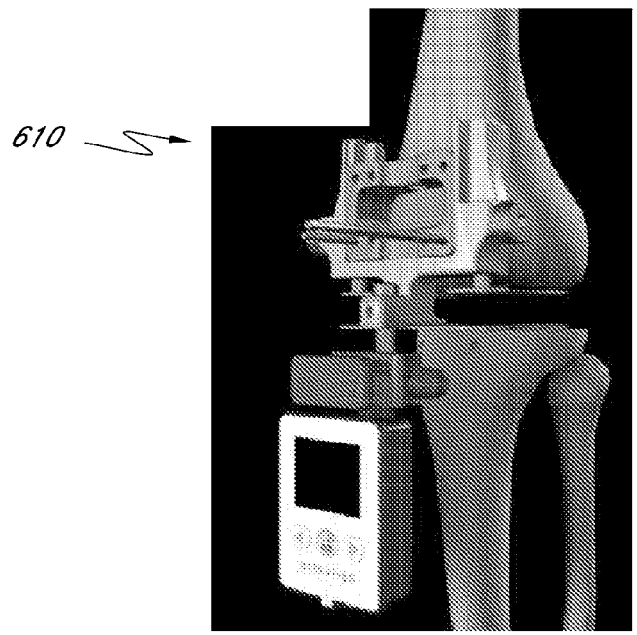
FIG. 51B is a perspective view of a second pin being inserted into an opening in the femoral preparation system of FIG. 5.
Figure 52:
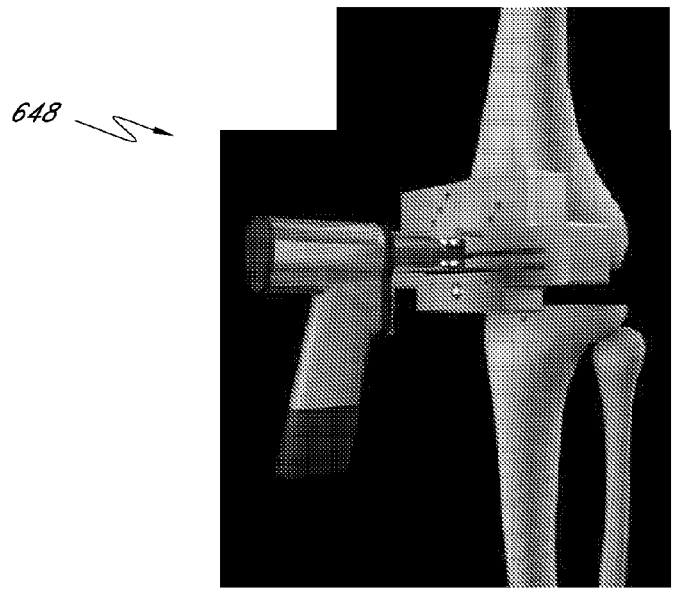
FIG. 52 is a perspective view of a cutting block and a cutting tool being used to resect a portion of the distal femur.

These drilled holes can serve as reference holes, and can be used for insertion of reference pins 647. As shown in FIGS. 51*a* and 51*b*, the reference pins 647 can be inserted through the openings 646 and into the reference holes in the femur. Once the reference pins are inserted into the femur, the femoral preparation system 610 can be removed, and a cutting block 648. The cutting block 648 can be placed onto or coupled to the reference pins. As shown in FIG. 52, once the cutting block 648 is attached, a saw or other cutting device can then be used to make an appropriate DFC cut or cuts of the femur.

Figure 53:
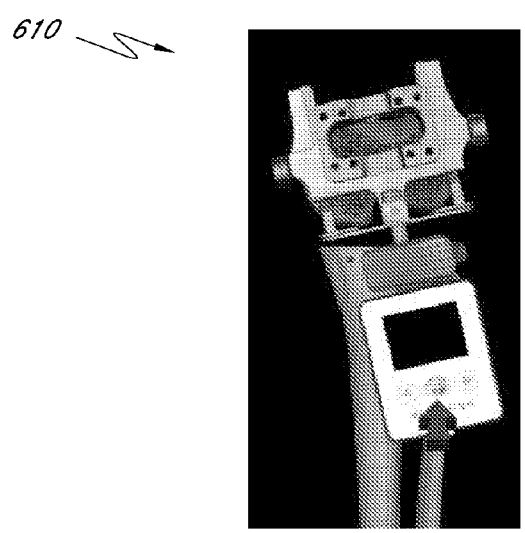
FIG. 53 is an anterior view of the femoral preparation system of FIG. 5 being used to distract a knee joint with visual guidance using a visual indicator, such as a laser.

In some knee joint procedures, another cut which can be made is a posterior femoral cut (PFC). In preparation for the posterior femoral cut, the leg can be placed in approximately 90 degrees of flexion. FIG. 53 shows the leg in flexion, with the tibial baseplate 624 and distraction elements 626 again extended inside the knee joint. The body 614 of the knee distraction device 612 can sit flush with a plateau formed on the resected femoral condyles from the DFC.

Once the knee distraction device 612 is inserted into the knee joint, the adjustment devices 626 on either side of the outer body portion 618 can be turned to individually move the distraction elements 626 away from the tibial baseplate 624, thereby distracting the knee joint and applying an individual opposing force or forces to the tibial plateau and the femoral condyles. Each condyle can be distracted individually, simultaneously, and/or consecutively.

Figures 54, 55:
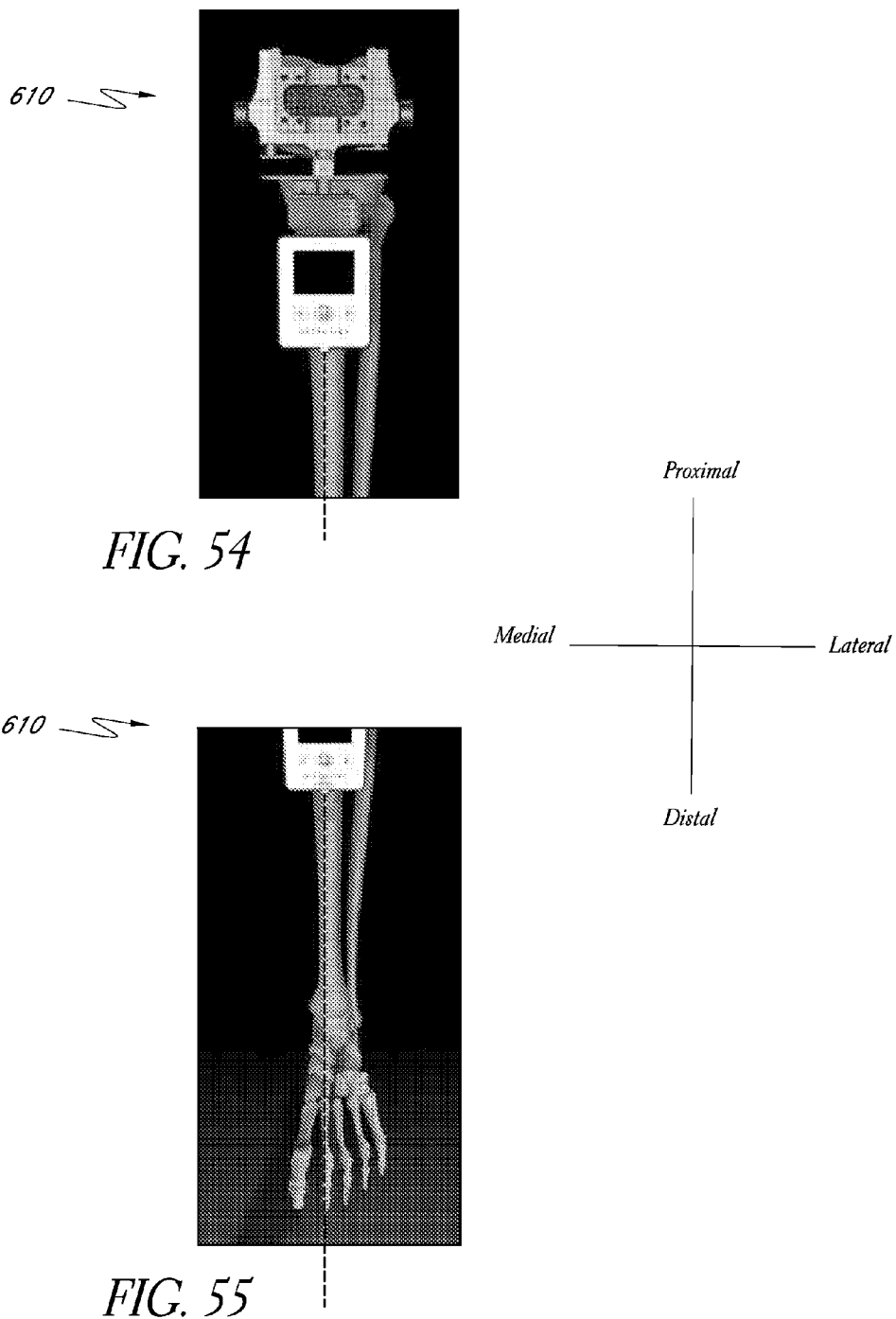
FIG. 54 is an anterior view of the femoral preparation system of FIG. 5 being used to distract a knee joint with visual guidance using a visual indicator, such as a laser.
FIG. 55 is an anterior view of the femoral preparation system of FIG. 5 being used to distract a knee joint with visual guidance using a visual indicator, such as a laser.

FIGS. 53, 54, and 55 show the knee distraction device 612 during adjustment of the distraction elements 626. As shown in FIGS. 54 and 55, the user can activate the laser 42 on the surgical orientation device 12 to facilitate alignment of the surgical orientation device 12 with the mechanical axis. For example, the knee distraction device 12 can be adjusted until a laser hits a landmark such as the area between the first and second toe on the patient's foot.

Figure 56:
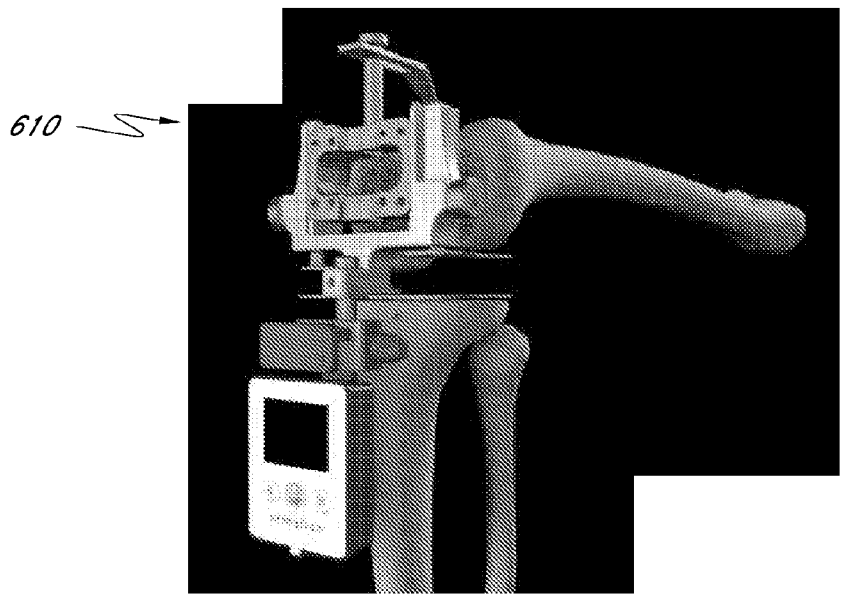
FIG. 56 is a perspective view of the femoral preparation system of FIG. 5 after the knee has been distracted.

As shown in FIG. 56, the stylus 622 can then be positioned and/or adjusted to assess a level of the anterior cortex resection. For example, with the knee joint in full flexion, the tip of the stylus 622 can be brought down and into contact with the femur. The stylus 622 can then be moved along the femur to measure or identify a desired size for the femoral knee joint prosthetic.

In some embodiments, an additional device can be used to project a laser beam or beams onto the resected distal surface of the femur to create a cross pattern. This cross pattern can be used, for example, to check the rotational orientation of the knee distraction device 612 relative to the femur by comparison of the positions of the beams relative to the epicondylar axis of the femur and a Whiteside's line.

As shown in FIG. 56, once the knee distraction device 612 is aligned with the mechanical axis, holes can be drilled into the femur, and reference pins 647 can be inserted. The reference pins 647 can be inserted into various openings 646, again depending on the desired angle of resection. For example, and as described above, some of the openings 646 can be located at slightly different levels or elevations on the inner body portion 616. Depending on where the reference pins 647 are inserted, a slightly different angle of resection can be achieved (e.g. zero degrees, plus three degrees, minus three degrees relative to a plane perpendicular to the mechanical axis in the tibia).

Figure 57:
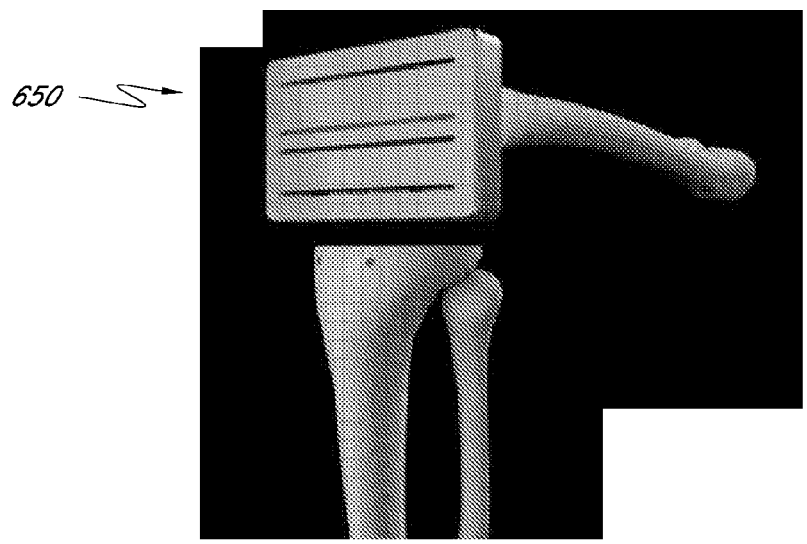
FIG. 57 is a perspective view of a cutting block which can be used to resect the distal femur.

Once the reference pins 647 are inserted, a cutting block 650 can be placed onto or coupled with the reference pins 647, for example as shown in FIG. 57. A saw or other cutting device can then make appropriate PFC cut or cuts (e.g. an anterior, additional posterior, and/or chamfer) along the femur.

IV. Attachment of Prosthetic Components

Once all of the tibial and/or femoral cuts are made with the systems and/or methods described above, a knee joint prosthetic or prosthetics can be attached to the distal femur and/or proximal tibia. The knee joint prosthetic devices can comprise a replacement knee joint. The replacement knee joint can be evaluated by the user to verify that alignment of the prosthetic components in the replacement knee joint does not create any undesired wear, interference, and/or damage to the patient's anatomy, or to the prosthetic components themselves.

V. User Interfaces

The systems and methods described above can each incorporate the use of a measuring device, such as, for example, the surgical orientation device 12. As described above, the surgical orientation device 12 can comprise at least one user input, a display and an electronic control unit. The user inputs and display, and/or the combination of the inputs, display, and electronic control unit can together form part of an interactive user interface. For example, the interactive user interface can comprise a housing (e.g., housing 20 described above), a coupling member (e.g., coupling device 14 described above) formed on or within the housing configured to removably couple the user interface to an alignment device (e.g., universal jig 16 described above), a sensor (e.g., sensor 40 described above), an electronic control unit (e.g., electronic control unit 1102 described above), a user input (e.g., user input 26 described above, which can transmit input commands to the electronic control unit), and a display (e.g., display 24 described above).

The interactive user interface can comprise a graphical user interface having an interactive window displaying on-screen graphics. For example, the interactive user interface can provide the user with a plurality of screen displays. The screen displays can illustrate the steps to be performed in a surgical procedure and can guide the user through the performance of the steps. Each screen display can comprise one or more on-screen graphics. The on-screen graphics can comprise one or more visual cues or indicators to prompt the user as to what step or steps to take next during one of the procedural methods described above. The visual cues referenced herein can comprise instructive images, diagrams, pictoral representations, icons, animations, visual cues, charts, numerical readings, measurements, textual instructions, warnings (visual and/or audible), or other data. The interactive user interface can be configured to alter attributes (e.g., color) of the on-screen graphics according to one or more data protocols. The interactive user interface can provide visual feedback to the user during performance of one or more surgical procedures. In certain embodiments, the interactive user interface can be configured to generate graphical user interface ("GUI") images to be displayed to the user. As described above, the user can interact with the surgical orientation device 12 via one or more user input devices 1114 (e.g., buttons, switches, touchscreen displays, scroll wheel, track ball, keyboard, remote controls, a microphone in conjunction with speech recognition software). The interactive user interface further can allow the user to confirm that a step has been completed (for example, by pressing a user input button). The interactive user interface can allow the user to enter data (e.g., a numerical value, such as a distance, an angle, and/or the like), verify a position of the surgical orientation device 12, turn a visible alignment indication system on and off, and/or turn the entire surgical orientation device on and off. In certain embodiments, the interactive user interface provides one or more drop-down lists or menus from which a user can make selections. For example, the user can make selections from a drop-down list using a scroll wheel, trackball, and/or a series of button presses. In some embodiments, the user interface provides a drop-down list of predicates that dynamically updates based on user input.

In at least one embodiment, a module for creating an interactive user interface can comprise a computer readable medium having computer readable program code embodied therein. The computer readable program code can comprise a computer readable program code configured to display one or more of a plurality of GUI images on a user interface of a surgical orientation device, the GUI images comprising instructive images related to the performance of a surgical procedure. The computer readable program code can be configured to receive instructions from a user identifying the surgical procedure to be performed (e.g., which joint and/or right or left). The computer readable program code can be configured to show the user steps to be performed in the identified process for the identified surgical procedure. The computer readable program code can be configured to guide the user in performance of the steps. For example, the computer readable program code can be configured to receive from the user an instruction to continue to the next step in the procedure, to receive orientation data from a sensor mounted within the surgical orientation device, and to display the orientation data on the user interface of the surgical orientation device.

In at least one embodiment, the surgical orientation device 12 described above can comprise a display module configured to display information and a sensor module configured to monitor the position and orientation of the surgical orientation device 12 in a three-dimensional coordinate reference system, and to generate orientation data corresponding to the monitored position and orientation of the surgical orientation device. The surgical orientation device 12 can further comprise a control module configured to receive the orientation data from the sensor module and convert it to objective signals for presentation on the display module, the control module also configured to display a set of GUI images or other on-screen graphics on the display module, the GUI images or on-screen graphics representing the orientation data received from the sensor module and also representing instructive images related to the performance of the joint replacement surgery.

In at least one embodiment, the surgical orientation device 12 can receive orientation data from a sensor module, receive input commands from a user input module to store orientation data from a user input module, convert the orientation data to a human readable format for presentation on a display device, and display on the display device on-screen graphics or GUI images for communicating information to a user based on the input commands and the orientation data, the information comprising instructive images for performing a joint replacement surgery and one or more visual indicators of a current orientation of the display device with respect to a fiducial, or reference, orientation.

In at least one embodiment, the surgical orientation device 12 described herein can comprise a sensor module attached to an alignment jig and configured to measure and record a fiducial orientation and to continuously collect orientation data of the surgical orientation device, a display module configured to display at least one visual indicator of the orientation of the surgical orientation device with respect to the fiducial, or reference, orientation, the display module further configured to display instructive images of one or more steps to be performed by the surgeon during the joint replacement surgery, and a control module configured to receive the orientation data and to convert the orientation data to objective signals for presentation on the display module.

Figures 58A, 58B, 58C:
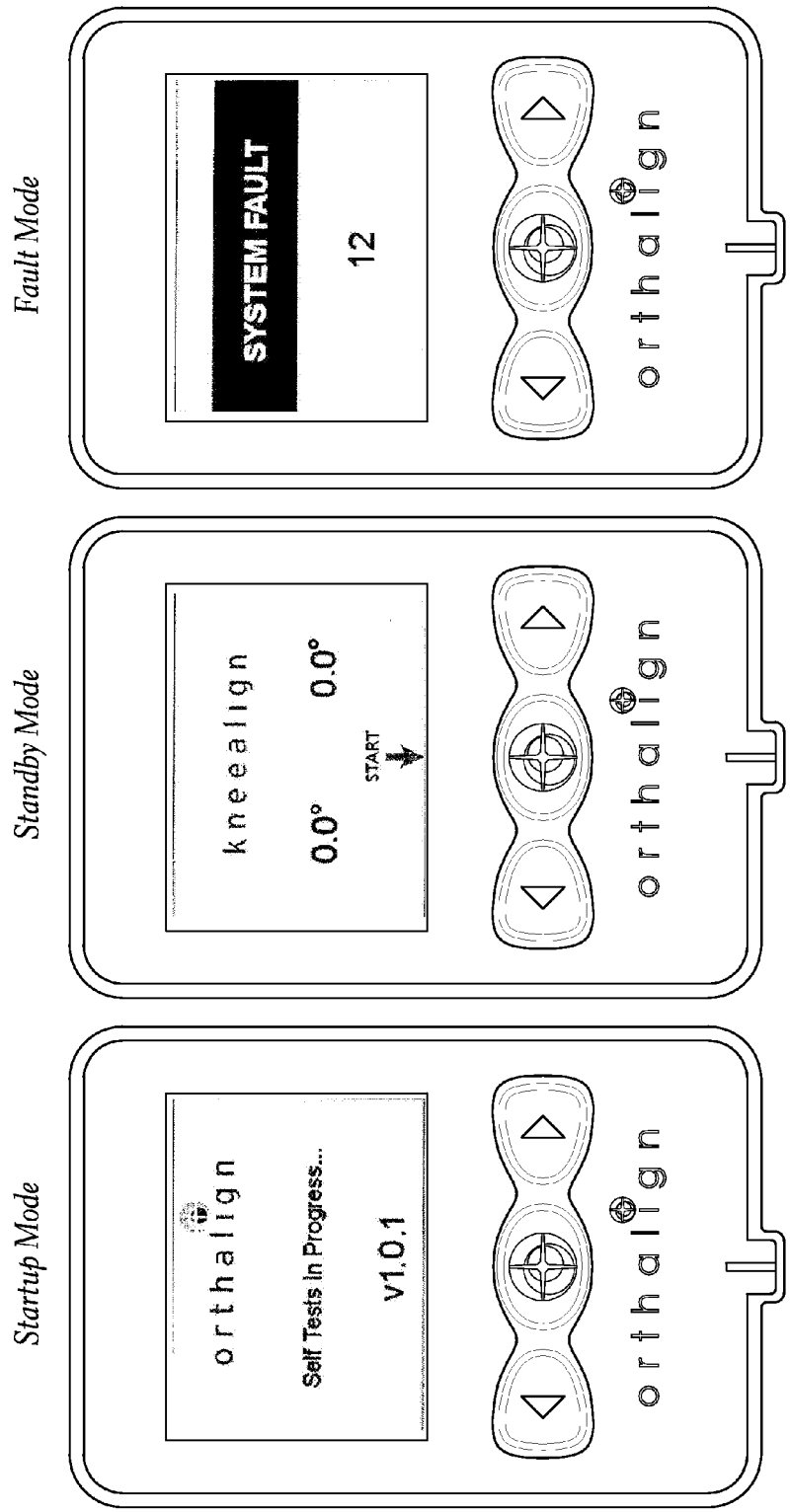

FIG. 58A-61K show various screen shots which can form part of the interactive user interface or interfaces described above. For example, FIGS. 58A, 58B, and 58C illustrate display screen shots for assisting a user in using a measuring device, for example the surgical orientation device 12. The screen shots can be seen, for example, on a display of the measuring device when the device is in startup mode, standby mode, and system fault mode (e.g., system failure mode), respectively.

As shown in FIG. 58A, an interface screen can illuminate in response to pressing a user input, e.g., a center button on the surgical orientation device 12. Thereafter, a message can be displayed indicating to the user that the surgical orientation device 12 is preparing for operation. The message can be a display of text on a screen, as illustrated in FIG. 58A, an audible sound, or other signal to the user to wait for the device to confirm a proper operational state. For example, a variety of self-tests can be performed. In one embodiment, information about the operating system, such as its version, can be displayed for review.

FIG. 58B shows an operational state of the surgical orientation device 12 in which the surgical orientation device 12 is ready to receive input indicating that a procedure can begin. The surgical orientation device 12 can be configured to prompt the user to initiate operation when ready, for example by pressing a user input 26. In one embodiment of a surgical orientation device 12, the user input 26 can comprise a button provided on a front face of the surgical orientation device 12. The image in FIG. 58B can be displayed in response to pressing a center button of the surgical orientation device 12 while the image on FIG. 58A is displayed. In other embodiments, the user can press one or more buttons while the image in FIG. 58A is displayed in order to initiate the surgical orientation device 12 for use with surgical procedures for different joints (e.g. right knee joint, left knee joint, right hip joint, left hip joint, either right or left hip joint). For example, the user can toggle among displays for each joint until the setting for the appropriate joint is found. In the standby mode of FIG. 58B, the display 24 can provide an on-screen graphic of one or more parameters to be used during the procedure. For example, a numerical display can be provided for one or more angles, such as flexion-extension angles, varus-valgus angles, or rotation angles (e.g. angles of rotation about the mechanical axis of the leg). The on-screen graphic can comprise alphanumeric text or symbols of various colors, one or more background colors, one or more icons, one or more GUI images, animations, arrows, and the like.

FIG. 58B also illustrates that textual instructions regarding how to begin a procedure once the type of procedure has been selected. For example, a visual cue can be provided on the display 24 to start a procedure. FIG. 58B shows that the word "START" can be displayed along with an arrow pointing toward a button or other device.

FIG. 58C illustrates a visual notification or warning screen. In certain embodiments, the color of the background of the display can be changed when the device is operating in the fault mode. The interactive user interface can also provide an audible alarm or other audible indication to the user when the device is in a system fault mode. This display screen can be configured such that the screen is displayed when the surgical orientation device 12 fails to pass a self test or tests that can automatically be initiated by the surgical orientation device 12 before or during use of the surgical orientation device 12.

FIG. 59A shows a display screen shot which can instruct the user to position a surgical instrument, for example, an extramedullary device (e.g. the extramedullary alignment guide 313) and/or a cutting block, on the tibia. In one embodiment, the display screen shot can include an image of the tibia and the surgical instrument displayed adjacent to a particular aspect of the tibia (e.g., the anterior surface). The instructive images in FIG. 59A can be displayed in response to pressing a button located immediately below the arrow displayed in FIG. 58B. In a preferred arrangement, the user can move from one screen to the following screen by pressing a button indicated below an arrow displayed on the current screen, and can navigate back to prior screens by pressing a different button on the surgical orientation device 12 (for example a left arrow or BACK button). In certain embodiments, a user can power off the display screen by pressing two different buttons simultaneously.

FIG. 59B shows a display screen shot which can instruct the user to provide an orientation assembly (e.g. tibial preparation system 310a). In one method, the user can be provided with an image of the surgical orientation device 12 or other measuring device and the landmark acquisition assembly 312, and the visual cues of FIG. 59B can instruct the user to couple these structures together. The visual cues can include an animation or series of animations. The screen shot illustrated in FIG. 59B, as well as other screen shots described herein, can illustrate that the user interface can include a combination of visual cues or indicators to provide instructions to the user. For example, text can be provided along with instructive images or icons. In some embodiments, either text or visual cues can be provided alone. In another embodiment, audible cues can be provided alone or in combination with text and/or visual cues. The audible cues can comprise, for example, speech, a buzzer, or an alarm.

FIG. 59C shows a display screen shot which can instruct the user to position an orientation assembly (e.g. tibial preparation system 310a) in a coronal plane of the tibia and to direct the surgical orientation device 12 or other measuring device to acquire the coronal plane of the tibia. The instructive images in FIG. 59C can be displayed in response to pressing the central button located immediately below the arrow displayed in FIG. 59B.

In one method, such as one of the methods described above, the user can be provided with a surgical orientation device 12 or other measuring device and a landmark acquisition assembly 312, coupled together. The visual cues of FIG. 59C can instruct the user to position the tibial preparation system 310a with respect to the tibia by palpating and placing a tip 326 of a secondary rod 320 of the landmark acquisition assembly 312 on the location of attachment of the lateral collateral ligament to the proximal fibular head, and placing a second tip 326 on the apex of the lateral malleolus.

FIG. 59C can further instruct the user to press a button of the surgical orientation device 12 indicated by the screen (for example by a green arrow) to direct the surgical orientation device 12 to acquire the coronal plane of the tibia. In one embodiment, the user interface can provide information on the status of the process of acquiring the coronal plane, as well as instruction for operation of the surgical orientation device 12. For example, the bottom right hand corner of the display 24 can provide information on the status of the acquisition of the coronal plane. The information on the screen regarding the status of the acquisition of the coronal plane can be designed to attract the attention of the user by, for example, flashing a first color such as green to indicate that the surgical orientation device 12 is aligned and a second color, such as grey, to indicate that the surgical orientation device 12 is out of alignment.

This color indication can be combined with a more specific visual cue such as the visual depiction of the degree of alignment of the surgical orientation device. After the user has pressed a button on the surgical orientation device directing the surgical orientation device 12 to acquire the coronal plane, the surgical orientation device 12 can initiate a recording of the output of one or more sensors. Such recording can follow the application of a data protocol that is selected to minimize error in the measurement, e.g., excluding transient reading and processing readings over a period, such as by employing median and averaging techniques or stabilization algorithms as described above or otherwise manipulating the readings. In certain embodiments, the data protocol is selected to record in memory the last stable data measurement received before the button was pressed.

In addition, in certain embodiments, the screen in FIG. 59C can provide the user with feedback as to whether the surgical orientation device 12 is being maintained parallel (e.g. within an allowable range) to the coronal plane of the tibia. For example, the display 24 can provide the user with feedback on the rotation (e.g. roll) of the surgical orientation device 12 about a first axis. Instead of displaying a degree measurement, the display 24 can be configured to display a pictorial representation of a bubble that, for so long as the surgical orientation device 12 remains parallel to the coronal plane of the tibia within an allowable range, stays within the confines of two vertical lines, one line on either side of the bubble. The two vertical lines marking the confines of the "level" orientation range can correspond to a relative angle or tilt of plus and minus three degrees or plus and minus one degree, for example. If the bubble moves beyond either of these lines, the background color of the display 24 behind the bubble can change, for example, from green to amber, to indicate that the orientation is out of the acceptable range.

FIG. 59C also shows that a visual cue which can be provided to the user that the surgical orientation device 12 is in the process of acquiring the coronal plane. For example, the text "ACQUIRING" can appear on the display 24. The text "ACQUIRING" can instruct the user to continue to maintain the orientation of the surgical orientation device 12 so that the surgical orientation device 12 is aligned with the coronal plane.

Figures 59D, 59E, 59F:
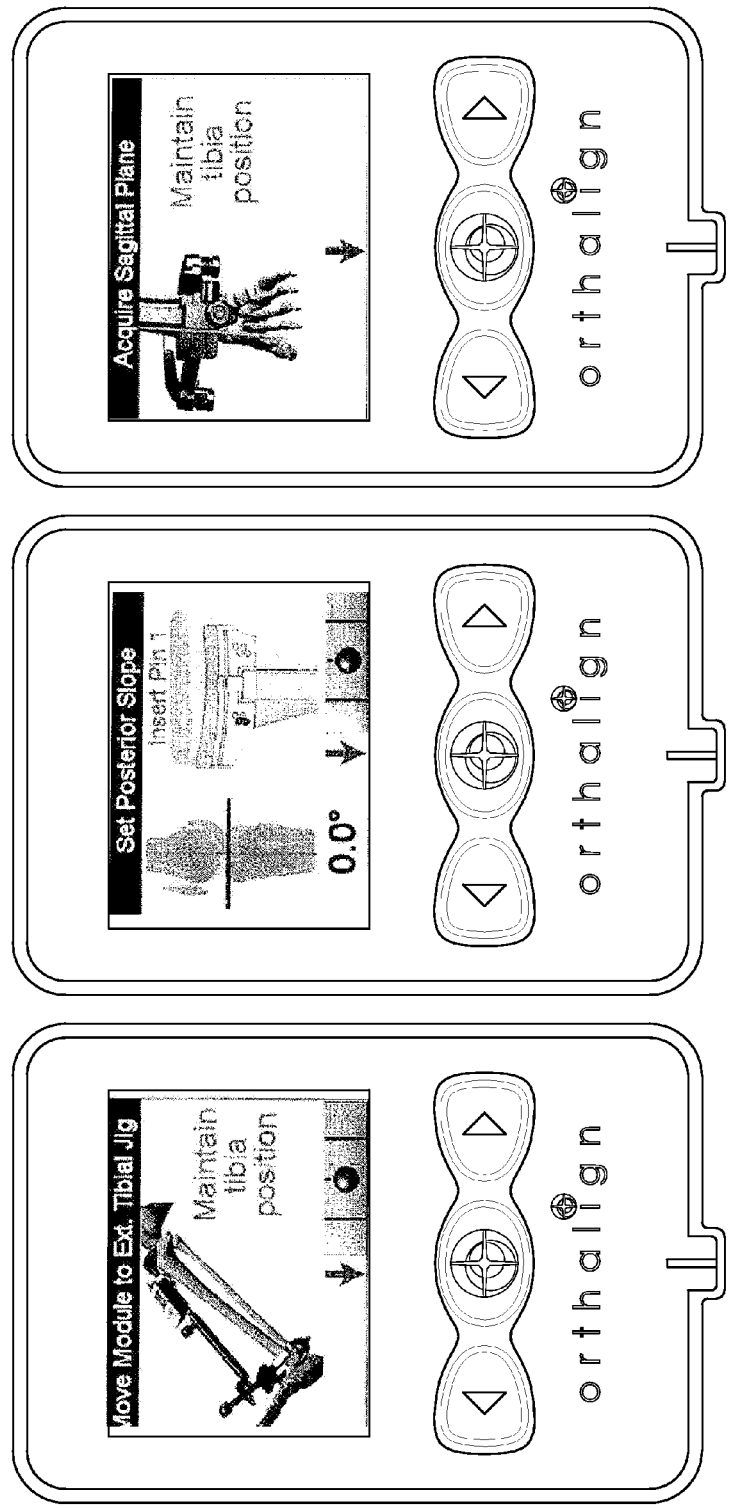

FIG. 59D shows a display screen shot which can instruct the user to reposition or move the surgical orientation device 12, or other measuring device, such that the surgical orientation device 12 is attached to a surgical instrument (e.g. extramedullary alignment guide 313) on the tibia. The on-screen graphic of images and visual cues of FIG. 59D can be displayed in response to pressing the central button located immediately below the arrow displayed in FIG. 59C.

In one embodiment, the screen shot in FIG. 59D can comprise a visual cue or indicator which can comprise an image of the tibia and the surgical instrument displayed adjacent to a particular aspect of the tibia (e.g., the anterior surface), with the surgical orientation device 12 or other measuring device coupled with an anterior surface or side of the surgical instrument.

FIG. 59D can also show a visual cue which can instruct the user to maintain the tibia in its current position while carrying out the other instructions of FIG. 59D. Maintaining the tibial position at this stage of the procedure can be one way of minimizing error in the use of data acquired by the surgical orientation device 12. In certain embodiments of the surgical orientation device 12, the screen in FIG. 59D can provide feedback as to whether the surgical orientation device 12 is being maintained parallel (e.g. within an allowable range) to the coronal plane of the tibia, for example by employing the same bubble pictorial method, or GUI image, described for FIG. 59D above. Such feedback can inform the user of any unacceptable rotation (e.g. roll) of the surgical orientation device 12.

FIG. 59E shows a display screen shot which can inform the user to set the posterior slope of a cutting block (e.g. cutting block 84) or other surgical instrument operatively coupled to the anterior side of the tibia. The instructive images in FIG. 59E can be displayed in response to pressing the central button located immediately below the arrow displayed in FIG. 59D.

For example, the bottom left hand corner of the screen shown in FIG. 59E can provide a degree measurement of the posterior slope being set by the user in real time as the surgical instrument (e.g. extramedullary alignment guide 313) and surgical orientation device 12 are adjusted, and can inform the user to insert a first pin through the cutting block and into the proximal tibia. In certain embodiments, the screen in FIG. 59E can provide feedback as to whether the surgical orientation device 12 is being maintained parallel (e.g. within an allowable range) to the coronal plane of the tibia, for example by employing the same bubble pictorial method described for FIG. 59C. Such feedback can enable the user to control variation in the rotation (e.g. roll) of the surgical orientation device 12 within an acceptable limit. FIG. 59E shows an animated depiction of the pin being inserted through the cutting block and into the proximal tibia, to suggest its insertion by the user. A text instruction and/or audible signal can be provided instead of, or in addition to, the animated depiction. For example, a text instruction can be combined with an animated depiction to provide a more comprehensive visual cue.

FIG. 59F shows a display screen shot which can instruct the user to command the surgical orientation device 12 to acquire a sagittal plane of the tibia. As described above, the sagittal plane can be a plane extending through anterior and posterior surfaces of the tibia and including the portion of the mechanical axis extending through the tibia. The images in FIG. 59F can be displayed in response to pressing the central button displayed in FIG. 59E.

The display screen shot shown in FIG. 59F can also instruct the user to maintain the tibia in its current position as a way of minimizing errors that might result from movement of the tibia. Such a visual cue can include, for example, a text instruction located at the top of the screen and an arrow directed at a button. Pressing a button can activate a light source on the device (e.g. laser 42), which can be directed distally. For example, the surgical orientation device 12 can include three user inputs 26 in the form of buttons extending from left to right across the surgical orientation device 12, and the arrow can direct the user to press the button furthest to the right.

Figures 59G, 59H:
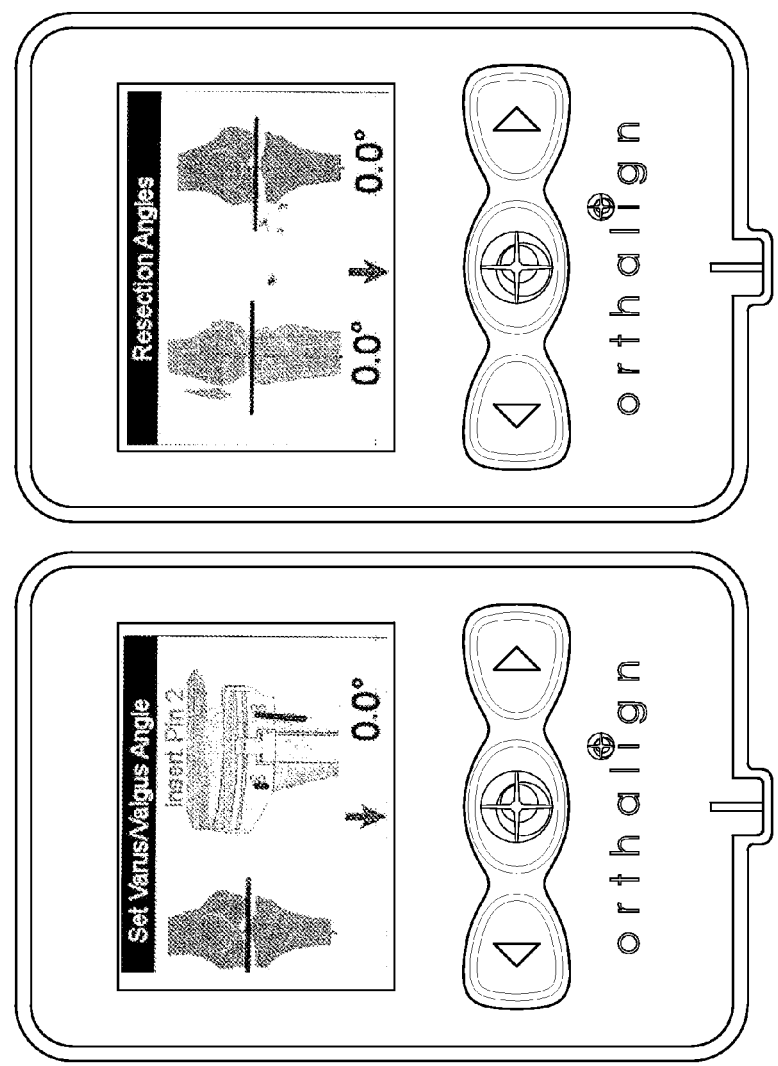

FIG. 59G shows a display screen shot which can instruct the user to set the varus/valgus angle of the cutting block (e.g. cutting block 84) or other surgical device. The images in FIG. 59G can be displayed in response to pressing the central button displayed in FIG. 59F.

The bottom right hand corner of the screen shown in FIG. 59G can provide a real-time degree measurement of the varus/valgus angle of the surgical orientation device 12 and the cutting block. This degree measurement can correspond to the varus/valgus angle of a cutting plane. The pictorial representation of the proximal tibia and cutting block at the right of the screen can informs the user to insert a second pin through the block and into the proximal tibia. FIG. 59G can also provide an animated depiction of the second pin being inserted through the block and into the proximal tibia, to suggest its insertion. The left-hand portion of the screen can show the varus/valgus angle of the surgical orientation device 12 and the cutting block graphically.

FIG. 59H shows a display screen shot illustrating a degree measurement of the angles of proximal tibia resection, based on the angle of the surgical orientation device 12 and the cutting block with respect to the tibia. In one embodiment, the screen can provide both the anterior-posterior angle and the varus/valgus angle of the cutting block both in degree measurement and pictorially. The images in FIG. 59H can be displayed in response to pressing the central button displayed in FIG. 59G.

FIGS. 60A, 60B, 60C, and 60D show display screen shots that can be displayed by the interactive user interface of the surgical orientation device 12 or other measuring device in connection with preparation of a portion of a joint. For example, the screen shots shown in FIGS. 60A, 60B, 60C, and 60D can be displayed in connection with a femoral cut and/or knee distraction as described above. In at least one knee procedure, various steps can be performed by the user prior to the user interface interactions illustrated in FIGS. 60A, 60B, 60C, and 60D. For example, a tibial resection can be performed using one of the systems and/or methods described above. After these procedures are complete, the user can use and refer to the display screens of FIGS. 60A, 60B, 60C, and 60D.

Figures 60A, 60B, 60C:
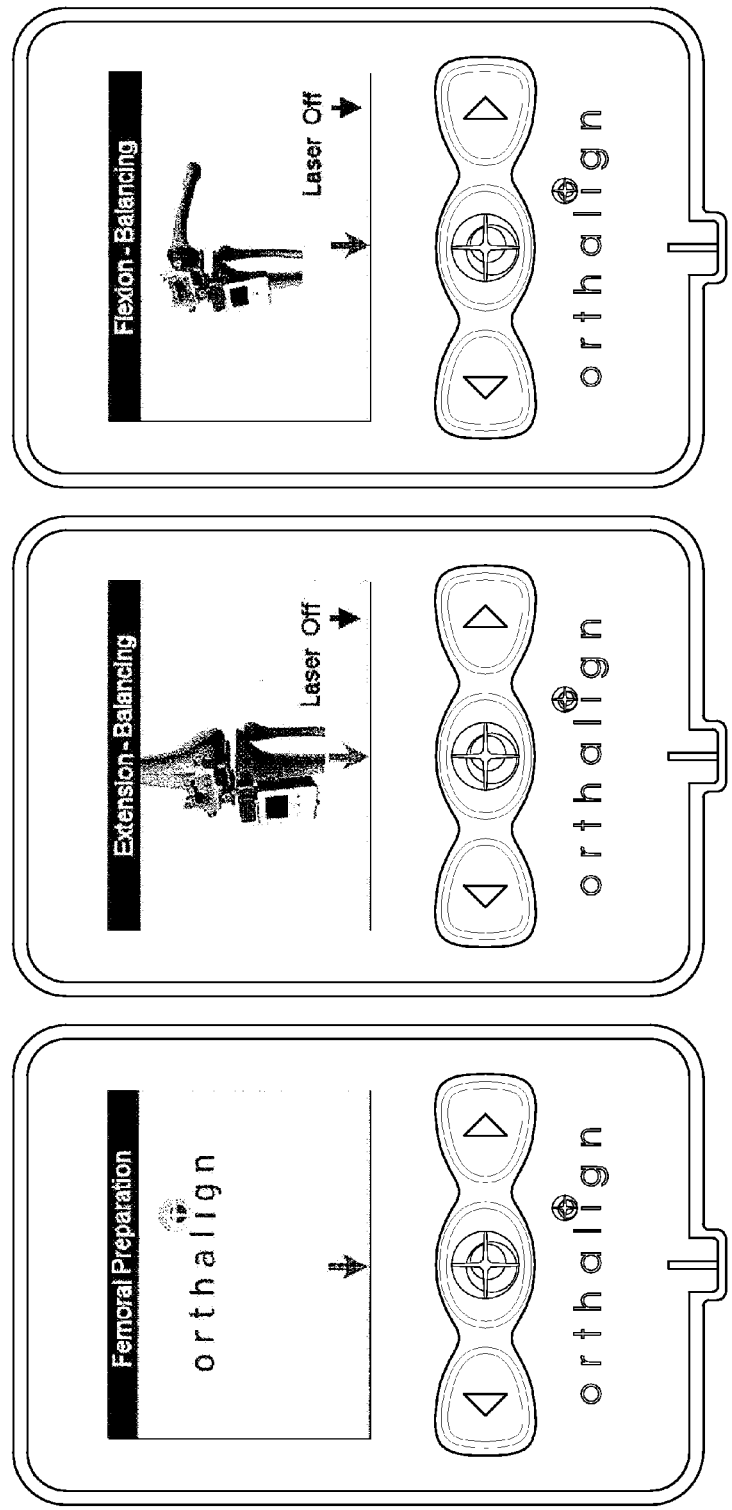

FIG. 60A shows a display screen shot which can inform the user that the surgical orientation device 12 is in a "Femoral Preparation" mode, and can provide an image of an arrow instructing the user to push a button (e.g., a center button on the surgical orientation device 12) when the user is ready to continue the procedure. The images in FIG. 60A can be displayed, for example, in response to pressing the central button displayed in FIG. 59H.

FIG. 60B shows a display screen shot which can, for example, inform the user that the surgical orientation device 12 is in an "Extension-Balancing" mode. The images in FIG. 60B can be displayed in response to pressing the central button displayed in FIG. 60A.

The display screen shot shown in FIG. 60B can provide a visual cue informing the user that the knee being operated on can be in an extension position and that a knee distraction device (e.g. knee distraction device 612), coupled with the surgical orientation device 12, can be inserted into the knee joint and into contact with the femur.

FIG. 60B can further illustrate a visual cue instructing the user to adjust the knee distraction device to balance the tension between the ligaments in the knee. For example, the screen shot shown in FIG. 60B can contain a visual cue directing the user to align a tibial laser, which can shine distally from the surgical orientation device 12 along the direction of the tibia, and a femoral laser, which can shine proximally from the surgical orientation device 12 along the direction of the femur, with certain landmarks on the body. The display screen shot shown in FIG. 60B can also display information indicating that a user input 26 (e.g. button) can be pushed on the surgical orientation device 12 to turn the laser off.

FIG. 60C shows a display screen shot which can, for example, inform the user that the surgical orientation device 12 is in a "Flexion-Balancing" mode. The images in FIG. 60C can be displayed in response to pressing the central button displayed in FIG. 60B.

The display screen shot shown in FIG. 60C can provide a visual cue informing the user that the knee being operated on can be in a flexion position and that a knee distraction device (e.g. knee distraction device 612), coupled with the surgical orientation device 12, can be inserted into the knee joint and into contact with one or more femoral condyles. The display screen shot shown in FIG. 60C can further illustrate a visual cue instructing the user to adjust the knee distraction device to balance the tension between the ligaments in the knee. For example, the surgical orientation device 12 can contain a visual cue directing the user to align a tibial laser, which can shine distally from the measuring device along the direction of the tibia, with one or more landmarks on the body. The display screen shot shown in FIG. 60C can also display information indicating that a user input 26 (e.g. button) can be pushed on the surgical orientation device 12 to turn the laser off.

Figure 60D:
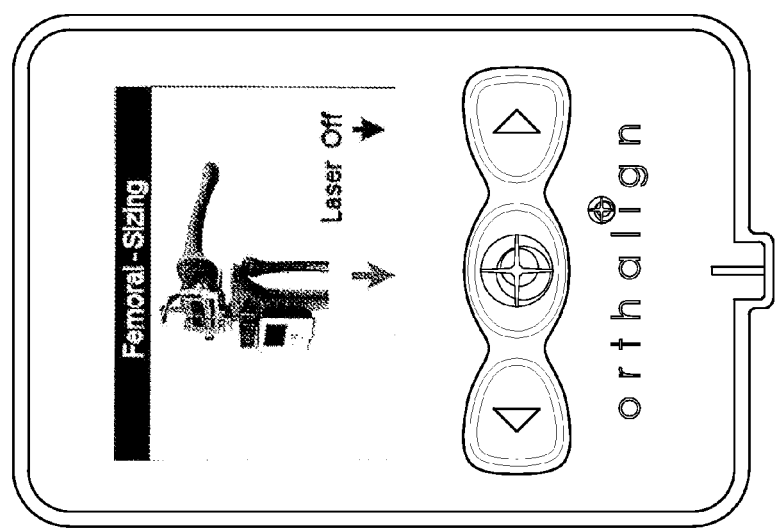

FIG. 60D shows a display screen shot which can, for example, inform the user that the surgical orientation device 12 is in a "Femoral-Sizing" mode, and can illustrate a flexed knee being sized. The sizing can be accomplished in any suitable manner, such as by using a stylus. The display screen shot shown in FIG. 60D can also display information indicating that a user input 26 (e.g. button) can be pushed on the surgical orientation device 12 to turn the laser off. The images shown in FIG. 60D can be displayed in response to pressing the central button in FIG. 60B.

FIGS. 61A-K show display screen shots that can be displayed by the user interface of the surgical orientation device 12 or other measuring device in connection with preparation of a portion of a joint. For example, the screen shots shown in FIGS. 61A-K can be displayed in connection with a tibial preparation described above.

FIG. 61A shows a display screen shot which can, for example, inform the user that the surgical orientation device is in a joint selection mode. The user can select which knee (right or left) will be operated on by pressing a user input 26 on the surgical orientation device 12. For example, the user can press a left button for the left knee, and a right button for the right knee.

FIG. 61B shows a display screen shot which can provide a visual cue informing the user that an orthopedic fixture (e.g. universal jig 16) can be assembled, if it has not already been assembled. The images in FIG. 61B can be displayed in response to pressing a button located immediately below the arrow or arrows displayed in FIG. 61A.

FIG. 61C shows a display screen shot which can provide a visual cue informing the user that the universal jig 16 can be coupled to the surgical orientation device 12, for example with the coupling device 14 described above. The images in FIG. 61C can be displayed in response to pressing a button located immediately below the arrow displayed in FIG. 61B.

FIG. 61D shows a display screen shot which can provide a visual cue informing the user that a tibia preparation system (e.g. tibia preparation system 10) can be positioned adjacent an anterior surface of the tibia. For example, the screen in FIG. 61D can provide a visual cue informing the user that the tibial preparation system 10 can be positioned and/or moved until the surgical orientation device 12 is generally centered with the insertion of an anterior cruciate ligament and a medial tibial insertion of the patella tendon in a patient's knee.

The images in FIG. 61D can be displayed in response to pressing a button located immediately below the arrow displayed in FIG. 61C. In a preferred arrangement, the user can move from one screen to the following screen by pressing a button indicated below an arrow displayed on the current screen, and can navigate back to prior screens by pressing a different button on the surgical orientation device 12 (for example a left arrow or BACK button).

In some embodiments, the screen in FIG. 61D, or other screens, can provide the user with feedback as to whether the surgical orientation device 12 is being maintained parallel (e.g. within an allowable range) of an anatomical plane. For example, in one embodiment, the user interface can provide information on the status of the process of acquiring the coronal and/or sagittal planes containing the mechanical axis, as well as instructive images or textual instructions regarding operation of the surgical orientation device 12 or steps to be performed in a surgical procedure.

In some embodiments, the interactive user interface can be configured to display a red "shaky hand" on-screen graphic or icon to indicate to the user that the device is not currently receiving stable measurements. In certain embodiments, the electronic control unit 1102 can be configured to ignore user attempts to register or record reference angles when the "shaky hand" icon is being displayed. The display 24 can also provide a textual, audible, or other visual notification to the user that the current measurements are unstable. As one example, the background color of the display screen or the color of the measurement readings can be changed when the current measurements are unstable.

As described above, the display 24 can display an on-screen graphic of a bubble (as described above) that, for so long as the surgical orientation device 12 remains parallel to the coronal and/or sagittal plane of the tibia within an allowable range, stays within the confines of two vertical lines, one line on either side of the bubble. If the bubble moves beyond either of these lines the background color of the display 24 behind the bubble can change, for example, from green to amber, to indicate that the orientation is out of the acceptable range.

FIG. 61E shows a display screen shot which can provide a visual cue informing the user that a centering stylus, or other measuring device (e.g. measuring device 109a), can be used to measure a first distance from an A/P point on top of the tibia to an optical element 32 on the surgical orientation device 12. The images in FIG. 61E can be displayed in response to pressing a button located immediately below the arrow displayed in FIG. 61D.

FIG. 61F shows a display screen shot which can provide a visual cue informing the user that a target probe (e.g. target probe 18a) can be adjusted such that its length corresponds to the distance measured by the measuring device. The images in FIG. 61F can be displayed in response to pressing a button located immediately below the arrow displayed in FIG. 61E.

FIG. 61G shows a display screen shot which can provide a visual cue informing the user that the lateral malleolus can be palpated, and that a target probe (e.g target probe 18a) can be held or affixed adjacent the lateral malleolus. The screen in FIG. 61G can also provide a visual cue informing the user that a cross-hair laser can be directed towards the probe 18a, and the user can press a user input 26 to register the lateral malleolus. The images in FIG. 61G can be displayed in response to pressing a button located immediately below the arrow displayed in FIG. 61F.

FIG. 61H shows a display screen shot which can provide a visual cue informing the user that the medial malleolus can be palpated, and that a target probe (e.g. target probe 18b) can be held or affixed adjacent the medial malleolus. The screen in FIG. 61G can also provide a visual cue informing the user that a cross-hair laser can be directed towards the probe 18a, and the user can press a user input 26 to register the lateral malleolus. The images in FIG. 61H can be displayed in response to pressing a button located immediately below the arrow displayed in FIG. 61G.

FIG. 61I shows a display screen shot which can provide a visual cue informing the user that a universal jig (e.g. universal jig 16) can be adjusted to adjust the resection plane along the proximal tibia. In one embodiment, the screen can provide both an anterior-posterior angle and a varus/valgus angle of the cutting block 84 both in degree measurement and pictorially. The images in FIG. 61I can be displayed in response to pressing a button located immediately below the arrow displayed in FIG. 61H.

FIG. 61J shows a display screen shot which can provide a visual cue informing the user that the resection depth for the tibial cut can be set. For example, the screen can continue to provide both an anterior/posterior angle and a varus/valgus angle of the cutting block 84 in degree measurement and pictorially. The images of FIG. 61J can be displayed in response to pressing a button located immediately below the arrow displayed in FIG. 61I.

FIG. 61K shows a display screen shot which can provide a visual cue informing the user a tibial preparation procedure has completed. The screen can include a visual indication that once the procedure has been completed for one joint (e.g. left knee), the user can proceed to another joint. For example, the screen can include an arrow pointing to a user input 26. The user can press the user input 26 to proceed to the next joint. In other embodiments, the display 24 of the interactive user interface can be configured to automatically shut off after the procedure is completed.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method of performing an orthopedic procedure, comprising:
coupling an orthopedic fixture and a portable surgical orientation device with a distal portion of a limb that comprises a portion of a ball-and-socket joint, the portable surgical orientation device including a housing enclosing an inertial sensor and a microprocessor;
activating the inertial sensor within the portable surgical orientation device, such that the inertial sensor output is indicative of orientation, velocity, and/or position;
collecting the inertial sensor output from the inertial sensor using the portable surgical orientation device;
determining with the portable surgical orientation device a center of rotation of a ball portion of the limb based on the inertial sensor output; and determining with the portable surgical orientation device a location of the mechanical axis of the limb based on the inertial sensor output.

2. The method of claim 1, wherein the limb is a leg and further comprising:
moving a femur of the leg through a range of motion;
detecting the movement of the femur using the portable surgical orientation device;
determining the center of rotation of the femur based on the detected movement of the femur; and
determining the location of the mechanical axis of the femur based at least in part upon the location of the center of rotation of the femur and the location of the center of the knee.

3. The method of claim 1 further comprising:
coupling a cutting guide with the portable surgical orientation device;
securing the cutting guide to an anterior feature of the limb such that the cutting guide is substantially perpendicular to the mechanical axis; and
resecting a bone of the limb to define a plateau aligned with the mechanical axis of the limb.

4. The method of claim 1, further comprising:
moving the portable surgical orientation device and cutting guide in at least one degree of freedom; and
displaying an angle of the cutting guide based on the inertial sensor output.

5. The method of claim 1, further comprising:
aligning the orthopedic fixture with a distal anatomical landmark prior to coupling the orthopedic fixture with the limb;
aligning the portable surgical orientation device with a plurality of proximal anatomical landmarks adjacent a proximal region of the limb;
collecting positional information corresponding to the anatomical landmarks; and
determining the location of the mechanical axis of the limb based on the positional information of the anatomical landmarks.

6. The method of claim 5, wherein the proximal anatomical landmarks comprise the greater trochanter and the center of the head of the femur and the distal anatomical landmark comprises a point of entrance of the femoral canal.

7. The method of claim 1, further comprising:
collecting an inertial sensor output at an origin at time T0;
after collecting the inertial sensor output at the origin, collecting an inertial sensor output during motion of the inertial sensor toward a point spaced apart from the origin at time T1; and
collecting the inertial sensor output from the point spaced apart from the origin during movement of the inertial sensor back toward the origin at time T2.

8. The method of claim 7, further comprising:
performing an integration of the inertial sensor output from time T0 to time T1 to determine the position of the point spaced apart from the origin; and
performing an integration of the inertial sensor output from time T1 to time T2 to confirm the position of the point spaced apart from the origin.

9. The method of claim 1, further comprising indicating end points of ranges of motion by holding the inertial sensor steady for at least a minimum time period.

10. The method of claim 1, wherein determining the center of rotation comprises moving of a portion of the limb, and further comprising signaling to the portable surgical orientation device the start or end of such moving of the portion of the limb.

11. The method of claim 10, wherein signaling is provided by minimizing motion for a minimum period of time at a start or an end of a motion.

12. The method of claim 11, wherein the minimum period of time is at least one second.

13. The method of claim 1, wherein collecting further comprises:
[a] placing the limb at a first position;
[b] swinging the limb about an axis intersecting the ball portion of the limb to a second position spaced away from the first position;
[c] during or after swinging defined at [b], collecting inertial data;
[d] swinging the limb about an axis intersecting the ball portion of the limb to a third position away from the second and first positions; and
[e] during and/or after swinging defined at [d], collecting inertial data.

14. The method of claim 13, wherein swinging defined at [b] is about an anterior-posterior axis and swinging defined at [d] is about a medial-lateral axis.

15. The method of claim 14, further comprising
[f] swinging the limb about the anterior-posterior axis to a fourth position in the same plane as but away from the second position;
[g] during or after swinging defined at [f], collecting inertial data;
[h] swinging the limb about the medial-lateral axis to a fifth position in the same plane as but away from the third position; and
[i] during and/or after swinging defined at [h], collecting inertial data.

16. The method of claim 13, wherein the trajectory from the second position to the third position comprises a medial-lateral component and an anterior-posterior component.

17. The method of claim 16, wherein the second position is medial of the first position and the third position is anterior of the first position.

18. The method of claim 1, wherein the portable surgical orientation device is configured such that after the activating the inertial sensor and before determining the center of rotation, a bias value of the inertial sensor is determined.

19. The method of claim 18, wherein the bias value of the inertial sensor corresponds to acceleration of gravity or the location of the portable surgical orientation device in an Earth Centered Rotating (ECR) coordinate system.

20. A method of performing an orthopedic procedure, comprising:
coupling an orthopedic fixture and a portable surgical orientation device with a distal portion of a limb that comprises a portion of a ball-and-socket joint, the portable surgical orientation device including a housing enclosing an inertial sensor and a microprocessor;
activating the inertial sensor within the portable surgical orientation device, such that the inertial sensor output is indicative of orientation, velocity, and/or position;
collecting inertial data from the inertial sensor using the portable surgical orientation device; and
determining with the portable surgical orientation device a center of rotation of a ball portion of the limb based on the inertial sensor output.

* * * * *